US011203771B2

(12) United States Patent
Foster et al.

(10) Patent No.: US 11,203,771 B2
(45) Date of Patent: *Dec. 21, 2021

(54) MATERIALS AND METHODS FOR BIOSYNTHETIC MANUFACTURE OF CARBON-BASED CHEMICALS

(71) Applicant: INV Nylon Chemicals Americas, LLC, Wilmington, DE (US)

(72) Inventors: Alexander Brett Foster, Yarm (GB); Jonathan Kennedy, North Yorkshire (GB); Paul S. Pearlman, Thornton, PA (US)

(73) Assignee: INV Nylon Chemicals Americas, LLC, Wilmington, DE (US)

(*) Notice: Subject to any disclaimer, the term of this patent is extended or adjusted under 35 U.S.C. 154(b) by 67 days.

This patent is subject to a terminal disclaimer.

(21) Appl. No.: 16/372,083

(22) Filed: Apr. 1, 2019

(65) Prior Publication Data
US 2019/0352682 A1 Nov. 21, 2019

Related U.S. Application Data

(60) Provisional application No. 62/650,642, filed on Mar. 30, 2018.

(51) Int. Cl.
C12N 9/10 (2006.01)
C12P 13/00 (2006.01)

(52) U.S. Cl.
CPC .......... C12P 13/005 (2013.01); C12N 9/1096 (2013.01); C12N 9/13 (2013.01); C12Y 206/01002 (2013.01); C12Y 208/03001 (2013.01)

(58) Field of Classification Search
CPC .......... C12N 9/1096; C12Y 206/01002; C12Y 206/01018
See application file for complete search history.

(56) References Cited

U.S. PATENT DOCUMENTS

| | | | |
|---|---|---|---|
| 4,554,101 A | 11/1985 | Hopp | |
| 7,384,783 B2 | 6/2008 | Kunas et al. | |
| 9,580,733 B2 | 2/2017 | Botes et al. | |
| 9,637,764 B2 | 5/2017 | Botes et al. | |
| 9,862,973 B2 | 1/2018 | Botes et al. | |
| 9,920,339 B2 | 3/2018 | Botes et al. | |
| 10,072,150 B2 | 9/2018 | Botes et al. | |
| 10,196,657 B2 | 2/2019 | Botes et al. | |
| 10,577,634 B2* | 3/2020 | Pearlman | C12N 9/0008 |
| 2012/0003706 A1 | 1/2012 | Hickey | |
| 2012/0064622 A1 | 3/2012 | Fischer et al. | |
| 2013/0065285 A1 | 3/2013 | Sefton | |
| 2013/0323714 A1 | 12/2013 | Cheng et al. | |
| 2015/0315599 A1 | 11/2015 | Shetty et al. | |
| 2017/0218406 A1 | 8/2017 | Conradie et al. | |
| 2018/0023103 A1 | 1/2018 | Foster et al. | |
| 2018/0023104 A1 | 1/2018 | Cartman et al. | |

| | | | |
|---|---|---|---|
| 2019/0300838 A1 | 10/2019 | Smith et al. | |
| 2019/0300839 A1 | 10/2019 | Smith et al. | |
| 2019/0316072 A1 | 10/2019 | Smith et al. | |
| 2019/0338320 A1 | 11/2019 | Foster et al. | |

FOREIGN PATENT DOCUMENTS

| | | |
|---|---|---|
| EP | 0995490 A2 | 4/2000 |
| EP | 1728853 A1 | 12/2006 |
| EP | 1938892 A1 | 7/2008 |
| EP | 3399015 A1 | 11/2018 |
| WO | 2008094282 A1 | 8/2008 |
| WO | 2010003007 A2 | 1/2010 |
| WO | 2010069313 A2 | 6/2010 |
| WO | 2013090769 A2 | 6/2013 |
| WO | 2013152051 A2 | 10/2013 |
| WO | 2013186340 A1 | 12/2013 |
| WO | 2014093505 A2 | 6/2014 |
| WO | 2014105793 A1 | 7/2014 |
| WO | 2014105797 A2 | 7/2014 |
| WO | 2015195654 | 12/2015 |
| WO | 2015195654 A1 | 12/2015 |
| WO | 2017115855 A1 | 7/2017 |
| WO | 2017165244 A1 | 9/2017 |
| WO | 2018022633 A1 | 2/2018 |
| WO | 2018106549 A1 | 6/2018 |
| WO | 2018022595 A1 | 12/2018 |
| WO | 2019191761 A1 | 10/2019 |
| WO | 2019191763 A1 | 10/2019 |
| WO | 2019191767 A1 | 10/2019 |
| WO | 2019191770 A1 | 10/2019 |
| WO | 2019191772 A1 | 10/2019 |
| WO | 2019213108 A1 | 11/2019 |
| WO | 2019213118 A2 | 11/2019 |

OTHER PUBLICATIONS

Ishii et al., Uniprot database, accession No. G2J4X6, Nov. 2011.*
Raberg, et al., "A Closer Look on the Polyhydroxybutyrate- (PHB-) Negative Phenotype of Ralstonia Eutropha PHB-4", Plos One, vol. 9, No. 5, May 2014, pp. 1-11.
Russell, "The Energy Spilling Reactions of Bacteria and Other Organisms", Journal of Molecular Microbiology Biotechnology, vol. 13, No. 1, 2007, pp. 1-11.
Sillman, et al., "Isolation of Nonobligate Bacterial Predators of Bacteria from Soil", Canadian Journal of Microbiology, vol. 32, No. 9, 1986, pp. 760-762.
Zeph, et al., "Gram-Negative Versus Gram-Positive (Actinomycete) Nonobligate Bacterial Predators of Bacteria in Soil", Applied Environmental Microbiology, vol. 52, No. 4, Oct. 1986, pp. 819-823.
Lin et al., "Biotin Synthesis Beings by Hijacking the Fatty Acid Synthesis Pathway," Nat. Chem. Biol., vol. 6, Issue 9, 2010, pp. 682-688.

(Continued)

Primary Examiner — Maryam Monshipouri

(57) ABSTRACT

This disclosure relates to strategies for in vivo production of certain carbon-based products, for example, aminated aliphatic compounds having a carbon chain length of C5-C19.

17 Claims, 8 Drawing Sheets

Specification includes a Sequence Listing.

(56) References Cited

OTHER PUBLICATIONS

Slabu et al., "Discovery, Engineering and Synthetic Application of Transaminase Biocatalysts," ACS Catalysis 7, 2017, pp. 8263-8284.
Ishizuka, H., et al., "Putrescine oxidase of Micrococcus rubens : primary structure and *Escherichia coli*". Journal of General Microbiology, vol. 139, 1993, pp. 425-432.
Devereaux, et al., "A comprehensive set of sequence analysis programs for the VAX", Nucleic Acid Research, vol. 12, No. 1, 1984, pp. 387-395.
Kyte, J., et al., "A simple method for displaying the hydropathic character of a protein", vol. 157, Issue 1, May 5, 1982, pp. 105-132.
Smith et al., "Comparison of biosequences", Advances in Applied Mathematics, vol. 2, Issue 4, Dec. 1981, pp. 482-489.
Needleman et al., "A general method applicable to the search for similarities in the amino acid sequence of two proteins", Journal of Molecular Biology, vol. 48, 1970, pp. 443-453.
Pearson et al., "Improved tools for biological sequence comparison", PNAS, vol. 85, Issue 8, 1988, pp. 2444-2448.
Myers et al., "Optimal alignments in linear space", CABIOS, vol. 4, No. 1, 1988, pp. 11-17.
International Application No. PCT/US2019/025218 , "Invitation to Pay Additional Fees and, Where Applicable, Protest Fee", dated Jun. 25, 2019, 8 pages.
International Application Serial No. PCT/US2019/025218, Written Opinion dated Sep. 5, 2019, 9 pgs.
Chae, Tong Un., et al., "Metabolic engineering of *Escherichia coli* for the production of four-, five- and six-carbon lactams", Metabolic Engineering, Academic Press, Us, vol. 41, Apr. 5, 2017, pp. 82-91.
U.S. Appl. No. 16/372,083, Preliminary Amendment filed Jul. 30, 2019, 4 pgs.
International Application Serial No. PCT/US2019/025218, Invitation to Pay Additional Fees dated Jun. 25, 2019, 8 pgs.
International Application Serial No. PCT/US2019/025189, International Search Report dated Jul. 2, 2019, 5 pgs.
International Application Serial No. PCT/US2019/025189, Written Opinion dated Jul. 2, 2019, 7 pages.
International Application Serial No. PCT/US2019/029956, International Search Report dated Aug. 13, 2019, 5 pgs.
International Application Serial No. PCT/US2019/029956, Written Opinion dated Aug. 13, 2019, 10 pgs.
Jayashree, Chakravarty, et al., "Solvent production by engineered Ralstonia eutropha: channeling carbon to biofuel", Applied Microbiology and Biotechnology, vol. 102, (Apr. 29, 2018), XP036507417, early online publication Apr. 29, 2018, pp. 5021-5031.
Matthias, Raberg, et al., "Ralstonia eutropha H16 in progress: applications beside PHAs and establishment as production platform by advanced genetic tools", Critical Reviews In Biotechnology, vol. 38, (Dec. 12, 2017), XP002792845, early online publication Dec. 12, 2017, pp. 494-510 (Abstract Only).
Jillian, Marc, et al., "Over expression of GroESL in Cupriavidus necator for heterotrophic and autotrophic isopropanol production", Metabolic Engineering, vol. 42, XP085136193, 2017, pp. 74-84.
Hanko, Erik K. R.., et al., "Characterisation of a 3-hydroxypropionic acid-inducible system from Pseudomonas putida for orthogonal gene expression control in *Escherichia coli* and Cupriavidus necator",Scientific Reports, vol. 7, XP002792878, 2017, pp. 1-12.
Martin, Koller, et al., "Continuous production mode as a viable process-engineering tool for efficient poly (hydroxyalkanoate) (PHA) bio-production", Chemical and Biochemical Engineering Quarterly, vol. 28, XP002792820, 2014, pp. 65-77.
Swathi, Alagesan, et al., "Functional genetic elements for collrolling gene expression in Cupriavidus necator H16", Applied and Environmental Microbiology, vol. 84, (Oct. 2018), XP055604488, Oct. 2018, pp. 1-17.
Abayomi, Oluwanbe Johnson., et al., "An engineered constitutive promoter set with broad activity range for Cupriavidus necator H16", Acs Synthetic Biology, vol. 7, (Jun. 27, 2018), XP002792846, Jun. 27, 2018, pp. 1918-1928.

Hun-Suk, Song, et al., "Enhanced isobutanol production from acetate by combinatorial overexpression of acetyl-CoA synthetase and anaplerotic enzymes in engineered *Escherichia coli*", Biotechnology and Bioengineering, vol. 115, (May 2, 2018), XP002792879, May 2, 2018, pp. 1971-1978.
Janina, Kluge, et al., "Inducible promoters and functional genomic approaches for the genetic engineering of filamentous fungi", Applied Microbiology and Biotechnology, vol. 102, (Jun. 2, 2018), XP036546152, Jun. 2, 2018, pp. 6357-6372.
U.S. Appl. No. 16/399,155, Non Final Office Action dated Jul. 15, 2019, 19 pgs.
International Application Serial No. PCT/US2019/029973, International Search Report dated Jul. 23, 2019, 5 pgs.
International Application Serial No. PCT/US2019/029973, Written Opinion dated Jul. 23, 2019, 13 pgs.
Martin, Koller, "A review on established and emerging fermentation schemes for microbial production of polyhydroxyalkanoate (PHA) biopolyesters". Fermentation, vol. 4, (Apr. 23, 2018), XP002792757, early online publication Apr. 23, 2018, pp. 1-30.
Gabriela, Montiel-Jarillo, et al., "Enrichment of a mixed microbial culture for polyhydroxyalkanoates production: Effect of pH and N and P concentrations". Science of the Total Environment, vol. 583, XP029914697, 2017, pp. 300-307.
Fernando, Silva, et al., "Impact of nitrogen feeding regulation on polyhydroxyalkanoates production by mixed microbial cultures". New Biotechnology, vol. 37, XP029943712, 2017, pp. 90-98.
Justyna, Mozejko-Ciesielska, et al., "Bacterial polyhydroxyalkanoates: Still fabulous ?", Microbiological Research, vol. 192, XP029740446, 2016, pp. 271-282.
Jiachao, Zhu, et al., "Factors for promoting polyhydroxyalkanoate (PHA) synthesis in bio-nutrient-removal and recovery system," 4th International Conference on Environmental Systems Research (ICESR 2017) Conference paper, XP002792821, DOI: 10.1088/1755-1315/178/1/012021, cited as a P-document, but the conference was held in 2017 2018, pp. 1-4.
Kianoush, Khosravi-Darani, et al., "Simulation of bioreactors for poly(3-hydroxybutyrate) production from natural gas", Iranian Journal of Chemistry and Chemical Engineering, vol. 39, XP002792822, (Modeling of. . . ); online publication in late 2018, pp. 1-24.
International Application Serial No. PCT/US2019/025202, International Search Report dated Jul. 30, 2019, 5 pgs.
International Application Serial No. PCT/US2019/025202, Written Opinion dated Jul. 30, 2019, 10 pgs.
Jessup, M Shively., et al., "Something From Almost Nothing: Carbon Dioxide Fixation In Chemoautotrophs", Annu. Rev. Microbiol., vol. 52, 1998, pp. 191-230.
International Application Serial No. PCT/US2019/025211, International Search Report dated Jul. 29, 2019, 8 pgs.
International Application Serial No. PCT/US2019/025211, Written Opinion dated Jul. 29, 2019, 11 pgs.
Chi, Nguyen, et al., "Trapping the dynamic acyl carrier protein in fatty acid biosynthesis Nature", vol. 505, No. 7483, Dec. 22, 2013, pp. 427-431.
Feng, Yanbin, et al., "Tuning of acyl-ACP thioesterase activity directed for tailored fatty acid synthesis", Applied Microbiology and Biotechnology, Springer, De, vol. 102, No. 7, Feb. 22, 2018, pp. 3173-3182.
Robert, Haushalter W., et al., "Production of Odd-Carbon Dicarboxylic Acids in *Escherichia coli* Using an Engineered Biotin-Fatty Acid Biosynthetic Pathway", Journal of the American Chemical Society, vol. 139, No. 13, Mar. 21, 2017, pp. 4615-4618.
Joris, Beld, et al., "Evolution of acyl-ACP thioesterases and [beta]-ketoacyl-ACP synthases revealed by protein-protein interactions", Journal of Applied Phycology., vol. 26, No. 4, Nov. 22, 2013, pp. 1619-1629.
Marika, Ziesack, et al., "Chimeric Fatty Acyl-Acyl Carrier Protein Thioesterases Provide Mechanistic Insight into Enzyme Specificity and Expression", Applied And Environmental Microbiology, vol. 84, No. 10, Mar. 16, 2018.
Miglena, Manandhar, et al., "Pimelic acid, the first precursor of the B acillus subtilis biotin synthesis pathway, exists as the free acid and

(56) References Cited

OTHER PUBLICATIONS is assembled by fatty acid synthesis: Bacillus subtilis biotin synthesis", Molecular Microbiology., vol. 104, No. 4, Mar. 3, 2017, pp. 595-607.
Girdhar, Amandeep, et al., "Process Parameters for Influencing Polyhydroxyalkanoate Producing Bacterial Factories an Overview", Journal of Petroleum & Environmental Biotechnology; vol. 4, No. 5, Oct. 3, 2013, 8 pgs.
International Application Serial No. PCT/US2019/025194, International Search Report dated Aug. 22, 2019, 8 pgs.
International Application Serial No. PCT/US2019/025194, Written Opinion dated Aug. 22, 2019, 16 pgs.
Tanaka, K, et al., "Production of Poly (D-3-HydrOxybutyrate) From CO2, H2, and O2 by High Cell Density Autotropic Cultivation of Alcaligenes Eutrophus", Biotechnology and Bioengineering, Wiley, vol. 45, No. 3, (Feb. 5, 1995), XP000489583, Feb. 5, 1995, pp. 268-275.
International Application Serial No. PCT/US2019/025218, International Search Report dated Sep. 5, 2019, 8 pgs.
U.S. Appl. No. 16/399,155, Response filed Oct. 15, 2019 to Non-Final Office Action dated Jul. 15, 2019, 11 pgs.
Atlic, et al. Continuous Production of Poly([R]-3-Hydroxybutyrate) by Cupriavidus Necator in a Multistage Bioreactor Cascade, Appl Microbial Biotechnology, vol. 91, 2011, pp. 295-304.
Byrd, et al., "Bacterial Control of Agromyces Ramosus in Soil", Canadian Journal of Microbiology, vol. 31, No. 12, 1985, pp. 1157-1163.
Eggers, et al., "Impact of Ralstonia Eutropha's Poly(3-Hydroxybutyrate) (PHB) Depolymerases and Phasins on PHB Storage in Recombinant *Escherichia coli*", Applied and Environmental Microbiology, vol. 80, No. 24 Dec. 2014, pp. 7702-7709.
Horvat, et al., "Mathematical Modelling and Process Optimization of a Continuous 5-Stage Bioreactor Cascade for Production of Poly[-(R)-3-Hydroxybutyrate] by Cupriavidus Necator", Bioprocess Biosyst Eng, vol. 36, 2013, pp. 1235-1250.
Koller, et al., "Potential and Prospects of Continuous Polyhydroxyalkanoate (PHA) Production", Bioengineering May 29, 2015, pp. 94-121.
Kunasundari, et al., "Revisiting the Single Cell Protein Application of Cupriavidus Necator H16 and Recovering Bioplastic Granules Simultaneously", Plos One, vol. 8, No. 10, Oct. 2013, 15 pgs.
Makkar, et al., "*Cupriavidus necator* Gen. Nov., Sp. Nov.: A Nonobligate Bacterial Predator of Bacteria in Soil", International Journal of Systematic Bacteriology, vol. 37, No. 4, Oct. 1987, pp. 323-326.
"Crystal structure of the omega transaminase from Chromobacterium violaceum in complex with PMP", PDB: 6S4G_A, Dec. 1, 2020, 2 pages.
"TPA: aspartate aminotransferase family protein [*Betaproteobacteria bacterium*]", GenBank: HEL32111.1, Mar. 2, 2020, 1 page.
"Aminotransferase class III-fold pyridoxal phosphate-dependent enzyme [*Paludibacterium* sp. dN 18-1]", GenBank MTD33855.1, Nov. 24, 2019, 1 page.
"Aminotransferase class III-fold pyridoxal phosphate-dependent enzyme [*Neisseriaceae bacterium* B2N2-7]", GenBank: MXR37125.1, Jan. 6, 2020, 2 pages.
"Aaspartate aminotransferase family protein [*Chromobacterium haemolyticum*]", GenBank: OQS32233.1, Apr. 6, 2017, 2 pages.
"Aspartate aminotransferase family protein [*Chromobacterium haemolyticum*]", GenBank: OQS37730.1, Apr. 6, 2017, 2 pages.
"Aspartate aminotransferase family protein [*Pseudogulbenkiania ferrooxidans*]", NCBI Reference Sequence: WP_008952788.1, 2 pages.
"Aspartate aminotransferase family protein [*Chromobacterium violaceum*]", NCBI Reference Sequence: WP_011135573.1, Jul. 28, 2019, 1 page.
"Aspartate aminotransferase family protein [*Pseudogulbenkiania* sp. NH8B]", NCBI Reference Sequence: WP_014087389.1, Apr. 15, 2016, 2 pages.
"Multispecies: aspartate aminotransferase family protein [*Chromobacterium*]", NCBI Reference Sequence: WP_019104435.1, Apr. 18, 2017, 1 page.
"Aspartate aminotransferase family protein [*Pseudogulbenkiania ferrooxidans*]", NCBI Reference Sequence: WP_021478068.1, Apr. 15, 2016, 1 page.
"Aspartate aminotransferase family protein [*Pseudogulbenkiania* sp. MAI-1]", NCBI Reference Sequence: WP_024302818.1, 2 pages.
"Multispecies: aspartate aminotransferase family protein [*Microvirgula*]", NCBI Reference Sequence: WP_028498438.1, Jul. 14, 2018, 1 page.
"Aspartate aminotransferase family protein [*Paludibacterium yongneupense*]", NCBI Reference Sequence: WP_028535161.1, Apr. 15, 2016, 2 pages.
"Multispecies: aspartate aminotransferase family protein [*Chromobacterium*]", NCBI Reference Sequence: WP_043572477.1, Apr. 15, 2016, 1 page.
"Aspartate aminotransferase family protein [*Chromobacterium haemolyticum*]", NCBI Reference Sequence: WP_043593957.1, Apr. 15, 2016, 1 page.
"Multispecies: aspartate aminotransferase family protein [*Chromobacterium*]", NCBI Reference Sequence: WP_043629242.1, Oct. 31, 2016, 1 page.
"Multispecies: aspartate aminotransferase family protein [*Chromobacterium*]", WP_043638691.1, Nov. 11, 2020, 1 page.
"Multispecies: aspartate aminotransferase family protein [*Aquitalea*]", NCBI Reference Sequence: WP_045848621.1, Apr. 15, 2016, 1 page.
"Aspartate aminotransferase family protein [*Chromobacterium vaccinii*]", NCBI Reference Sequence: WP_046156378.1, Oct. 25, 2019, 1 page.
"Aspartate aminotransferase family protein [*Chromobacterium subtsugae*]", NCBI Reference Sequence: WP_047237256.1, Mar. 20, 2018, 1 page.
"Aspartate aminotransferase family protein [*Chromobacterium subtsugae*]", NCBI Reference Sequence: WP_047243213.1, Apr. 15, 2016, 1 page.
"Aspartate aminotransferase family protein [*Chromobacterium subtsugae*]", NCBI Reference Sequence: WP_047257673.1, Apr. 15, 2016, 1 page.
"Aspartate aminotransferase family protein [*Vogesella* sp. Eb]", NCBI Reference Sequence: WP_047966302.1, Apr. 15, 2016, 1 page.
"Aspartate aminotransferase family protein [*Chromobacterium violaceum*]", NCBI Reference Sequence: WP_048405256.1, Apr. 15, 2016, 1 page.
"Aspartate aminotransferase family protein [*Chromobacterium* sp. LK1]", NCBI Reference Sequence: WP_048411976.1, Apr. 15, 2016, 1 page.
"Aspartate aminotransferase family protein [*Chromobacterium* sp. LK11]", NCBI Reference Sequence: WP_048412320.1, Apr. 15, 2016, 1 page.
"Aspartate aminotransferase family protein [*Gulbenkiania mobilis*]", NCBI Reference Sequence: WP_054286466.1, May 14, 2017, 1 page.
"Aspartate aminotransferase family protein [*Gulbenkiania indica*]", NCBI Reference Sequence: WP_055434103.1, May 14, 2017, 1 page.
"Aspartate aminotransferase family protein [*Aquitalea magnusonii*]", NCBI Reference Sequence: WP_059287319.1, Dec. 31, 2020. 1 page.
"Aspartate aminotransferase family protein [*Chromobacterium sphagni*]", NCBI Reference Sequence: WP_071116856.1, Aug. 23, 2017, 1 page.
"Aspartate aminotransferase family protein [*Chromobacterium haemolyticum*]", NCBI Reference Sequence: WP_081556739.1, Apr. 8, 2017, 1 page.
"Aspartate aminotransferase family protein [*Chromobacterium violaceum*]", NCBI Reference Sequence: WP_081 573061.1, Apr. 8, 2017, 1 page.

(56) References Cited

OTHER PUBLICATIONS

"Aspartate aminotransferase family protein [*Chromobacterium haemolyticum*]", NCBI Reference Sequence: WP_081 576047.1, Apr. 8, 2017, 1 page.
"Aspartate aminotransferase family protein [*Pseudogulbenkiania subflava*]", NCBI Reference Sequence: WP_085275708.1, 1 page.
"Aspartate aminotransferase family protein [*Xenophilus* sp. AP218F]", NCBI Reference Sequence: WP_088737038.1, Jul. 3, 2017, 1 page.
"Aspartate aminotransferase family protein [*Vogesella* sp. LIG4]", NCBI Reference Sequence: WP_088967522.1, Jul. 11, 2017, 1 page.
"Aspartate aminotransferase family protein [*Aquitalea magnusonii*]", NCBI Reference Sequence: WP_089085350.1, Jul. 15, 2017, 1 page.
"Aspartate aminotransferase family protein [*Chromobacterium* sp. ATCC 53434]", NCBI Reference Sequence: WP_101708025.1, Jan. 10, 2018.
"Aspartate aminotransferase family protein [*Chromobacterium* sp. MWU13-2610]", NCBI Reference Sequence: WP_103321487.1, Jan. 31, 2018, 1 page.
"Multispecies: aspartate aminotransferase family protein [*Aquitalea*]", NCBI Reference Sequence: WP_103523625.1, Aug. 6, 2020, 1 page.
"Aspartate aminotransferase family protein [*Chromobacterium* sp. MWU14-2602]", NCBI Reference Sequence: WP_103903523.1, Feb. 10, 2018, 1 page.
"Aspartate aminotransferase family protein [*Chromobacterium vaccinii*]", NCBI Reference Sequence: WP_104946997.1, Mar. 4, 2018, 1 page.
"Aspartate aminotransferase family protein [*Chromobacterium amazonense*]", NCBI Reference Sequence: WP_106076402.1, Mar. 16, 2018, 1 page.
"Aspartate aminotransferase family protein [*Chromobacterium* sp. Panama]", NCBI Reference Sequence: WP_107799474.1, Apr. 25, 2018, 1 page.
"Aspartate aminotransferase family protein [*Chromobacterium phragmitis*]", NCBI Reference Sequence: WP_114062556.1.
"Aspartate aminotransferase family protein [*Vogesella indigofera*]",NCBI Reference Sequence: WP_120809711.1, Nov. 4, 2018, 1 page.
"Aspartate aminotransferase family protein [*Aquitalea* sp. FJL05]", NCBI Reference Sequence: WP_124643387.1, Apr. 12, 2019, 1 page.
"Aspartate aminotransferase family protein [*Paludibacterium purpuratum*]", NCBI Reference Sequence: WP_133682408.1, May 12, 2019, 1 page.
"Aspartate aminotransferase family protein [*Crenobacter* sp. GY 70310]", NCBI Reference Sequence: WP_136552942.1, Oct. 16, 2019, 1 page.
"Aspartate aminotransferase family protein [*Aquitalea* sp. THG-DN7.12]", NCBI Reference Sequence: WP_137009623.1, Oct. 16, 2019, 1 page.
"Aspartate aminotransferase family protein [*Vogesella urethralis*]", NCBI Reference Sequence: WP_144371715.1, Oct. 5, 2020, 1 page.
"Aspartate aminotransferase family protein [*Vogesella perlucida*]", NCBI Reference Sequence: WP_147687830.1, Oct. 5, 2020, 1 page.
"Aspartate aminotransferase family protein [*Vogesella mureinivorans*]", NCBI Reference Sequence: WP_147694092.1, Oct. 5, 2020, 1 page.
"Aspartate aminotransferase family protein [*Chromobacterium paludis*]", NCBI Reference Sequence: WP_149295777.1, Oct. 5, 2020, 1 page.
"Aspartate aminotransferase family protein [*Chromobacterium violaceum*]", NCBI Reference Sequence: WP_152637556.1, Oct. 31, 2019, 1 page.
"Aminotransferase class III-fold pyridoxal phosphate-dependent enzyme [*Aquitalea denitrificans*]", NCBI Reference Sequence: WP_159877958.1, Jan. 19, 2020, 1 page.
"Aspartate aminotransferase family protein [*Chromobacterium haemolyticum*]", NCBI Reference Sequence: WP_161523523.1, Oct. 5, 2020, 1 page.
"Aminotransferase class III—fold pyridoxal phosphate-dependent enzyme [*Crenobacter sedimenti*]", NCBI Reference Sequence: WP_163315775.1, Apr. 6, 2020, 1 page.
"Aminotransferase class III—fold pyridoxal phosphate-dependent enzyme [*Chromobacterium vaccinii*]", NCBI Reference Sequence: WP_166440807.1, Apr. 6, 2020, 1 page.
"Aminotransferase class III—fold pyridoxal phosphate-dependent enzyme [*Chromobacterium haemolyticum*]", NCBI Reference Sequence: WP_166453011.1, Apr. 6, 2020, 1 page.
"Aminotransferase class III—fold pyridoxal phosphate-dependent enzyme [*Vogesella oryzae*]", NCBI Reference Sequence: WP_174874069.1, 1 page.
"Aminotransferase class III—fold pyridoxal phosphate-dependent enzyme [*Aquitalea* sp. LB_tupeE]", NCBI Reference Sequence: WP_178973970.1, Jul. 11, 2020, 1 page.
"Aminotransferase class III—fold pyridoxal phosphate-dependent enzyme [*Vogesella fluminis*]", NCBI Reference Sequence: WP_189352298.1, Sep. 28, 2020, 1 page.
"Aminotransferase class III—fold pyridoxal phosphate-dependent enzyme [*Vogesella alkaliphila*]", NCBI Reference Sequence: WP_189374996.1, Sep. 28, 2020, 1 page.
"Aminotransferase class III—fold pyridoxal phosphate-dependent enzyme [*Paludibacterium paludis*]", NCBI Reference Sequence: WP_189532963.1, Sep. 28, 2020, 1 page.
Database UniProt, "RecName: Full=Thiopurine S-methyltransferase [ECO:0000256|HAMAPRule:MF_00812, ECO:0000256|SAAS:SAAS00896910}; EC=2.1. 1,67{ECO:0000256|HAMAP-Rule:MF_00812, ECO:0000256|SAAS SAAS00896910}; AltName: Full=Thiopurine methyltransferase {ECO: 0000256|HAMAP-Rule:MF_00812}", retrieved from EBI accession No. UNIPROT:A0A1 L8MA47 Database accession No. A0A1L8MA47, Mar. 15, 2017, 04 Pages.
Database UniProt, "SubName: Full=Acyl-ACP thioesterase {ECO:0000313| EMBLCDD77481.1}", retrieved from EBI accession No. EBI accession No. UNIPROT:R7CHF5 Database accession No. R7CHF5, Jul. 24, 2013, 03 Pages.
Database UniProt,"RecName: Full=Thiopurine S-methyltransferase [ECO:0000256|HAMAPRule:MF_00812, ECO:0000256|SAAS:SAAS00896910}; EC=2.1. 1,67{ECO:0000256|HAMAP-Rule:MF_00812, ECO:0000256|SAAS SAAS00896910}; AltName: Full=Thiopurine methyltransferase {ECO: 0000256|HAMAP-Rule:MF_00812}" ,retrieved from EBI accession No. UNIPROT:A0A009ZW4 Database accession No. A0A009ZVV4, Jun. 11, 2014, 04 Pages.
Kovacs et al., "Metabolic engineering of Cupriavidus necator H16 for the sustainable production of C3 and C5 monomers and polymers", Clnet Conference 4, Jan. 20-23, 2019 Conference paper {Abstract), 2019, p. 26.

* cited by examiner

SEQUENCE LISTING

```
<160> NUMBER OF SEQ ID NOS: 9

<210> SEQ ID NO 1
<211> LENGTH: 459
<212> TYPE: PRT
<213> ORGANISM: Chromobacterium violaceum

<400> SEQUENCE: 1

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80
```

```
Glu Leu Pro Phe Tyr Asn Thr Phe Phe Lys Thr Thr His Pro Ala Val
                     85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 2
<211> LENGTH: 24
<212> TYPE: PRT
<213> ORGANISM: Unknown
<220> FEATURE:
<223> OTHER INFORMATION: Description of Unknown:
``` periplasmic tag sequence

<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala Met Gly
            20

<210> SEQ ID NO 3
<211> LENGTH: 457
<212> TYPE: PRT
<213> ORGANISM: Escherichia coli

<400> SEQUENCE: 3

Met Met Glu Gly Gln Gln His Gly Glu Gln Leu Lys Arg Gly Leu Lys
1               5                   10                  15

Asn Arg His Ile Gln Leu Ile Ala Leu Gly Gly Ala Ile Gly Thr Gly
                20                  25                  30

Leu Phe Leu Gly Ser Ala Ser Val Ile Gln Ser Ala Gly Pro Gly Ile
            35                  40                  45

Ile Leu Gly Tyr Ala Ile Ala Gly Phe Ile Ala Phe Leu Ile Met Arg
        50                  55                  60

Gln Leu Gly Glu Met Val Val Glu Glu Pro Val Ala Gly Ser Phe Ser
65                  70                  75                  80

His Phe Ala Tyr Lys Tyr Trp Gly Ser Phe Ala Gly Phe Ala Ser Gly
                85                  90                  95

Trp Asn Tyr Trp Val Leu Tyr Val Leu Val Ala Met Ala Glu Leu Thr
                100                 105                 110

Ala Val Gly Lys Tyr Ile Gln Phe Trp Tyr Pro Glu Ile Pro Thr Trp
            115                 120                 125

Val Ser Ala Ala Val Phe Phe Val Ile Asn Ala Ile Asn Leu Thr
        130                 135                 140

Asn Val Lys Val Phe Gly Glu Met Glu Phe Trp Phe Ala Ile Ile Lys
145                 150                 155                 160

Val Ile Ala Val Val Ala Met Ile Ile Phe Gly Gly Trp Leu Leu Phe
                165                 170                 175

Ser Gly Asn Gly Gly Pro Gln Ala Thr Val Ser Asn Leu Trp Asp Gln
                180                 185                 190

Gly Gly Phe Leu Pro His Gly Phe Thr Gly Leu Val Met Met Met Ala
            195                 200                 205

Ile Ile Met Phe Ser Phe Gly Gly Leu Glu Leu Val Gly Ile Thr Ala
        210                 215                 220

Ala Glu Ala Asp Asn Pro Glu Gln Ser Ile Pro Lys Ala Thr Asn Gln
225                 230                 235                 240

Val Ile Tyr Arg Ile Leu Ile Phe Tyr Ile Gly Ser Leu Ala Val Leu
                245                 250                 255

Leu Ser Leu Met Pro Trp Thr Arg Val Thr Ala Asp Thr Ser Pro Phe
            260                 265                 270

Val Leu Ile Phe His Glu Leu Gly Asp Thr Phe Val Ala Asn Ala Leu
        275                 280                 285

Asn Ile Val Val Leu Thr Ala Ala Leu Ser Val Tyr Asn Ser Cys Val
        290                 295                 300

Tyr Cys Asn Ser Arg Met Leu Phe Gly Leu Ala Gln Gln Gly Asn Ala
305                 310                 315                 320

Pro Lys Ala Leu Ala Ser Val Asp Lys Arg Gly Val Pro Val Asn Thr

-continued

```
                325                 330                 335
Ile Leu Val Ser Ala Leu Val Thr Ala Leu Cys Val Leu Ile Asn Tyr
            340                 345                 350
Leu Ala Pro Glu Ser Ala Phe Gly Leu Leu Met Ala Leu Val Val Ser
            355                 360                 365
Ala Leu Val Ile Asn Trp Ala Met Ile Ser Leu Ala His Met Lys Phe
            370                 375                 380
Arg Arg Ala Lys Gln Glu Gln Gly Val Val Thr Arg Phe Pro Ala Leu
385                 390                 395                 400
Leu Tyr Pro Leu Gly Asn Trp Ile Cys Leu Leu Phe Met Ala Ala Val
            405                 410                 415
Leu Val Ile Met Leu Met Thr Pro Gly Met Ala Ile Ser Val Tyr Leu
            420                 425                 430
Ile Pro Val Trp Leu Ile Val Leu Gly Ile Gly Tyr Leu Phe Lys Glu
            435                 440                 445
Lys Thr Ala Lys Ala Val Lys Ala His
            450                 455
```

<210> SEQ ID NO 4
<211> LENGTH: 440
<212> TYPE: PRT
<213> ORGANISM: Bacillus subtilis

<400> SEQUENCE: 4

```
Met Ser Lys Lys Val Ser Ala Ser Tyr Ile Ile Ile Gly Leu Met
1               5                   10                  15
Leu Phe Ala Leu Phe Phe Gly Ala Gly Asn Leu Ile Phe Pro Pro Met
            20                  25                  30
Leu Gly Gln Leu Ala Gly Lys Asn Val Trp Val Ala Asn Ala Gly Phe
            35                  40                  45
Leu Val Thr Gly Val Gly Leu Pro Leu Leu Ala Ile Thr Ala Phe Val
            50                  55                  60
Phe Ser Gly Lys Gln Asn Leu Gln Ser Leu Ala Ser Arg Val His Pro
65                  70                  75                  80
Val Phe Gly Ile Val Phe Thr Thr Ile Leu Tyr Leu Ala Ile Gly Pro
            85                  90                  95
Phe Phe Ala Ile Pro Arg Ser Gly Asn Val Ser Phe Glu Ile Gly Val
            100                 105                 110
Lys Pro Phe Leu Ser Asn Asp Ala Ser Pro Val Ser Leu Ile Ile Phe
            115                 120                 125
Thr Ile Leu Phe Phe Ala Leu Ala Cys Leu Leu Ser Leu Asn Pro Ser
            130                 135                 140
Lys Ile Ile Asp Ile Val Gly Lys Phe Leu Thr Pro Ile Lys Leu Thr
145                 150                 155                 160
Phe Ile Gly Leu Leu Val Ala Val Ala Leu Ile Arg Pro Ile Gly Thr
            165                 170                 175
Ile Gln Ala Pro Ser Lys Gly Tyr Thr Ser Gln Ala Phe Phe Lys Gly
            180                 185                 190
Phe Gln Glu Gly Tyr Leu Thr Leu Asp Ala Leu Val Ala Phe Val Phe
            195                 200                 205
Gly Ile Ile Ile Val Asn Ala Leu Lys Glu Gln Gly Ala Ser Thr Lys
            210                 215                 220
Lys Gln Leu Ile Val Val Cys Ala Lys Ala Ala Ile Ala Ala Val
225                 230                 235                 240
```

```
Leu Leu Ala Val Met Tyr Thr Ala Leu Ser Tyr Met Gly Ala Ser Ser
                245                 250                 255

Val Glu Glu Leu Gly Ile Leu Glu Asn Gly Ala Glu Val Leu Ala Lys
            260                 265                 270

Val Ser Ser Tyr Tyr Phe Gly Ser Tyr Gly Ser Ile Leu Leu Gly Leu
        275                 280                 285

Met Ile Thr Val Ala Cys Leu Thr Thr Ser Val Gly Leu Ile Thr Ala
    290                 295                 300

Cys Ser Ser Phe Phe His Glu Leu Phe Pro Asn Ile Ser Tyr Lys Lys
305                 310                 315                 320

Ile Ala Val Val Leu Ser Val Phe Ser Thr Leu Val Ala Asn Ile Gly
                325                 330                 335

Leu Thr Gln Leu Ile Lys Val Ser Met Pro Val Leu Leu Thr Met Tyr
            340                 345                 350

Pro Ile Ala Ile Ser Leu Ile Phe Leu Thr Phe Leu His Ser Val Phe
        355                 360                 365

Lys Gly Lys Thr Glu Val Tyr Gln Gly Ser Leu Leu Phe Ala Phe Ile
    370                 375                 380

Ile Ser Leu Phe Asp Gly Leu Lys Ala Ala Gly Ile Lys Ile Glu Val
385                 390                 395                 400

Val Asn Arg Ile Phe Thr Gln Ile Leu Pro Met Tyr Asn Ile Gly Leu
                405                 410                 415

Gly Trp Leu Ile Pro Ala Ile Ala Gly Gly Ile Cys Gly Tyr Ile Leu
            420                 425                 430

Ser Ile Phe Arg Thr Lys Thr Ser
        435                 440

<210> SEQ ID NO 5
<211> LENGTH: 489
<212> TYPE: PRT
<213> ORGANISM: Corynebacterium glutamicum

<400> SEQUENCE: 5

Met Leu Ser Phe Ala Thr Leu Arg Gly Arg Ile Ser Thr Val Asp Ala
1               5                   10                  15

Ala Lys Ala Ala Pro Pro Ser Pro Leu Ala Pro Ile Asp Leu Thr
            20                  25                  30

Asp His Ser Gln Val Ala Gly Val Met Asn Leu Ala Ala Arg Ile Gly
        35                  40                  45

Asp Ile Leu Leu Ser Ser Gly Thr Ser Asn Ser Asp Thr Lys Val Gln
    50                  55                  60

Val Arg Ala Val Thr Ser Ala Tyr Gly Leu Tyr Tyr Thr His Val Asp
65                  70                  75                  80

Ile Thr Leu Asn Thr Ile Thr Ile Phe Thr Asn Ile Gly Val Glu Arg
                85                  90                  95

Lys Met Pro Val Asn Val Phe His Val Val Gly Lys Leu Asp Thr Asn
            100                 105                 110

Phe Ser Lys Leu Ser Glu Val Asp Arg Leu Ile Arg Ser Ile Gln Ala
        115                 120                 125

Gly Ala Thr Pro Pro Glu Val Ala Glu Lys Ile Leu Asp Glu Leu Glu
    130                 135                 140

Gln Ser Pro Ala Ser Tyr Gly Phe Pro Val Ala Leu Leu Gly Trp Ala
145                 150                 155                 160

Met Met Gly Gly Ala Val Ala Val Leu Leu Gly Gly Gly Trp Gln Val
                165                 170                 175
```

```
Ser Leu Ile Ala Phe Ile Thr Ala Phe Thr Ile Ile Ala Thr Thr Ser
            180                 185                 190

Phe Leu Gly Lys Lys Gly Leu Pro Thr Phe Phe Gln Asn Val Val Gly
            195                 200                 205

Gly Phe Ile Ala Thr Leu Pro Ala Ser Ile Ala Tyr Ser Leu Ala Leu
            210                 215                 220

Gln Phe Gly Leu Glu Ile Lys Pro Ser Gln Ile Ile Ala Ser Gly Ile
225                 230                 235                 240

Val Val Leu Leu Ala Gly Leu Thr Leu Val Gln Ser Leu Gln Asp Gly
            245                 250                 255

Ile Thr Gly Ala Pro Val Thr Ala Ser Ala Arg Phe Phe Glu Thr Leu
            260                 265                 270

Leu Phe Thr Gly Gly Ile Val Ala Gly Val Gly Leu Gly Ile Gln Leu
            275                 280                 285

Ser Glu Ile Leu His Val Met Leu Pro Ala Met Glu Ser Ala Ala Ala
            290                 295                 300

Pro Asn Tyr Ser Ser Thr Phe Ala Arg Ile Ile Ala Gly Gly Val Thr
305                 310                 315                 320

Ala Ala Ala Phe Ala Val Gly Cys Tyr Ala Glu Trp Ser Ser Val Ile
            325                 330                 335

Ile Ala Gly Leu Thr Ala Leu Met Gly Ser Ala Phe Tyr Tyr Leu Phe
            340                 345                 350

Val Val Tyr Leu Gly Pro Val Ser Ala Ala Ile Ala Ala Thr Ala
            355                 360                 365

Val Gly Phe Thr Gly Gly Leu Leu Ala Arg Arg Phe Leu Ile Pro Pro
            370                 375                 380

Leu Ile Val Ala Ile Ala Gly Ile Thr Pro Met Leu Pro Gly Leu Ala
385                 390                 395                 400

Ile Tyr Arg Gly Met Tyr Ala Thr Leu Asn Asp Gln Thr Leu Met Gly
            405                 410                 415

Phe Thr Asn Ile Ala Val Ala Leu Ala Thr Ala Ser Ser Leu Ala Ala
            420                 425                 430

Gly Val Val Leu Gly Glu Trp Ile Ala Arg Arg Leu Arg Arg Pro Pro
            435                 440                 445

Arg Phe Asn Pro Tyr Arg Ala Phe Thr Lys Ala Asn Glu Phe Ser Phe
            450                 455                 460

Gln Glu Glu Ala Glu Gln Asn Gln Arg Arg Gln Arg Lys Arg Pro Lys
465                 470                 475                 480

Thr Asn Gln Arg Phe Gly Asn Lys Arg
            485

<210> SEQ ID NO 6
<211> LENGTH: 414
<212> TYPE: PRT
<213> ORGANISM: Bacillus subtilis

<400> SEQUENCE: 6

Met Lys Lys Leu Ile Ala Phe Gln Ile Leu Ile Ala Leu Ala Val Gly
1               5                   10                  15

Ala Val Ile Gly His Phe Phe Pro Asp Phe Gly Met Ala Leu Arg Pro
            20                  25                  30

Val Gly Asp Gly Phe Ile Arg Leu Ile Lys Met Ile Val Val Pro Ile
            35                  40                  45

Val Phe Ser Thr Ile Val Ile Gly Ala Ala Gly Ser Gly Ser Met Lys
```

```
            50                  55                  60
Lys Met Gly Ser Leu Gly Ile Lys Thr Ile Ile Trp Phe Glu Val Ile
 65                  70                  75                  80

Thr Thr Leu Val Leu Gly Leu Gly Leu Leu Leu Ala Asn Val Leu Lys
                 85                  90                  95

Pro Gly Val Gly Leu Asp Leu Ser His Leu Ala Lys Lys Asp Ile His
            100                 105                 110

Glu Leu Ser Gly Tyr Thr Asp Lys Val Val Asp Phe Lys Gln Met Ile
        115                 120                 125

Leu Asp Ile Ile Pro Thr Asn Ile Ile Asp Val Met Ala Arg Asn Asp
130                 135                 140

Leu Leu Ala Val Ile Phe Phe Ala Ile Leu Phe Gly Val Ala Ala Ala
145                 150                 155                 160

Gly Ile Gly Lys Ala Ser Glu Pro Val Met Lys Phe Phe Glu Ser Thr
                165                 170                 175

Ala Gln Ile Met Phe Lys Leu Thr Gln Ile Val Met Val Thr Ala Pro
            180                 185                 190

Ile Gly Val Leu Ala Leu Met Ala Ala Ser Val Gly Gln Tyr Gly Ile
        195                 200                 205

Glu Leu Leu Leu Pro Met Phe Lys Leu Val Gly Thr Val Phe Leu Gly
    210                 215                 220

Leu Phe Leu Ile Leu Phe Val Leu Phe Pro Leu Val Gly Leu Ile Phe
225                 230                 235                 240

Gln Ile Lys Tyr Phe Glu Val Leu Lys Met Ile Trp Asp Leu Phe Leu
                245                 250                 255

Ile Ala Phe Ser Thr Thr Ser Thr Glu Thr Ile Leu Pro Gln Leu Met
            260                 265                 270

Asp Arg Met Glu Lys Tyr Gly Cys Pro Lys Arg Val Val Ser Phe Val
        275                 280                 285

Val Pro Ser Gly Leu Ser Leu Asn Cys Asp Gly Ser Ser Leu Tyr Leu
    290                 295                 300

Ser Val Ser Cys Ile Phe Leu Ala Gln Ala Phe Gln Val Asp Met Thr
305                 310                 315                 320

Leu Ser Gln Gln Leu Leu Met Met Leu Val Leu Val Met Thr Ser Lys
                325                 330                 335

Gly Ile Ala Ala Val Pro Ser Gly Ser Leu Val Val Leu Leu Ala Thr
            340                 345                 350

Ala Asn Ala Val Gly Leu Pro Ala Glu Gly Val Ala Ile Ile Ala Gly
        355                 360                 365

Val Asp Arg Val Met Asp Met Ala Arg Thr Gly Val Asn Val Pro Gly
    370                 375                 380

His Ala Ile Ala Cys Ile Val Val Ser Lys Trp Glu Lys Ala Phe Arg
385                 390                 395                 400

Gln Lys Glu Trp Val Ser Ala Asn Ser Gln Thr Glu Ser Ile
                405                 410

<210> SEQ ID NO 7
<211> LENGTH: 501
<212> TYPE: PRT
<213> ORGANISM: Corynebacterium glutamicum

<400> SEQUENCE: 7

Met Asn Thr Gln Ser Asp Ser Ala Gly Ser Gln Gly Ala Ala Ala Thr
 1               5                  10                  15
```

-continued

```
Ser Arg Thr Val Ser Ile Arg Thr Leu Ile Ala Leu Ile Ile Gly Ser
             20                  25                  30
Thr Val Gly Ala Gly Ile Phe Ser Ile Pro Gln Asn Ile Gly Ser Val
         35                  40                  45
Ala Gly Pro Gly Ala Met Leu Ile Gly Trp Leu Ile Ala Gly Val Gly
     50                  55                  60
Met Leu Ser Val Ala Phe Val Phe His Val Leu Ala Arg Arg Lys Pro
 65                  70                  75                  80
His Leu Asp Ser Gly Val Tyr Ala Tyr Ala Arg Val Gly Leu Gly Asp
                 85                  90                  95
Tyr Val Gly Phe Ser Ser Ala Trp Gly Tyr Trp Leu Gly Ser Val Ile
            100                 105                 110
Ala Gln Val Gly Tyr Ala Thr Leu Phe Phe Ser Thr Leu Gly His Tyr
        115                 120                 125
Val Pro Leu Phe Ser Gln Asp His Pro Phe Val Ser Ala Leu Ala Val
    130                 135                 140
Ser Ala Leu Thr Trp Leu Val Phe Gly Val Val Ser Arg Gly Ile Ser
145                 150                 155                 160
Gln Ala Ala Phe Leu Thr Thr Val Thr Thr Val Ala Lys Ile Leu Pro
                165                 170                 175
Leu Leu Cys Phe Ile Ile Leu Val Ala Phe Leu Gly Phe Ser Trp Glu
            180                 185                 190
Lys Phe Thr Val Asp Leu Trp Ala Arg Asp Gly Gly Val Gly Ser Ile
        195                 200                 205
Phe Asp Gln Val Arg Gly Ile Met Val Tyr Thr Val Trp Val Phe Ile
    210                 215                 220
Gly Ile Glu Gly Ala Ser Val Tyr Ser Arg Gln Ala Arg Ser Arg Ser
225                 230                 235                 240
Asp Val Ser Arg Ala Thr Val Ile Gly Phe Val Ala Val Leu Leu Leu
                245                 250                 255
Leu Val Ser Ile Ser Ser Leu Ser Phe Gly Val Leu Thr Gln Gln Glu
            260                 265                 270
Leu Ala Ala Leu Pro Asp Asn Ser Met Ala Ser Val Leu Glu Ala Val
        275                 280                 285
Val Gly Pro Trp Gly Ala Ala Leu Ile Ser Leu Gly Leu Cys Leu Ser
    290                 295                 300
Val Leu Gly Ala Tyr Val Ser Trp Gln Met Leu Cys Ala Glu Pro Leu
305                 310                 315                 320
Ala Leu Met Ala Met Asp Gly Leu Ile Pro Ser Lys Ile Gly Ala Ile
                325                 330                 335
Asn Ser Arg Gly Ala Ala Trp Met Ala Gln Leu Ile Ser Thr Ile Val
            340                 345                 350
Ile Gln Ile Phe Ile Ile Ile Phe Phe Leu Asn Glu Thr Thr Tyr Val
        355                 360                 365
Ser Met Val Gln Leu Ala Thr Asn Leu Tyr Leu Val Pro Tyr Leu Phe
    370                 375                 380
Ser Ala Phe Tyr Leu Val Met Leu Ala Thr Arg Gly Lys Gly Ile Thr
385                 390                 395                 400
His Pro His Ala Gly Thr Arg Phe Asp Asp Ser Gly Pro Glu Ile Ser
                405                 410                 415
Arg Arg Glu Asn Arg Lys His Leu Ile Val Gly Leu Val Ala Thr Val
            420                 425                 430
Tyr Ser Val Trp Leu Phe Tyr Ala Ala Glu Pro Gln Phe Val Leu Phe
```

```
            435                 440                 445
Gly Ala Met Ala Met Leu Pro Gly Leu Ile Pro Tyr Val Trp Thr Arg
        450                 455                 460

Ile Tyr Arg Gly Glu Gln Val Phe Asn Arg Phe Glu Ile Gly Val Val
465                 470                 475                 480

Val Val Leu Val Val Ala Ala Ser Ala Gly Val Ile Gly Leu Val Asn
                485                 490                 495

Gly Ser Leu Ser Leu
            500

<210> SEQ ID NO 8
<211> LENGTH: 512
<212> TYPE: PRT
<213> ORGANISM: Marinobacter salarius

<400> SEQUENCE: 8

Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
                20                  25                  30

Leu Gly Lys Val Val Leu Glu Lys Leu Ile Arg Thr Val Pro Asp Ile
            35                  40                  45

Gly Gly Ile His Leu Leu Ile Arg Gly Asn Lys Arg His Pro Ala Ala
        50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Ser Phe Leu Glu Glu Arg
                85                  90                  95

Val His Cys Ile Thr Gly Glu Val Thr Glu Pro Arg Phe Gly Leu Thr
            100                 105                 110

Gln Glu Arg Phe Arg Ala Leu Ala Gly Gln Val Asp Ala Phe Ile Asn
        115                 120                 125

Ser Ala Ala Ser Val Asn Phe Arg Glu Glu Leu Asp Lys Ala Leu Lys
130                 135                 140

Ile Asn Thr Leu Cys Leu Glu Asn Val Ala Ala Leu Ala Glu Leu Asn
145                 150                 155                 160

Ser Thr Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Ala Asp Gly Tyr Tyr Glu Thr Glu Leu Val His
        195                 200                 205

Leu Leu Gln Asp Lys Ile Ser Asp Val Lys Ala Arg Tyr Ser Gly Lys
210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
290                 295                 300
```

```
Val Ser Leu Phe Pro Gly Lys Arg Ser Gly Ile Asp Val Ile Pro
305                 310                 315                 320

Val Asp Leu Val Ala Asn Ser Ile Ile Leu Ser Leu Ala Glu Ala Ile
                325                 330                 335

Ser Glu Pro Gly His Arg Arg Ile Tyr Gln Cys Cys Ser Gly Gly Ser
                340                 345                 350

Asn Pro Ile Ser Leu Gly Thr Phe Ile Asp Tyr Leu Met Ala Glu Ala
                355                 360                 365

Lys Ser Asn Tyr Ala Ala Tyr Asp Gln Leu Phe Tyr Arg Arg Pro Thr
370                 375                 380

Lys Pro Phe Val Ala Val Asn Arg Lys Leu Phe Asp Val Val Gly
385                 390                 395                 400

Gly Met Arg Val Pro Leu Ser Ile Ala Gly Lys Ala Leu Arg Leu Ala
                405                 410                 415

Gly Gln Asn Arg Glu Leu Lys Val Leu Lys Asn Leu Asp Thr Thr Arg
                420                 425                 430

Ser Leu Ala Thr Ile Phe Gly Phe Tyr Thr Ala Pro Asp Tyr Ile Phe
                435                 440                 445

Arg Asn Asp Ser Leu Met Ala Leu Ala Ser Arg Met Gly Glu Leu Asp
450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Gln Thr Arg Lys Lys Ala Ala
                500                 505                 510

<210> SEQ ID NO 9
<211> LENGTH: 511
<212> TYPE: PRT
<213> ORGANISM: Marinobacter lipolyticus

<400> SEQUENCE: 9

Met Val Gln Gln Leu Gln Thr Ser Glu Leu Ser Ser Thr Val Leu Glu
1               5                   10                  15

Gln Leu Arg Gly Lys His Val Leu Val Thr Gly Thr Thr Gly Phe Leu
                20                  25                  30

Gly Lys Val Val Leu Glu Lys Leu Ile Arg Ala Val Pro Asp Ile Gly
                35                  40                  45

Gly Ile His Leu Leu Ile Arg Gly Asn Lys Arg His Pro Asn Ala Arg
                50                  55                  60

Glu Arg Phe Phe His Glu Ile Ala Thr Ser Ser Val Phe Glu Arg Leu
65                  70                  75                  80

Arg Gln Glu Asp Asn Glu Ala Phe Glu Ala Phe Ile Glu Glu Arg Val
                85                  90                  95

His Cys Ile Thr Gly Glu Val Thr Lys Pro Arg Phe Gly Leu Thr Pro
                100                 105                 110

Glu Arg Phe Thr Thr Leu Ala Asn Gln Ala Asp Ala Phe Ile Asn Ser
                115                 120                 125

Ala Ala Ser Val Asn Phe Arg Glu Glu Leu Asp Lys Ala Leu Thr Ile
                130                 135                 140

Asn Thr Leu Cys Leu Asn Asn Val Val Glu Leu Ala Arg Arg Asn Arg
145                 150                 155                 160

Lys Met Ala Val Ile Gln Val Ser Thr Cys Tyr Val Asn Gly Lys Asn
                165                 170                 175
```

-continued

```
Ser Gly Gln Val Thr Glu Ser Val Ile Lys Pro Ala Gly Glu Ser Ile
            180                 185                 190

Pro Arg Ser Thr Ala Gly Tyr Tyr Glu Ile Glu Glu Leu Val Arg Leu
        195                 200                 205

Leu Glu Asp Lys Ile Ala Asp Val Arg Ser Arg Tyr Ser Gly Lys Val
    210                 215                 220

Leu Glu Lys Lys Leu Val Asp Leu Gly Ile Gln Glu Ala Asn Arg Tyr
225                 230                 235                 240

Gly Trp Ser Asp Thr Tyr Thr Phe Thr Lys Trp Leu Gly Glu Gln Leu
                245                 250                 255

Leu Met Lys Ala Leu Asp Gln Arg Ala Leu Thr Ile Val Arg Pro Ser
            260                 265                 270

Ile Ile Glu Ser Ala Leu Glu Glu Pro Ala Pro Gly Trp Ile Glu Gly
        275                 280                 285

Val Lys Val Ala Asp Ala Ile Ile Leu Ala Tyr Ala Arg Glu Lys Val
    290                 295                 300

Thr Leu Phe Pro Gly Lys Arg Ser Gly Ile Ile Asp Val Ile Pro Val
305                 310                 315                 320

Asp Leu Val Ala Asn Ala Ile Ile Leu Ser Leu Ala Glu Ala Leu Ala
                325                 330                 335

Glu Ala Pro Gln Arg Arg Ile Tyr Gln Cys Cys Ser Gly Ser Ser Asn
            340                 345                 350

Pro Ile Ser Leu Gly Glu Phe Ile Asp His Leu Met Ala Glu Ser Lys
        355                 360                 365

Ala Asn Tyr Ala Ala Tyr Asp Gln Leu Phe Tyr Arg Gln Pro Ser Lys
    370                 375                 380

Pro Phe Ile Ala Val Asn Arg Lys Leu Phe Asp Ala Val Val Gly Gly
385                 390                 395                 400

Met Arg Val Pro Leu Ser Leu Thr Ser Arg Val Met Arg Met Leu Gly
                405                 410                 415

Gln Asn Arg Glu Leu Lys Thr Leu Arg Asn Leu Asp Thr Ser Arg Ser
            420                 425                 430

Leu Ala Thr Ile Phe Gly Phe Tyr Thr Ala Pro Asp Tyr Ile Phe Arg
        435                 440                 445

Asn Asp Ser Leu Gln Ala Leu Ala Ser Arg Met Gly Glu Arg Asp Gln
    450                 455                 460

Ala Leu Phe Pro Val Asp Ala Arg Arg Ile Asp Trp Ser Leu Tyr Leu
465                 470                 475                 480

Arg Lys Ile His Leu Ala Gly Leu Asn Gln Tyr Ala Leu Lys Glu Arg
                485                 490                 495

Lys Leu Tyr Ser Leu Arg Ser Ala Lys Ala Arg Lys Gln Ala Ala
            500                 505                 510
```

MATERIALS AND METHODS FOR BIOSYNTHETIC MANUFACTURE OF CARBON-BASED CHEMICALS

CROSS REFERENCE TO RELATED APPLICATION

The present application claims the benefit of U.S. Provisional Patent Application No. 62/650,642 filed Mar. 30, 2018, which is incorporated herein by reference for all purposes.

SEQUENCE LISTING

The instant application contains a Sequence Listing which has been filed electronically in ASCII format and is hereby incorporated by reference in its entirety. Said ASCII copy, created on Jul. 24, 2019, is named 061646-1131148_(00701US)_SL.txt and is 33,428 bytes in size.

FIELD OF THE INVENTION

This disclosure relates to strategies for in vivo production of certain carbon-based products, for example, aminated aliphatic compounds having a carbon chain length of C5-C19. In some aspects of the present invention, in vivo production of aminated aliphatic compounds having a carbon chain length of C5-C19 is enhanced by altering the reaction conditions of a transamination reaction catalyzed by a polypeptide or a functional fragment thereof having a ω-transaminase activity.

BACKGROUND OF THE INVENTION

Polyamides, such as nylons, can be synthesized by the condensation polymerization of a diamine with a dicarboxylic acid or alternatively by the condensation polymerization of lactams. Nylon 6,6 is a ubiquitous nylon produced by the reaction of hexamethylenediamine (HMD) and adipic acid. Nylon 6 is produced by a ring opening polymerization of caprolactam. Nylon 7 represents a novel polyamide with value-added characteristics compared to Nylon 6 and Nylon 6,6. However, no economically favorable petrochemical routes exist to produce intermediates for nylon synthesis.

Biotechnology offers an alternative approach to producing these intermediates, for example, 7-Aminoheptanoic acid (7-AHA), via biocatalysis. Biocatalysis is the use of biological catalysts, such as enzymes, to perform biochemical transformations of organic compounds. A biochemical pathway for the production of 7-AHA utilizes the biotin biosynthesis pathway in *E. coli* (Lin et al., "Biotin Synthesis Beings by Hijacking the Fatty Acid Synthesis Pathway," *Nat. Chem. Biol.* 6(9): 682-688 2010). The first committed step in biotin biosynthesis is the methylation of malonyl-ACP by BioC. The malonyl-ACP methyl ester thus generated then serves as a starter unit for the fatty acid biosynthesis pathway.

Two rounds of fatty acid elongation and reduction then occur to generate pimeloyl-ACP methyl ester. Pimeloyl-ACP is then generated by the removal of the methyl group by the esterase BioH (FIG. 1).

Pimeloyl-ACP is an intermediate of the biotin pathway in *E. coli* and is converted to 7-AHA via a synthetic metabolic pathway utilising the action of a Thioesterase (TE) to release pimelic acid from pimeloyl-ACP, followed by a reduction to the semialdehyde catalyzed by a carboxylic acid reductase (CAR) and the final catalytic step of amination of the semialdehyde by a ω-Transaminase (ω-TAM) to produce 7-AHA. The export of 7-AHA from the cell is then facilitated by a transport protein, for example, LysE. See FIG. 2.

ω-TAMs are key enzymes that catalyze the conversion of substrates into products, for example, the conversion of pimelate semialdehyde into 7-AHA, using an amino donor, by catalyzing the exchange of the keto group (=O) on the pimelate semialdehyde with an amine group ($NH_2$). See FIG. 3. However, their use in biosynthetic processes is hindered by a number of factors, including, but not limited to, equilibrium thermodynamics, product inhibition, and poor substrate tolerance (Slabu et al. "Discovery, Engineering and Synthetic Application of Transaminase Biocatalysts," *ACS Catalysis* 7: 8263-8284 (2017). Given these factors, in vivo biosynthesis of carbon-based products, using a transamination reaction catalyzed by a ω-TAM, is limited.

BRIEF SUMMARY OF THE INVENTION

This disclosure is based at least in part on the discovery that it is possible to construct biochemical pathways that utilize a ω-transaminase for production of aminated aliphatic compounds having a carbon chain length of C5-C19. In some aspects, the disclosure relates to altering a transamination reaction catalyzed by a ω-transaminase in favor of product formation. In some aspects, the reaction conditions of a reaction catalyzed by the ω-transaminase are altered to increase production of aminated aliphatic compounds having a carbon chain length of C5-C19, such as, but not limited to, certain carbon-based products within the 7-AHA and 6-aminohexanoic acid (6-AHA) biosynthesis pathways.

The present invention, in one embodiment, provides various methods for enhancing biosynthesis in vivo. In some embodiments, the methods comprise: obtaining at least one organism capable of biosynthesizing at least one product, the at least one organism being unaltered or altered, wherein the organism utilizes a polypeptide having a ω-transaminase activity to catalyze a transamination reaction, wherein the polypeptide or a functional fragment thereof has at least 70% identity to SEQ ID NO: 1; and culturing the organism under conditions suitable for biosynthesis, wherein the organism biosynthesizes the at least one product, wherein the product is an aminated aliphatic compound having a carbon chain length of C5-C19 or a salt thereof.

In some embodiments, the product is an aminated aliphatic compound having a carbon chain length of C6-C7, or a salt thereof. In some embodiments, the product is 7-AHA or 6-aminohexanoic acid or a salt thereof. In some embodiments, the product is an amino alcohol, such as 7-aminoheptanol or 6-aminohexanol or a salt thereof. In some embodiments, the product is a diamine such as heptamethylenediamine or hexamethylenediamine or a salt thereof. In some embodiments, total product yield is increased.

In some embodiments, the reaction is catalyzed by a polypeptide or a functional fragment thereof having the activity of a ω-transaminase classified under EC 2.6.1.18, EC 2.6.1.19, EC 2.6.1.29, EC 2.6.1.48 or EC 2.6.1.82.

In some embodiments, the transamination reaction conditions are altered to increase ω-transamination activity of the polypeptide or functional fragment thereof as compared to an organism where transamination reaction conditions have not been altered.

In some embodiments, the step of altering the reaction conditions of the transamination reaction comprises catalyzing the reaction with a polypeptide or functional fragment thereof having a ω-transaminase activity comprising one or more amino acid substitution(s) relative to a wild-type ω-transaminase, wherein the one or more amino acid substitution(s) are at amino acid(s) that occupy position(s) corresponding to position(s) 2, 13, 15, 16, 20, 87, 134, 288 or 345 of SEQ ID NO: 1.

In some embodiments, the one or more amino acid substitutions are in the small binding pocket (O-pocket) and/or in the large binding pocket (P-pocket) of the polypeptide having a ω-transaminase activity. In some embodiments, the polypeptide has increased enzymatic activity and/or improved substrate specificity relative to a wild-type ω-transaminase classified under EC 2.6.1.18, EC 2.6.1.19, EC 2.6.1.29, EC 2.6.1.48 or EC 2.6.1.82. In some embodiments, the wild-type ω-transaminase is a *Chromobacterium violaceum* ω-transaminase or a *Chromobacterium violaceum*-like ω-transaminase. In some embodiments, the polypeptide has an increase in enzymatic activity of at least 10% relative to the wild-type ω-transaminase.

In some embodiments, the polypeptide has a reduced $K_m$ for an amino donor relative to the wild-type ω-transaminase. In some embodiments, the amino donor is L-alanine. In some embodiments, the $K_m$ for the amino donor is less than about 4 mmol·L$^{-1}$. In some embodiments, the polypeptide having a ω-transaminase activity has an increased $K_m$ for an aminated aliphatic compound having a carbon chain length of C5-C19 as an amino group donor relative to the wild-type ω-transaminase. In some embodiments, the aminated aliphatic compound has a carbon chain length of C6-C7. In some embodiments, the aminated aliphatic compound is 7-AHA or 6-aminohexanoic acid or a salt thereof. In some embodiments, the product is an amino alcohol, such as 7-aminoheptanol or 6-aminohexanol or a salt thereof. In some embodiments, the product is a diamine such as heptamethylenediamine or hexamethylenediamine or a salt thereof.

In some embodiments, the step of altering the reaction conditions of the transamination reaction comprises cyclization. In some embodiments, the step of altering comprises cyclization of the product. In some embodiments, the organism utilizes a polypeptide having *Clostridium propionicum* β-alanine CoA transferase activity to cyclize the product. In some embodiments, the polypeptide having β-alanine CoA converts 7-AHA to heptanolactam, wherein the amount of pimelate semialdehyde formed from the reverse reaction of ω-transaminase with 7-AHA is reduced.

In some embodiments, the step of altering the reaction conditions of the transamination reaction comprises increasing the level of an intracellular amino group donor in the organism. In some embodiments, the amino group donor is exogenously introduced into the organism. In some embodiments, the organism utilizes a polypeptide having L-amino acid dehydrogenase activity to increase the intracellular level of the amino group donor in the cell. In some embodiments, the L-amino acid dehydrogenase is L-alanine dehydrogenase.

In some embodiments, the step of altering the reaction conditions of the transamination reaction comprises using an amino donor which forms a volatile product and drives the transamination reaction towards product formation. In an embodiment, the amino donor may be isopropylamine.

In some embodiments, the altering the reaction conditions of the transamination reaction step comprises removing or otherwise reducing availability of the product. In some embodiments, the organism utilizes a polypeptide having amino acid transporter activity to remove or otherwise reduce the availability of the product. In some embodiments, the polypeptide having amino acid transporter activity has LysE amino acid transporter activity.

In some embodiments, the amount of at least one product formed from a reverse reaction of the polypeptide having a ω-transaminase activity and an aminated aliphatic compound having a carbon chain length of C5-C19 is reduced. In some embodiments, the amount of pimelate semialdehyde formed from the reverse reaction of ω-transaminase with 7-AHA is reduced.

In some embodiments, the method further comprises purifying the product.

In some embodiments, the organism is prokaryotic. In some embodiments, the organism is eukaryotic. In some embodiments, the organism is a recombinant organism. In some embodiments, the recombinant organism comprises at least one exogenous nucleic acid encoding at least one polypeptide having the activity of at least one enzyme depicted in FIG. 2. In some embodiments, the at least one exogenous nucleic acid encodes at least one polypeptide that has the activity of a ω-transaminase, thioesterase activity or carboxylate reductase.

In some embodiments, the recombinant organism comprises an exogenous nucleic acid encoding an L-amino acid dehydrogenase. In some embodiments, the L-amino acid dehydrogenase is L-alanine dehydrogenase.

In some embodiments, the recombinant organism overexpresses one or more genes encoding: an acetyl-CoA synthetase, a β-alanine CoA transferase, a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter, a dicarboxylate transporter, an amino acid transporter, and/or a multidrug transporter.

In some embodiments, the recombinant organism overexpresses a gene encoding an amino acid transporter. In some embodiments, the recombinant organism overexpresses a gene encoding a LysE transporter.

In some embodiments, the recombinant organism produces an increased level of 7-AHA converted from pimelic acid or pimelic acid derivatives, as compared to a wild-type organism. In some embodiments, the pimelic acid derivatives comprise pimelyl-ACP and pimelate semialdehyde. In some embodiments, the pimelate semialdehyde is transaminated to produce 7-AHA. In some embodiments, the recombinant organism comprises a nucleic acid encoding a polypeptide having *Clostridium propionicum* β-alanine CoA transferase activity, wherein the polypeptide cyclizes the product. In some embodiments, the polypeptide having β-alanine CoA converts 7-AHA to heptanolactam, wherein the amount of pimelate semialdehyde formed from the reverse reaction of ω-transaminase with 7-AHA.

In some embodiments, altering the reaction conditions of the transamination reaction comprises increasing the amount of an intracellular amino group donor, cyclizing the product and/or removing the product from the cell.

In some embodiments, altering the reaction conditions of the transamination reaction comprises increasing the amount of an intracellular amino group donor and cyclizing the product.

In some embodiments, altering the reaction conditions of the transamination reaction comprises increasing the amount of an intracellular amino group donor and removing the product from the cell.

In some embodiments, altering the reaction conditions of the transamination reaction comprises increasing the amount of an intracellular amino donor, cyclizing the product and removing the product from the cell.

In some embodiments, the organism is subjected to a cultivation strategy under aerobic, anaerobic or, microaerobic cultivation conditions. In some embodiments, the organism is cultured under conditions of nutrient limitation. In some embodiments, the principal carbon source fed to the fermentation derives from a biological feedstock or non-biological feedstock. In some embodiments, the organism's tolerance to high concentrations of the product is improved through continuous cultivation in a selective environment.

In another embodiment, provided herein is a recombinant organism comprising an exogenous nucleic acid encoding a polypeptide having ω transaminase activity, wherein the polypeptide or a functional fragment thereof has at least 70% identity to SEQ ID NO: 1, and wherein the recombinant organism produces an increased level of an aminated aliphatic compound having a carbon chain length of C5-C19 as compared to a wild-type organism. In some embodiments, the recombinant organism is prokaryotic. In some embodiments, the recombinant organism is eukaryotic.

In some embodiments, the aminated aliphatic compound produced by the recombinant organism has a carbon chain length of C6-C7. In some embodiments, the aminated aliphatic compound produced by the recombinant organism is 7-AHA or 6-aminohexanoic acid or a salt thereof. In some embodiments, the product is an amino alcohol, such as 7-aminoheptanol or 6-aminohexanol or a salt thereof. In some embodiments, the product is a diamine such as heptamethylenediamine or hexamethylenediamine or a salt thereof. In some embodiments, the exogenous nucleic acid encodes a polypeptide having a ω-transaminase activity and comprising one or more amino acid substitution(s) relative to a wild-type ω-transaminase, wherein the one or more amino acid substitution(s) are at amino acid(s) that occupy position(s) corresponding to position(s) 2, 13, 15, 16, 20, 87, 134, 288 or 345 of SEQ ID NO: 1, or a functional fragment thereof.

In some embodiments, the recombinant organism comprises at least one exogenous nucleic acid encoding at least one polypeptide having the activity of at least one enzyme depicted in FIG. 2. In some embodiments, the recombinant organism comprises at least one exogenous nucleic acid encoding at least one polypeptide having ω-transaminase, thioesterase activity or carboxylate reductase activity. In some embodiments, the recombinant organism further comprises an exogenous nucleic acid encoding an L-amino acid dehydrogenase. In some embodiments, the the L-amino acid dehydrogenase is L-alanine dehydrogenase. In some embodiments, the recombinant organism overexpresses one or more genes encoding: an acetyl-CoA synthetase; a β-alanine CoA transferase; a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; an amino acid transporter; and/or a multidrug transporter. In some embodiments, the recombinant organism overexpresses a gene encoding an amino acid transporter. In certain embodiments, the recombinant organism overexpresses a gene encoding a LysE transporter.

In another embodiment, provided herein is a method of increasing production of caprolactam comprising: culturing a host organism comprising (i) a nucleic acid encoding a polypeptide having a ω-transaminase activity or a functional fragment thereof, wherein the polypeptide has at least 70% identity to SEQ ID NO: 1; and (ii) a nucleic acid encoding a polypeptide having the activity of a β-alanine CoA transferase in the presence of a suitable substrate or metabolic intermediate and under conditions suitable for the conversion of adipic acid or adipic acid derivatives to caprolactam and purifying the caprolactam.

In some embodiments, the polypeptide having a ω-transaminase activity or a functional fragment thereof has one or more amino acid substitution(s) relative to a wild-type ω-transaminase, wherein the one or more amino acid substitution(s) are at amino acid(s) that occupy position(s) corresponding to position(s) 2, 13, 15, 16, 20, 87, 134, 288 or 345 of SEQ ID NO: 1, or a functional fragment thereof. In some embodiments, the polypeptide having the activity of a β-alanine CoA transferase converts 6-AHA to caprolactam, wherein the amount of adipic acid semialdehyde formed from the reverse reaction of ω-transaminase with 6-AHA.

In some embodiments, the polypeptide having a ω-transaminase activity or a functional fragment thereof has the activity of a ω-transaminase classified under EC 2.6.1.18, EC 2.6.1.19, EC 2.6.1.29, EC 2.6.1.48 or EC 2.6.1.82.

In some embodiments, the adipic acid derivatives comprise adipoyl-ACP and adipic acid semialdehyde. In some embodiments, the adipic acid semialdehyde is transaminated to produce 6-AHA. In some embodiments, the host organism is recombinant. In some embodiments, the host organism comprises at least one exogenous nucleic acid encoding at least one polypeptide having the activity of at least one enzyme depicted in FIG. 9.

Also provided, in another embodiment, is a bioderived aminated aliphatic compound having a carbon chain length of C5-C19, heptanolactam, caprolactam or salt thereof that is produced by any of the methods provided herein.

Further provided, in another embodiment, is a product comprising a chemical produced from any of the bioderived product described herein, wherein the product comprises a nylon intermediate, a polyester, a pharmaceutical, a biofuel, a fragrance or a food additive.

Also provided, in another embodiment is a bio-derived, bio-based or fermentation-derived product, wherein said product comprises: i. a composition comprising at least one bio-derived, bio-based or fermentation-derived compound, or salts thereof, produced or biosynthesized according to any of the methods provided herein;
ii. a bio-derived, bio-based or fermentation-derived polymer comprising the bio-derived, bio-based or fermentation-derived composition or compound of i., or any combination thereof; iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof; iv. a substance obtained by molding the bio-derived, bio-based or fermentation-derived polymer of ii. or the bio-derived, bio-based or fermentation-derived resin of iii., or any combination thereof v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, biobased or fermentation-derived substance of iv, or any combination thereof; or a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

BRIEF DESCRIPTION OF THE FIGURES

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

DETAILED DESCRIPTION

Figure 1:
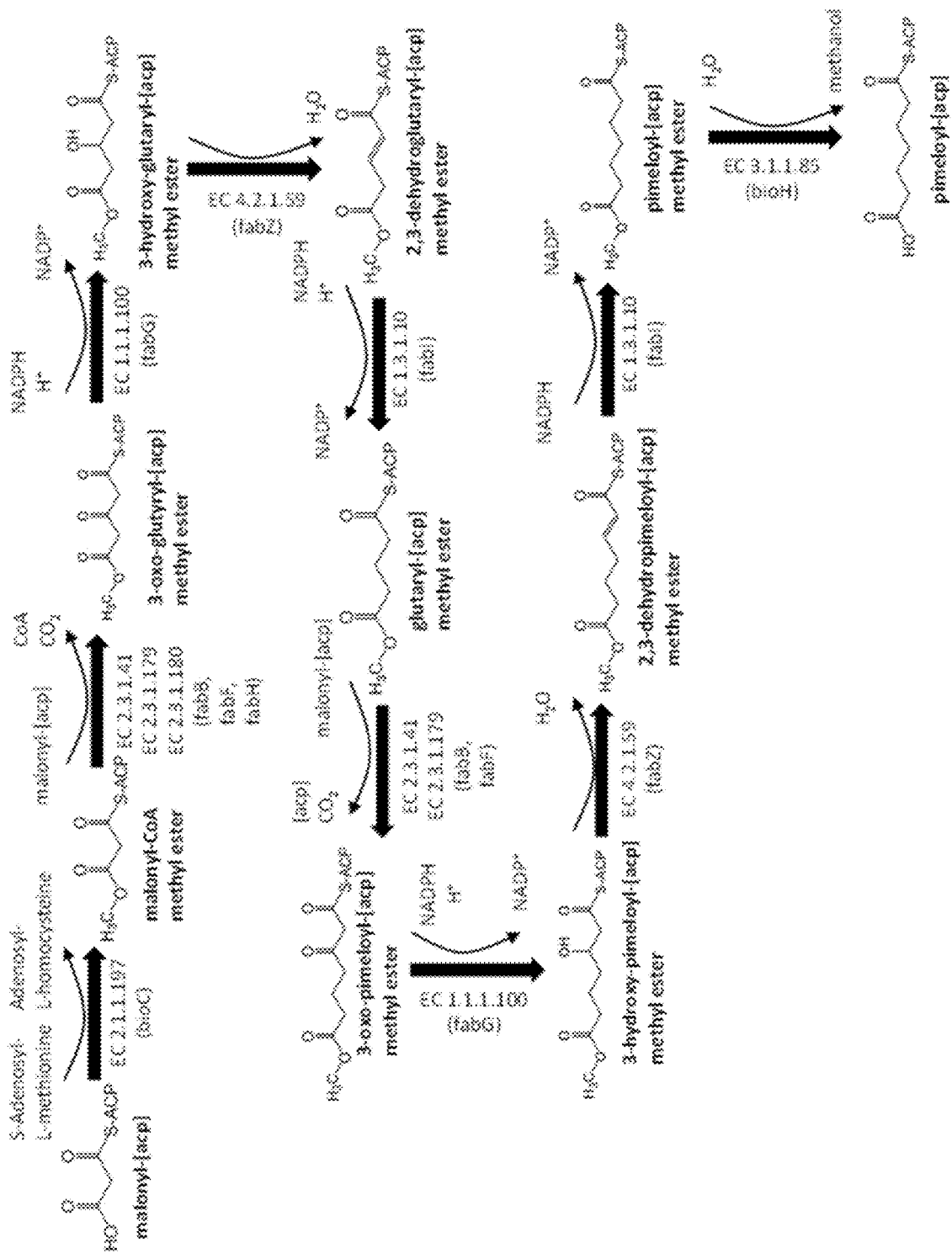
FIG. 1 is a schematic of an exemplary biochemical pathway for the production of pimeloyl-ACP from malonyl-ACP.

All references cited herein and the material for which they are cited are hereby specifically incorporated by reference in their entireties.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range.

Definitions

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The practice of the present disclosure will employ, unless otherwise indicated, conventional techniques of microbiology, tissue culture, molecular biology, chemistry, biochemistry and recombinant DNA technology, which are within the skill of the art. The materials, methods and examples are illustrative only and not limiting. The following is presented by way of illustration and is not intended to limit the scope of the disclosure.

In some embodiments, numbers expressing quantities of reagents, properties, reaction conditions and results, and so forth, used to describe and claim certain embodiments of the present disclosure are to be understood as being modified in some instances by the term "about," In some embodiments, the numerical parameters set forth in the specification (into which the claims are incorporated in their entirety) are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practical. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

As used in this specification and the appended claims, the singular forms "a," "an," and "the" include plural reference unless the context clearly dictates otherwise.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). The structures of these twenty natural amino acids are shown in, e.g., Stryer et al., *Biochemistry*, 5*th* ed., Freeman and Company (2002). The term "amino acid" also includes unnatural amino acids, modified amino acids (e.g., having modified side chains and/or backbones), and amino acid analogs.

As used herein, the term "bioderived" means derived from or synthesized by a biological organism. Bioderived compounds can be considered a renewable resource since they can be generated by a biological organism. Such a biological organism, in particular the microbial organisms disclosed herein, can utilize feedstock or biomass such as sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

For compounds containing carboxylic acid groups such as organic monoacids, hydroxyacids, amino acids and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. The salt can be isolated as is from the system as the salt or converted to the free acid by reducing the pH to below the pKa through addition of acid or treatment with an acidic ion exchange resin.

For compounds containing amine groups such as but not limited to organic amines, amino acids and diamine, these compounds may be formed or converted to their ionic salt form by addition of an acidic proton to the amine to form the ammonium salt formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases are known in the art and include aluminum hydroxide, calcium hydroxide, potassium hydroxide, sodium carbonate, sodium hydroxide, and the like. The salt can be isolated as is from the system as a salt or converted to the free amine by raising the pH to above the pKb through addition of base or treatment with a basic ion exchange resin.

For compounds containing both amine groups and carboxylic acid groups such as but not limited to amino acids, these compounds may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-acid), carboxylic acid, glucoheptonic acid, 4,4'-methylenebis-(3-hydroxy-2-ene-1-carboxylic 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid. Acceptable inorganic bases include aluminum hydroxide, calcium hydroxide, potassium hydroxide, sodium carbonate, sodium hydroxide, and the like or 2) replacing an acidic proton present in the parent compound by a metal ion, e.g., an alkali metal ion, an alkaline earth ion, or an aluminum ion; or coordinating with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate, sodium hydroxide, and the like. The salt can be isolated as is from the system or converted to the free acid by reducing the pH to below the pKa through addition of acid or treatment with an acidic ion exchange resin.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition that "comprises," "has" or "includes" one or more features is not limited to possessing only those one or more features and can cover other unlisted features. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element as essential to the practice of the present disclosure.

As used herein, "consisting essentially of" means the inclusion of additional sequences in a polynucleotide or polypeptide sequence provided herein where the additional sequences do not materially affect the basic function of the claimed polynucleotide or polypeptide sequences. With regard to compositions in general, the term "consisting essentially of" refers to those elements required for a given embodiment and additionally permits the presence of elements that do not materially affect the basic and novel or functional characteristic(s) of that embodiment of the disclosure.

As used herein, the term "consisting of" refers to compositions, methods, and respective components thereof as described herein, which are exclusive of any element not recited in that description of the embodiment.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen, Microbiol.* 139:425-32)) can be modified to yield a functionally identical molecule. Accordingly, each silent variation of a nucleic acid, which encodes a polypeptide of the present disclosure, is implicit in each described polypeptide sequence and incorporated herein by reference.

As to amino acid sequences, one of skill will recognize that individual substitutions, deletions or additions to a nucleic acid, peptide, polypeptide or protein sequence which alters, adds, or deletes a single amino acid or a small percentage of amino acids in the encoded sequence is a "conservatively modified variant" when the alteration results in the substitution of an amino acid with a chemically similar amino acid. Thus, any number of amino acid residues can be so altered. Conservatively modified variants typically provide equivalent biological activity as the unmodified polypeptide sequence from which they are derived. Conservative substitution tables providing functionally similar amino acids, also referred herein as "equivalent amino acids" are well known in the art.

As used herein, "codon optimization" is the process of modifying a nucleotide sequence in a manner that improves its expression, G/C content, RNA secondary structure, and translation in eukaryotic cells, without altering the amino acid sequence it encodes. Altered codon usage is often employed to alter translational efficiency and/or to optimize the coding sequence for expression in a desired host or to optimize the codon usage in a heterologous sequence for expression in a particular host. Codon usage in the coding regions of the polynucleotides of the present disclosure can be analyzed statistically using commercially available software packages such as "Codon Preference" available from the University of Wisconsin Genetics Computer Group. See, Devereaux, et al., (1984) *Nucleic Acids Res.* 12:387-395 or MacVector 4.1 (Eastman Kodak Co., New Haven, Conn.). Thus, the present disclosure provides a codon usage frequency characteristic of the coding region of at least one of the polynucleotides of the present disclosure. The number of polynucleotides (3 nucleotides per amino acid) that can be used to determine a codon usage frequency can be any integer from 3 to the number of polynucleotides of the present disclosure as provided herein. Optionally, the polynucleotides will be full-length sequences. An exemplary number of sequences for statistical analysis can be at least 1, 5, 10, 20, 50 or 100.

"Correspondence" to another sequence (e.g., regions, fragments, nucleotide or amino acid positions, or the like), for example, SEQ ID NO: 1, is based on the convention of numbering according to nucleotide or amino acid position number and then aligning the sequences in a manner that maximizes the percentage of sequence identity. Because not all positions within a given "corresponding region" need be identical, non-matching positions within a corresponding region may be regarded as "corresponding positions."

The term "derived" encompasses the terms "originated from", "obtained" or "obtainable from", and "isolated from".

"Equivalent amino acids" can be determined either on the basis of their structural homology with the amino acids for which they are substituted or on the results of comparative tests of biological activity between the various variants likely to be generated. As a non-limiting example, the list below summarizes possible substitutions often likely to be carried out without resulting in a significant modification of the biological activity of the corresponding variant:

1) Alanine (A), Serine (S), Threonine (T), Valine (V), Glycine (G), and Proline (P);
2) Aspartic acid (D), Glutamic acid (E);
3) Asparagine (N), Glutamine (Q);
4) Arginine (R), Lysine (K), Histidine (H);
5) Isoleucine (I), Leucine (L), Methionine (M), Valine (V); and
6) Phenylalanine (F), Tyrosine (Y), Tryptophan (W).

See also, Creighton, Proteins, W. H. Freeman and Co. (1984).

In making such changes/substitutions, the hydropathic index of amino acids may also be considered. The importance of the hydropathic amino acid index in conferring interactive biologic function on a protein is generally understood in the art (Kyte and Doolittle; (1982) *J. Mol Biol.* 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred; those which are within +1 are particularly preferred and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues; arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally occurring nucleic acid is considered to be exogenous to a host once in the host. It is important to note that non-naturally occurring nucleic acids can contain nucleic acid subsequences or fragments of nucleic acid sequences that are found in nature, provided the nucleic acid as a whole does not exist in nature. For example, a nucleic acid molecule containing a genomic DNA sequence within an expression vector is a non-naturally occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be a non-naturally occurring nucleic acid. It follows that genomic DNA fragments produced by PCR or restriction endonuclease treatment as well as cDNAs are considered to be non-naturally occurring nucleic acids since they exist as separate molecules not found in nature. It also follows that any nucleic acid containing a promoter sequence and polypeptide-encoding sequence (e.g., cDNA or genomic DNA) in an arrangement not found in nature is a non-naturally occurring nucleic acid. A nucleic acid that is naturally occurring can be exogenous to a particular host microorganism.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

As used herein, Enzyme Classification (EC) Numbers (EC numbers) are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction catalyzed. For example, in some embodiments, the ω-transaminase is classified under EC 2.6.1.18, EC 2.6.1.19, EC 2.6.1.29, EC 2.6.1.48 or EC 2.6.1.82. In some embodiments, a polypeptide having a ω-transaminase activity or a functional fragment thereof has a ω-transaminase activity of an enzyme classified under EC 2.6.1.18, EC 2.6.1.19, EC 2.6.1.29, EC 2.6.1.48 or EC 2.6.1.82 In specific embodiments, the ω-transaminase converts pimelate semialdehyde to 7-AHA.

As used herein, "expression" refers to the process by which a polypeptide is produced based on the nucleic acid sequence of a gene. The process includes both transcription and translation.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, or enhancers and sequences which control termination of transcription and translation.

Functional fragments of any of the polypeptides described herein can also be used in the methods of the disclosure. The term "functional fragment" as used herein refers to a peptide fragment of a protein that has at least 25% (e.g., at least 30%, 40%, 50%, 60%, 70%, 75%, 80%, 85%, 90%, 95%, 98%, 99%, 100%, or even greater than 100%) of the activity of the corresponding mature, full-length, wild-type protein. The functional fragment can generally, but not always, be comprised of a continuous region of the protein, wherein the region has functional activity.

A "gene" refers to a DNA segment that is involved in producing a polypeptide and includes regions preceding and following the coding regions as well as intervening sequences (introns) between individual coding segments (exons).

A "host strain", "host cell" or "host organism" means a suitable host for an expression vector or DNA construct comprising a polynucleotide encoding a polypeptide according to the disclosure. Populations of host cells are also suitable for performing any of methods described herein. Specifically, host strains may be bacterial cells, mammalian cells, insect cells, and other cloning or "expression systems." Host organisms or microorganisms described herein can include endogenous pathways that can be manipulated such that selected carbon-based products blocks can be produced, for example, an aminated aliphatic compound having a carbon chain length of C5-C19. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host. In some embodiments, the host organism comprises exogenous enzymes and endogenous enzymes such that all of the enzymes within the pathway are expressed in the host.

In an embodiment of the disclosure, "host cell" means both the cells and protoplasts created from the cells of a microbial strain. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Heterologous" with reference to a polynucleotide or protein refers to a polynucleotide or protein/polypeptide that does not naturally occur in a host cell. In some embodiments, the protein is a commercially important industrial protein. It is intended that the term encompass proteins that are encoded by naturally occurring genes, mutated genes, and/or synthetic genes.

The terms "identical" or percent "identity," in the context of two or more nucleic acids or polypeptide sequences, refer to two or more sequences or subsequences that are the same or have a specified percentage of nucleotides or amino acid residues that are the same (e.g., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Sequences are "substantially identical" to each other if they are at least 20%, at least 25%, at least 30%, at least 35%, at least 40%, at least 45%, at least 50%, or at least 55% identical. Optionally, the identity exists over a region that is at least about 50 nucleotides in length, or more typically over a region that is 100 to 500 or 1000 or more nucleotides in length.

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci.* USA 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution and this process results in "sequence homology" of, e.g., at least 90%, 91%, 92%, 93%, 94%, 95%, 96%, 97%, 98%, or 99%. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

"Introduced" in the context of inserting a nucleic acid sequence into a cell, includes "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA). The term can also refer to the translocation of the nucleic acid sequence from outside a cell to inside a cell. In some cases, introducing refers to translocation of a nucleic acid from outside the cell to inside the nucleus of the cell.

With regard to enzymatic activity, "$K_{cat}$ ($S^{-1}$)" is the overall catalytic rate of the enzyme, or the maximum number of enzymatic reactions catalyzed per second. This constant is also referred to as the "turnover number" of the enzyme or the number of substrate molecules each enzyme site converts to product per unit time. "$K_m$" is the substrate concentration required for the enzymatic reaction to occur at one-half $V_{max}$, or one-half its maximal rate.

As used herein, a metabolically engineered microorganism is an organism produced via the introduction of genetic material into a host or parental microorganism of choice thereby modifying or altering the cellular physiology and biochemistry of the microorganism.

The term "mutant," refers to both polypeptides and nucleic acids. The term "mutant" may be used interchangeably with the term "variant" or "synthetic". Mutants or variants include alterations, insertions, substitutions, transversions, truncations, and/or inversions at one or more locations in the amino acid or nucleotide sequence, respectively, of a parent sequence. In the context of a synthetic polypeptides having an ω-TAM activity, a mutant ω-TAM means a polypeptide, typically recombinant, that comprises one or more amino acid modifications, for example, one or more substitutions, relative to a corresponding, ω-TAM, for example, a wild-type ω-TAM. In some embodiments, the mutant ω-TAMs of the present invention are non-naturally occurring.

As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

The term "nucleic acid" encompasses DNA, cDNA, RNA, heteroduplexes, and synthetic molecules capable of encoding a polypeptide. RNA includes mRNA, RNA, RNAi, siRNA, cRNA and autocatalytic RNA. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. A nucleic acid comprises a nucleotide sequence which typically includes nucleotides that comprise an A, G, C, T or U base. However, nucleotide sequences may include other bases such as, without limitation inosine, methylcytosine, methylinosine, methyladenosine and/or thiouridine, although without limitation thereto. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. A nucleic acid can be or can include, e.g., a chromosome or chromosomal segment, a vector (e.g., an expression vector), an expression cassette, a naked DNA or RNA polymer, or the product of a polymerase chain reaction (PCR), an oligonucleotide, a probe, and a primer. Unless otherwise indicated, a particular nucleic acid sequence optionally comprises or encodes complementary sequences, in addition to any sequence explicitly indicated.

The term "operably linked" and its variants refer to chemical fusion or bonding or association of sufficient stability to withstand conditions encountered in the nucleotide incorporation methods utilized, between a combination of different compounds; molecules or other entities such as, but not limited to: between a mutant polymerase and a reporter moiety (e.g., fluorescent dye or nanoparticle); between a nucleotide and a reporter moiety (e.g., fluorescent dye); or between a promoter and a coding sequence, if it controls the transcription of the sequence.

A "promoter" is a regulatory sequence that is involved in binding RNA polymerase to initiate transcription of a gene. The promoter may be an inducible promoter or a constitutive promoter. An exemplary promoter used herein is a T7 promoter, which is an inducible promoter.

A "periplasmic tag" or "periplasmic leader sequence" is a sequence of amino acids which, when attached to/present at the N-terminus of a protein/peptide, directs the protein/peptide to the bacterial periplasm, where the sequence is often removed by a signal peptidase. Protein/peptide secretion into the periplasm can increase the stability of recombinantly-expressed proteins/peptides. An example of a periplasmic tag disclosed herein is provided as SEQ ID NO: 2. (MKYLLPTAAAGLLLLAAQPAMAMG).

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

"Recombinant" when used in reference to an organism, a cell, nucleic acid, protein or vector indicates that the organism, cell, nucleic acid, protein or vector has been modified by the introduction of a "heterologous nucleic acid" or protein, or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. A recombinant nucleic acid can be originally formed in vitro, in general, by the manipulation of a nucleic acid by endonucleases, in a form not normally found in nature. Thus an isolated ω-TAM, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A recombinant protein can be made using recombinant techniques, i.e., through the expression of a recombinant nucleic acid as depicted above. A recombinant protein is typically distinguished from a naturally occurring protein by at least one or more characteristics.

A "signal sequence" or "signal peptide" means a sequence of amino acids bound to the N-terminal portion of a protein, which facilitates the secretion of the mature form of the protein outside the cell. The definition of a signal sequence is a functional one. The mature form of the extracellular protein lacks the signal sequence which is cleaved off during the secretion process.

"Selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

"Substrate" refers to a molecule that an enzyme binds to and converts to a product. Pimelate semialdehyde is an example of a substrate that is converted to 7-AHA by a ω-TAM, for example, any of the polypeptide having an ω-TAM activity described herein.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

As used herein, "transformed cell" includes cells that have been transformed or transduced by use of recombinant DNA techniques. Transformation typically occurs by insertion of one or more nucleotide sequences into a cell. The inserted nucleotide sequence may be a "heterologous nucleotide sequence," i.e., is a sequence that is not natural to the cell that is to be transformed, such as a fusion protein.

As used herein, "transformed", "stably transformed", "transduced," and "transgenic" used in reference to a cell means the cell has a non-native (e.g., heterologous) nucleic acid sequence integrated into its genome or as an episomal plasmid that is maintained through multiple generations.

The term "vector", as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the claimed embodiments are intended to include such other forms of expression vectors, such as viral vectors (e.g., replication defective retroviruses, adenoviruses and adeno-associated viruses), which serve equivalent functions. Vectors also include cloning vectors, shuttle vectors, plasmids, phage particles, cassettes and the like.

The term "wild-type," in the context of a nucleotide sequence or polypeptide sequence, refers to the major or most common allele of the sequence as it occurs in nature. A wild-type sequence can also be referred to as a naturally occurring typical or normal sequence without modifications.

In general, this disclosure provides methods for increasing carbon flux through a reaction catalyzed by a polypeptide having a ω-transaminase activity. Also provided are enzymes, pathways, cultivation strategies, and host organisms for increased production of one or more aminated aliphatic compounds having a carbon chain length of C5-C19 or a salt thereof.

Methods of Biosynthesizing Carbon-Based Products

The present invention provides a method of enhancing biosynthesis in vivo, comprising: obtaining at least one organism capable of biosynthesizing at least one product, the at least one organism being unaltered or altered, wherein the organism utilizes a polypeptide having a ω-transaminase activity to catalyze a transamination reaction, wherein the polypeptide or a functional fragment thereof has at least 70% identity to SEQ ID NO: 1; and b) culturing the organism under conditions suitable for biosynthesis, wherein the organism biosynthesizes the at least one product, wherein the product is an aminated aliphatic compound having a carbon chain length of C5-C19 or a salt thereof.

In some embodiments, the product is an aminated aliphatic compound having a carbon chain length of C6-C7, or a salt thereof, for example, 7-AHA or 6-aminohexanoic acid or a salt thereof. In some embodiments, the product is an amino alcohol, such as 7-aminoheptanol or 6-aminohexanol or a salt thereof. In some embodiments, the product is a diamine such as heptamethylenediamine or hexamethylenediamine or a salt thereof.

In some embodiments, the transamination reaction is catalyzed by a polypeptide or functional fragment thereof having the activity of a ω-transaminase classified under EC 2.6.1.18, EC 2.6.1.19, EC 2.6.1.29, EC 2.6.1.48 or EC 2.6.1.82.

Figure 9:
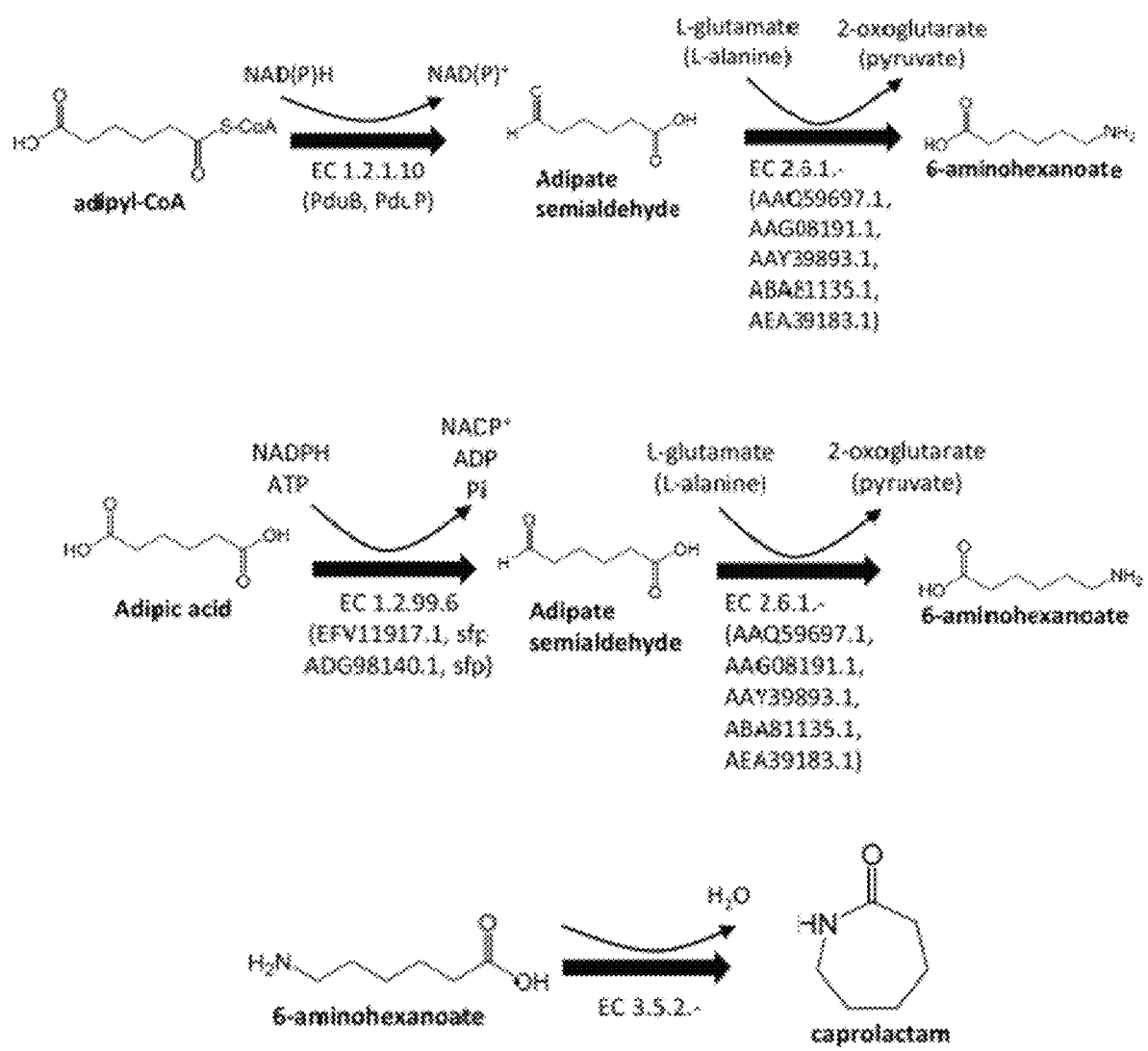
FIG. 9 is a schematic of exemplary biochemical pathways leading to 6-aminohexanoate or caprolactam using adipyl-CoA, adipate, or adipate semialdehyde as central precursors.

Any of the methods provided herein, can be performed in one or more host organisms or cells. In some embodiments, the host organism expresses one or more polypeptides having the activity of at least one enzyme in a pathway for production of an aminated aliphatic compound having a carbon chain length of C5-C19. For example, one or more polypeptides having the activity of at least one enzyme in the pathway provided in FIG. 2, for the production of 7-AHA, can be expressed by the organism. In some embodiments, one or more polypeptides having the activity of at least one enzyme in the pathway provided in FIG. 9, for the production of 6-AHA can be expressed in the organism.

The organism can (a) naturally express polypeptides having the activity of one or more relevant enzymes in a pathway, (b) be genetically engineered to express one or more polypeptides having the activity of one or more relevant enzymes in a pathway, or (c) naturally express one or more polypeptides having the activity of one or more relevant enzymes and be genetically engineered to express one or more polypeptides having the activity of one or more relevant enzymes in a pathway. The organism can also naturally express or be engineered to express one or more polypeptides that modify a product produced by the organism. In the methods provided by the disclosure, all the steps can be performed in host cells, or some of the steps can be performed in cells and others can be performed using extracted polypeptides having the activity of enzymes.

In any of the methods provided herein, the polypeptide having a ω-transaminase activity to catalyze a transamination reaction, can be a polypeptide or a functional fragment thereof that has at least 70% identity to SEQ ID NO: 1. SEQ ID NO: 1, set forth below, is the amino acid sequence of a *Chromobacterium violaceum* ω-transaminase set forth under Uniprot ID No. Q7NWG4. It is understood that any sequence identified herein by a Uniprot ID No. or a GenBank Accession No. is hereby incorporated in its entirety by reference to the Unipro ID No. or the GenBank Accession No.

SEQ ID NO: 1
MQKQRTTSQWRELDAAHHLHPFTDTASLNQAGARVMTRGEGVYLWDSEGN

KIIDGMAGLWCVNVGYGRKDFAEAARRQMEELPFYNTFFKTTHPAVVELS

SLLAEVTPAGFDRVFYTNSGSESVDTMIRMVRRYWDVQGKPEKKTLIGRW

NGYHGSTIGGASLGGMKYMHEQGDLPIPGMAHIEQPWWYKHGKDMTPDEF

GVVAARWLEEKILEIGADKVAAFVGEPIQGAGGVIVPPATYWPEIERICR

KYDVLLVADEVICGFGRTGEWFGHQHFGFQPDLFTAAKGLSSGYLPIGAV

FVGKRVAEGLIAGGDFNHGFTYSGHPVCAAVAHANVAALRDEGIVQRVKD

DIGPYMQKRWRETFSRFEHVDDVRGVGMVQAFTLVKNKAKRELFPDFGEI

GTLCRDIFFRNNLIMRACGDHIVSAPPLVMTRAEVDEMLAVAERCLEEFE

QTLKARGLA

In some embodiments, a polypeptide or a functional fragment has at least about 70%, 75%, 80%, 85%, 90%, 95%, or 100% identity to SEQ ID NO: 1. In certain embodiments, the polypeptide having a ω-transaminase activity has at least 90%, 95%, 98%, 98.1, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, or 99.9% sequence identity to SEQ ID NO: 1. In any of the methods provided herein, the polypeptide having a ω-transaminase activity can comprise, consist essentially of, or consist of an amino acid sequence has at least about 70%, 75%, 80%, 85%, 90%, 95%, or 100% identity to SEQ ID NO: 1.

As set forth above, the polypeptide can be naturally expressed by the organism or engineered to express the polypeptide having a ω-transaminase activity. In an engineered or altered organism, a nucleic acid encoding the polypeptide having a ω-transaminase activity can be introduced into the organism, for example, by transforming the organism or cell with an expression cassette comprising the nucleic acid or a vector comprising the expression cassette, which may be stably incorporated or not stably incorporated into the genome of the transformed organism.

Any nucleic acid encoding a polypeptide described herein can be stably or transiently introduced into an organism, such as a host cell, using established techniques, including, but not limited to, electroporation, calcium phosphate precipitation, liposome-mediated transfection, contact with nanowires or nanotubes, spheroplasting, PEG 1000-mediated transformation, biolistics, lithium acetate transformation, lithium chloride transformation, and the like.

For stable transformation, a subject nucleic acid will generally further include a selectable marker, e.g., any of several well-known selectable markers such as neomycin resistance, and the like.

In certain embodiments, the polypeptide or functional fragment having a ω-transaminase activity does not comprise the amino acid sequence of any of the enzymes set forth in Table 1. Table 1 provides the name of the enzyme and the GenBank Accession No.(s) for the amino acid sequence of the enzyme. Therefore, the present invention provides a method of enhancing biosynthesis in vivo, comprising: obtaining at least one organism capable of biosynthesizing at least one product, the at least one organism being unaltered or altered, wherein the organism utilizes a polypeptide having a ω-transaminase activity to catalyze a transamination reaction, wherein the polypeptide or a functional fragment thereof has at least 70% identity to SEQ ID NO: 1, wherein the polypeptide does not comprise the amino acid sequence of any of the enzymes set forth in Table 1; and b) culturing the organism under conditions suitable for biosynthesis, wherein the organism biosynthesizes the at least one product, wherein the product is an aminated aliphatic compound having a carbon chain length of C5-C19 or a salt thereof. Also provided are methods of enhancing biosynthesis in vivo wherein the organism does not utilize an enzyme having the amino acid sequence set forth in GenBank Accession No. BAK39753.1 or a mutant of the enzyme having the amino acid sequence set forth in GenBank Accession No. BAK39753.1 to catalyze a transamination reaction.

TABLE 1

| Enzyme | GenBank Accession No. |
| --- | --- |
| MULTISPECIES: aspartate aminotransferase family protein [*Chromobacterium*] | WP_011135573.1 |
| aspartate aminotransferase family protein [*Chromobacterium violaceum*] | WP_081573061.1 |
| aspartate aminotransferase family protein [*Chromobacterium violaceum*] | WP_048405256.1 |
| aspartate aminotransferase family protein [*Chromobacterium vaccinii*] | WP_046156378.1 |
| aspartate aminotransferase family protein [*Chromobacterium vaccinii*] | WP_104946997.1 |
| aspartate aminotransferase family protein [*Pseudogulbenkiania ferrooxidans*] | WP_021478068.1 |
| aspartate aminotransferase family protein [*Chromobacterium* sp. MWU14-2602] | WP_103903523.1 |
| aspartate aminotransferase family protein [*Chromobacterium* sp. ATCC 53434] | WP_101708025.1 |
| aspartate aminotransferase family protein [*Chromobacterium* sp. MWU13-2610] | WP_103321487.1 |
| MULTISPECIES: aspartate aminotransferase family protein [*Chromobacterium*] | WP_043629242.1 |
| aspartate aminotransferase family protein [*Chromobacterium amazonense*] | WP_106076402.1 |
| MULTISPECIES: aspartate aminotransferase family protein [*Chromobacterium*] | WP_043572477.1 |
| aspartate aminotransferase family protein [*Chromobacterium subtsugae*] | WP_047243213.1 |
| MULTISPECIES: aspartate aminotransferase family protein [*Chromobacterium*] | WP_047237256.1 |
| aspartate aminotransferase family protein [*Chromobacterium subtsugae*] | WP_047257673.1 |
| aspartate aminotransferase family protein [*Chromobacterium sphagni*] | WP_071116856.1 |
| aspartate aminotransferase family protein [*Xenophilus* sp. AP218F] | WP_088737038.1 |
| aspartate aminotransferase family protein [*Chromobacterium* sp. LK11] | WP_048412320.1 |
| aspartate aminotransferase family protein [*Chromobacterium* sp. LK1] | WP_048411976.1 |
| aspartate aminotransferase family protein [*Chromobacterium haemolyticum*] | OQS33371.1 |
| aspartate aminotransferase family protein [*Chromobacterium haemolyticum*] | WP_081556739.1 |
| aspartate aminotransferase family protein [*Chromobacterium haemolyticum*] | WP_043638691.1 |
| aspartate aminotransferase family protein [*Chromobacterium haemolyticum*] | OQS37730.1 |
| MULTISPECIES: aspartate aminotransferase family protein [*Chromobacterium*] | WP_019104435.1 |
| aspartate aminotransferase family protein [*Chromobacterium haemolyticum*] | OQS32233.1 |
| aspartate aminotransferase family protein [*Chromobacterium haemolyticum*] | WP_081576047.1 |
| aspartate aminotransferase family protein [*Chromobacterium haemolyticum*] | WP_043593957.1 |
| aspartate aminotransferase family protein [*Vogesella* sp. LIG4] | WP_088967522.1 |
| aspartate aminotransferase family protein [*Aquitalea magnusonii*] | WP_089085350.1 |
| aspartate aminotransferase family protein [beta proteobacterium L13] | WP_017508334.1 |
| aspartate aminotransferase family protein [*Pseudomonas* sp. MWU14-2217] | WP_103523625.1 |

TABLE 1-continued

| Enzyme | GenBank Accession No. |
|---|---|
| MULTISPECIES: aspartate aminotransferase family protein [*Aquitalea*] | WP_045848621.1 |
| aspartate aminotransferase family protein [*Aquitalea magnusonii*] | WP_059287319.1 |
| aspartate aminotransferase family protein [*Pseudogulbenkiania* sp. MAI-1] | WP_024302818.1 |
| aspartate aminotransferase family protein [*Gulbenkiania indica*] | WP_055434103.1 |
| aspartate aminotransferase family protein [*Gulbenkiania mobilis*] | WP_054286466.1 |
| aspartate aminotransferase family protein [*Pseudogulbenkiania subflava*] | WP_085275708.1 |
| aspartate aminotransferase family protein [*Pseudogulbenkiania ferrooxidans*] | WP_008952788.1 |
| aspartate aminotransferase family protein [*Pseudogulbenkiania* sp. NH8B] | WP_014087389.1 |
| aspartate aminotransferase family protein [*Paludibacterium yongneupense*] | WP_028535161.1 |
| aspartate aminotransferase family protein [*Vogesella* sp. EB] | WP_047966302.1 |
| aspartate aminotransferase family protein [*Microvirgula aerodenitrificans*] | WP_028498438.1 |
| Probable aminotransferase [*Laribacter hongkongensis* HLHK9] | ACO75192.1 |
| aspartate aminotransferase family protein [*Laribacter hongkongensis*] | WP_088861121.1 |
| aspartate aminotransferase family protein [*Laribacter hongkongensis*] | WP_041825665.1 |
| aspartate aminotransferase family protein [*Laribacter hongkongensis*] | WP_034984857.1 |
| BioA homolog [*Vitreoscilla* sp. C1] | AAD41041.1 |
| MULTISPECIES: aspartate aminotransferase family protein [*Vitreoscilla*] | WP_019957606.1 |
| aspartate aminotransferase family protein [*Neisseria shayeganii*] | WP_009118141.1 |
| aspartate aminotransferase family protein [*Stenoxybacter acetivorans*] | WP_037587322.1 |
| aspartate aminotransferase family protein [*Aquaspirillum* sp. LM1] | AQR66583.1, AQR64576.1, AQR64062.1, AQR66432.1, WP_077302460.1, WP_077297579.1, WP_077296528.1, WP_077302987.1 |

It has been discovered that altering the reaction conditions of a transamination reaction catalyzed by a polypeptide having a ω-transaminase activity increases production of certain carbon-based products, for example, aminated aliphatic compounds having a carbon chain length of C5-C19. Therefore, any of the methods provided herein can comprise a step of altering the reaction conditions of the transaminase reaction catalyzed by the polypeptide having ω-transaminase activity.

The reaction conditions of the transaminase reaction in any of the methods provided herein can be altered through one or more modes to increase ω-transamination activity of the polypeptide or fragment thereof having a ω-transaminase activity, as compared to an organism where transamination reaction conditions have not been altered. In some embodiments, reaction conditions are altered to shift the transaminase reaction equilibrium in favour of product formation. In some embodiments, altering the reaction conditions of the transamination reaction results in an increase in total product yield. In some embodiments, an increase in total product yield is an increase in the production of an aminated aliphatic compound having a carbon chain length of C5-C19, for example, an increase in the total yield of an aminated aliphatic compound having a carbon chain length of C6-C7. In some embodiments, the increase in total product yield is an increase in the total yield of 7-AHA.

In some embodiments, the increase in total product yield is at least about 10%, 20%, 30%, 40%, 50%, 60%, 70%, 80%, 90%, 100%, 200%, 300%, 400%, or 500% greater than the product yield in an organism where reaction conditions have not been altered.

In some embodiments, the step of altering the reaction conditions comprises catalyzing the reaction with a polypeptide or a functional fragment thereof having a ω-transaminase activity comprising one or more amino acid substitution(s) relative to a wild-type ω-transaminase, wherein the one or more amino acid substitution(s) are at amino acid(s) that occupy position(s) corresponding to position(s) 2, 13, 15, 16, 20, 87, 134, 288 or 345 of SEQ ID NO: 1.

In some embodiments, the polypeptide or a functional fragment thereof having a ω-transaminase activity comprises one or more amino acid substitution(s) relative to a wild-type ω-transaminase, wherein the one or more amino acid substitution(s) are at amino acid(s) that occupy position(s) corresponding to position(s) 2, 13, 15, 16, 20, 87, 134, 288 or 345 of the amino acid sequence set forth in Uniprot ID No. K2KXB1.

In some embodiments, the amino acid corresponding to position 2 is substituted with valine (V). In some embodiments, the amino acid corresponding to position 13 is substituted with serine (S). In some embodiments, the amino acid corresponding to position 15 is substituted with serine (S). In some embodiments, the amino acid corresponding to position 16 is substituted with serine (S). In some embodiments, the amino acid corresponding to position 134 is substituted with asparagine (N). In some embodiments, the amino acid corresponding to position 288 is substituted with glutamine (Q). In some embodiments, the amino acid corresponding to position 345 is substituted with arginine (R). In some embodiments, one or more substitutions are in the substrate binding site or substrate entry site of polypeptide. For example, amino acids at position 20 and/or 87 in the substrate binding site can be substituted. For example, the amino acid corresponding to position 20 is substituted with tyrosine (Y). In some embodiments, the amino acid corresponding to position 87 is substituted with glycine (G), alanine (A), serine (S) or threonine (T).

In some embodiments, the wild-type ω-transaminase is an ω-transaminase classified under EC 2.6.1.18, EC 2.6.1.19, EC 2.6.1.29, EC 2.6.1.48 or EC 2.6.1.82.

In some embodiments, the one or more amino acid substitutions are in the small binding pocket (O-pocket) and/or in the large binding pocket (P-pocket) of the polypeptide having ω-transaminase activity.

In some embodiments, the substituted or mutant polypeptide has increased enzymatic activity and/or improved substrate specificity relative to a wild-type ω-transaminase classified under EC 2.6.1.18, EC 2.6.1.19, EC 2.6.1.29, EC 2.6.1.48 or EC 2.6.1.82.

In some embodiments, the mutant polypeptide has an increase in enzymatic activity of at least 5%, 10%, 20%, 30%, 40%, 50%, 60%, 70%, 80%, 90%, 100%, 200%, 300%, 400%, or at least 500% relative to the activity of the wild-type ω-TAM.

In certain embodiments, enzymatic activity is specific activity, i.e., enzymatic activity for reaction of the mutant polypeptide with a specific substrate, for example, pimelate semialdehyde. In some embodiments, the increase in enzymatic activity results in an increase in total product yield of an aminated aliphatic compound having a carbon chain length of C5-C19 or a salt thereof, for example, 7-AHA or a salt thereof, when the polypeptide is expressed in an organism described herein.

In some embodiments, the improved substrate specificity of the mutant polypeptide, relative to the substrate specificity of the wild-type ω-TAM results in a polypeptide that can convert at least one substrate into at least one product at a $k_{cat}$ (s$^{-1}$) greater than that of the wild-type ω-TAM.

In some embodiments, the improved substrate specificity of the mutant polypeptide, relative to the activity of the wild-type ω-TAM results in a polypeptide that can convert at least one substrate into at least one product at a $K_m$ lower than that of the wild-type ω-TAM. In some embodiments, the improved substrate specificity is improved substrate specificity for pimelate semialdehyde.

In some embodiments, the mutant polypeptide has a reduced $K_m$ for an amino donor relative to the wild-type ω-transaminase. In some embodiments, the amino donor is L-alanine. In some embodiments, the $K_m$ for the amino donor, for example, L-alanine, is less than about 4 mmol·L$^{-1}$. In some embodiments, the polypeptide having a ω-transaminase activity has an increased $K_m$ for an aminated aliphatic compound having a carbon chain length of C5-C19 as an amino group donor relative to the wild-type ω-transaminase. In some embodiments, the polypeptide having a ω-transaminase activity has an increased $K_m$ for the aminated aliphatic compound that has a carbon chain length of C6-C7. In some embodiments, the polypeptide having a ω-transaminase activity has an increased $K_m$ for 7-AHA. In some embodiments, the wild-type ω-transaminase is a *Chromobacterium violaceum* ω-transaminase or a *Chromobacterium violaceum*-like ω-transaminase, for example, SEQ ID NO: 1.

In some embodiments substitution of one or more amino acid(s) corresponding to position(s) 2, 13, 15, 16, 20, 87, 134, 288 or 345 of SEQ ID NO: 1, increases enzymatic activity and/or improves substrate specificity. It is understood that any wild-type ω-TAM can be mutated with any combination of the amino acid substitutions described to obtain a polypeptide with increase enzymatic activity and/or improved substrate specificity. In some embodiments, the mutant ω-TAM comprises two or more, three or more, four or more, five or more, six or more, seven or more, or eight or more substitutions at amino acid(s) that occupy position (s) corresponding to position(s) 2, 13, 15, 16, 20, 87, 134, 288 or 345 of SEQ ID NO: 1.

As set forth above, the mutant ω-TAM can have one or more amino acid substitutions described above, relative to a wild-type ω-TAM, for example, and not to be limiting, relative to a wild-type ω-TAM classified under EC 2.6.1.18, EC 2.6.1.19, EC 2.6.1.29, EC 2.6.1.48 or EC 2.6.1.82. In some embodiments, the mutant ω-TAM has one or more additional modifications. Protein modifications include amino acid sequence modifications. Modifications in amino acid sequence may arise naturally as allelic variations (e.g., due to genetic polymorphism), may arise due to environmental influence (e.g., by exposure to ultraviolet light), or may be produced by human intervention (e.g., by mutagenesis of cloned DNA sequences), such as induced point, deletion, insertion, and substitution mutants. Modifications in a nucleic acid encoding an ω-TAM can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about 1 to 10 amino acid residues; and deletions will range from about 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Substitutional modifications are those in which at least one residue has been removed and a different residues inserted in its place. In some embodiments, conservative or equivalent substitutions are made. A conservative substitution results in substitution of an amino acid with a chemically and/or functionally similar amino acid. Modifications, including specific amino acid substitutions, are made by known methods.

By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example, PCR mutagenesis, primer extension or inverse PCR mutagenesis.

Fusion polypeptides comprising any of the polypeptides described herein are also provided. The polypeptides can be fused to heterologous sequences, for example, and not to be limiting, tags or sequences designed to facilitate expression, purification and/or detection of recombinantly-expressed proteins. Non-limiting examples include a periplasmic tag, a poly-histidine tag, a maltose binding protein (MBP), Protein A, glutathione S-transferase (GST), fluorescent protein sequences (e.g. GFP), and epitope tags such as myc, FLAG, and haemagglutinin tags.

In some embodiments, the amino acid sequence of the polypeptide having an ω-TAM activity, for example, a mutant ω-TAM has at least 70%, 75%, 80%, 85%, 90%, 95%, 99% amino acid sequence identity with the amino acid sequence of the wild-type ω-TAM, and has enzymatic activity. In certain embodiments, the amino acid sequence of the polypeptide having an ω-TAM, for example, a mutant ω-TAM has at least 90%, 95%, 98%, 98.1, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, or 99.9% sequence identity to the wild-type ω-TAM and has enzymatic activity. In certain embodiments, the enzymatic activity is specific for conversion of pimelate semialdehyde to 7-AHA.

Derivatives of any of the mutant polypeptides described herein also provided. In some embodiments, derivative polypeptides are polypeptides that have been further altered, for example by conjugation or complexing with other chemical moieties, by post-translational modification (e.g. phosphorylation, acetylation and the like), modification of glycosylation (e.g. adding, removing or altering glycosylation), and/or inclusion/substitution of additional amino acid sequences as would be understood in the art. Derivatives also include fusion proteins, as described above. Other derivatives contemplated by the embodiments include, but are not limited to, modification to side chains, incorporation of unnatural amino acids and/or their derivatives during peptide, or protein synthesis and the use of crosslinkers and other methods which impose conformational constraints on the polypeptides and fragments thereof.

In some methods, the step of altering reaction conditions comprises cyclization, for example, cyclization of the product. In certain embodiments, altering reaction conditions comprises cyclizing at least one product into a lactam, for example, cyclizing 7-AHA into heptanolactam. In some embodiments, the organism utilizes a polypeptide having *Clostridium propionicum* β-alanine CoA transferase activity to cyclize the product. In some embodiments, the polypeptide having β-alanine CoA converts 7-AHA to heptanolactam, wherein the amount of pimelate semialdehyde formed from the reverse reaction of ω-transaminase with 7-AHA is reduced. In some embodiments, the amount of pimelate semialdehyde formed from the reverse reaction of ω-transaminase with 7-AHA is reduced by at least 10%, 20%, 30%, 40%, 50%, 60%, 70%, 80%, 90% or 100%. In some embodiments, cyclization of the product removes or otherwise reduces the availability of the product for a reverse reaction catalyzed by a polypeptide having ω-transaminase activity. The reduction can be a reduction as compared to the reduction in the availability of the product in an organism that does not cyclize the product. In some embodiments, the reduction is at least 10%, 20%, 30%, 40%, 50%, 60%, 70%, 80%, 90% or 100%.

In some embodiments, the method further comprises processing the cyclized product to obtain an aminated aliphatic compound having a carbon chain length of C5-C19, for example, 7-AHA or 6-aminohexanoic acid or a salt thereof. In some embodiments, the product is an amino alcohol, such as 7-aminoheptanol or 6-aminohexanol or a salt thereof. In some embodiments, the product is a diamine such as heptamethylenediamine or hexamethylenediamine or a salt thereof.

In some embodiments, the step of altering the reaction conditions comprises increasing the level of an intracellular amino group donor in the organism. In some embodiments, the amino group donor is exogenously introduced into the organism. In some embodiments, the organism utilizes a polypeptide having L-amino acid dehydrogenase activity to increase the intracellular level of the amino group donor in the cell introduced into the organism. In some embodiments, the L-amino acid dehydrogenase is L-alanine dehydrogenase. In some embodiments, the concentration of the amino group donor is increased to a concentration from about 4-10 mmol $L^{-1}$.

In some embodiments, the step of altering the reaction conditions comprises removing or otherwise reducing availability of the product. In some embodiments, the organism utilizes a polypeptide having amino acid transporter activity to remove or otherwise reduce the availability of the product. For example, and not to be limiting, the organism can naturally express or be engineered to express one or more of the polypeptides having amino acid transporter activity provided in Table 2, to remove or otherwise reduce the availability of the product. The reduction in the availability of the product can be a reduction as compared to the reduction in the availability of the product in an organism that that does not utilize a polypeptide having amino acid transporter activity to remove or otherwise reduce the availability of the product. In some embodiments, the reduction is at least 10%, 20%, 30%, 40%, 50%, 60%, 70%, 80%, 90% or 100%

TABLE 2

| Uniprot ID | Organism | Sequence |
|---|---|---|
| amino acid transporter | | |
| P15993 | *Escherichia coli* (strain K12) | MMEGQQHGEQLKRGLKNRHIQLIALGGAIGTGLFLG SASVIQSAGPGIILGYAIAGFIAFLIMRQLGEMVVEEP VAGSFSHFAYKYWGSFAGFASGWNYWVLYVLVAM AELTAVGKYIQFWYPEIPTWVSAAVFFVVINAINLTN VKVFGEMEFWFAIIKVIAVVAMIIFGGWLLFSGNGGP QATVSNLWDQGGFLPHGFTGLVMMMAIIMFSFGGLE LVGITAAEADNPEQSIPKATNQVIYRILIFYIGSLAVLL SLMPWTRVTADTSPFVLIFHELGDTFVANALNIVVLT AALSVYNSCVYCNSRMLFGLAQQGNAPKALASVDK RGVPVNTILVSALVTALCVLINYLAPESAFGLLMALV VSALVINWAMISLAHMKFRRAKQEQGVVTRFPALLY PLGNWICLLFMAAVLVIMLMTPGMAISVYLIPVWLIV LGIGYLFKEKTAKAVKAH (SEQ ID NO: 3) |
| P94499 | *Bacillus subtilis* (strain 168) | MSKKVSASYIIIIGLMLFALFFGAGNLIFPPMLGQLAG KNVWVANAGFLVTGVGLPLLAITAFVFSGKQNLQSL ASRVHPVFGIVFTTILYLAIGPFFAIPRSGNVSFEIGVK PFLSNDA SPVSLIIFTILFFALACLLSLNPSKIIDIVGKFLTPIKLTFI GLLVAVALIRPIGTIQAPSKGYTSQAFFKGFQEGYLTL DALVAFVFGIIIVNALKEQGASTKKQLIVVCAKAAAI AAV LLAVMYTALSYMGASSVEELGILENGAEVLAKVSSY YFGSYGSILLGLMITVACLTTSVGLITACSSFFHELFPN ISYKKIAVVLSVFSTLVANIGLTQLIKVSMPVLLTMYP IAISLIF LTFLHSVFKGKIEVYQGSLLFAFIISLFDGLKAAGIKIE VVNRIFTQILPMYNIGLGWLIPAIAGGICGYILSIFRTK TS (SEQ ID NO: 4) |

TABLE 2-continued

| Uniprot ID | Organism | Sequence |
|---|---|---|
| H7C6B6 | Corynebacterium glutamicum (Brevibacterium saccharolyticum) | MLSFATLRGRISTVDAAKAAPPPSPLAPIDLTDHSQV AGVMNLAARIGDILLSSGTSNSDTKVQVRAVTSAYG LYYTHVDITLNTITIFTNIGVERKMPVNVFHVVGKLD TNFSKLSEVD RLIRSIQAGATPPEVAEKILDELEQSPASYGFPVALLG WAMMGGAVAVLLGGGWQVSLIAFITAFTIIATTSFL GKKGLPTFFQNVVGGFIATLPASIAYSLALQFGLEIKP SQIIASGI VVLLAGLTLVQSLQDGITGAPVTASARFFETLLFTGGI VAGVGLGIQLSEILHVMLPAMESAAAPNYSSTFARII AGGVTAAAFAVGCYAEWSSVIIAGLTALMGSAFYYL FVVYLGPVS AAAIAATAVGFTGGLLARRFLIPPLIVAIAGITPMLPG LAIYRGMYATLNDQTLMGFTNIAVALATASSLAAGV VLGEWIARRLRPPPRFNPYRAFTKANEFSFQEEAEQN QRRQRKRPK TNQRFGNKR (SEQ ID NO: 5) |
| P39817 | Bacillus subtilis (strain 168) | MKKLIAFQILIALAVGAVIGHFFPDFGMALRPVGDGFI RLIKMIVVPIVFSTIVIGAAGSGSMKKMGSLGIKTIIWF EVITTLVLGLGLLLANVLKPGVGLDLSHLAKKDIHEL SGYTDK VVDFKQMILDIIPTNIIDVMARNDLLAVIFFAILFGVA AAGIGKASEPVMKFFESTAQIMFKLTQIVMVTAPIGV LALMAASVGQYGIELLLPMFKLVGTVFLGLFLILFVL FPLVGLIF QIKYFEVLKMIWDLFLIAFSTTSTETILPQLMDRMEK YGCPKRVVSFVVPSGLSLNCDGSSLYLSVSCIFLAQA FQVDMTLSQQLLMMLVLVMTSKGIAAVPSGSLVVLL ATANAVGLPA EGVAIIAGVDRVMDMARTGVNVPGHAIACIVVSKWE KAFRQKEWVSANSQTESI (SEQ ID NO: 6) |
| P35865 | Corynebacterium glutamicum (strain ATCC 13032/DSM 20300/JCM 1318/LMG 3730/NCIMB 10025) | MNTQSDSAGSQGAAATSRTVSIRTLIALIIGSTVGAGI FSIPQNIGSVAGPGAMLIGWLIAGVGMLSVAFVFHVL ARRKPHLDSGVYAYARVGLGDYVGFSSAWGYWLG SVIAQVGYATL FFSTLGHYVPLFSQDHPFVSALAVSALTWLVFGVVSR GISQAAFLTTVTTVAKILPLLCFIILVAFLGFSWEKFTV DLWARDGGVGSIFDQVRGIMVYTVWVFIGIEGASVY SRQARSRS DVSRATVIGFVAVLLLLVSISSLSFGVLTQQELAALPD NSMASVLEAVVGPWGAALISLGLCLSVLGAYVSWQ MLCAEPLALMAMDGLIPSKIGAINSRGAAWMAQLIS TIVIQIFIIIF FLNETTYVSMVQLATNLYLVPYLFSAFYLVMLATRG KGITHPHAGTRFDDSGPEISRRENRKHLIVGLVATVY SVWLFYAAEPQFVLFGAMAMLPGLIPYVWTRIYRGE QVFNRFEIGVV VVLVVAASAGVIGLVNGSLSL (SEQ ID NO: 7) |
| Fatty acyl-CoA reductase (FAR) | | |
| W5YTA4 | Marinobacter salarius | MATQQQQNGASASGVLEQLRGKHVLITGTTGFLGK VVLEKLIRTVPDIGGIHLLIRGNKRHPAARERFLNEIA SSSVFERLRHDDNEAFESFLEERVHCITGEVTEPRFGL TQERFRALA GQVDAFINSAASVNFREELDKALKINTLCLENVAALA ELNSTMAVIQVSTCYVNGKNSGQITESVIKPAGESIPR SADGYYETEELVHLLQDKISDVKARYSGKVLEKKLV DLGIREANN YGWSDTYTFTKWLGEQLLMKALSGRSLTIVRPSIIES ALEEPSPGWIEGVKVADAIILAYAREKVSLFPGKRSGI IDVIPVDLVANSIILSLAEAISEPGHRRIYQCCSGGSNPI SLGTF IDYLMAEAKSNYAAYDQLFYRRPTKPFVAVNRKLFD VVVGGMRVPLSIAGKALRLAGQNRELKVLKNLDTT RSLATIFGFYTAPDYIFRNDSLMALASRMGELDRVLF PVDARQIDWQLY LCKIHLGGLNRYALKERKLYSLRAAQTRKKAA (SEQ ID NO: 8) |
| R8AYU1 | Marinobacter lipolyticus SA19 | MVQQLQTSELSSTVLEQLRGKHVLVTGTTGFLGKVV LEKLIRAVPDIGGIHLLIRGNKRHPNARERFFHEIATSS VFERLRQEDNEAFEAFIEERVHCITGEVTKPRFGLTPE RFTTLAN QADAFINSAASVNFREELDKALTINTLCLNNVVELAR RNRKMAVIQVSTCYVNGKNSGQVTESVIKPAGESIPR |

TABLE 2-continued

| Uniprot ID | Organism | Sequence |
|---|---|---|
| | | STAGYYEIEELVRLLEDKIADVRSRYSGKVLEKKLVD<br>LGIQEANRY<br>GWSDTYTFTKWLGEQLLMKALDQRALTIVRPSIIESA<br>LEEPAPGWIEGVKVADAIILAYAREKVTLFPGKRSGII<br>DVIPVDLVANAIILSLAEALAEAPQRRIYQCCSGSSNPI<br>SLGEFI<br>DHLMAESKANYAAYDQLFYRQPSKPFIAVNRKLFDA<br>VVGGMRVPLSLTSRVMRMLGQNRELKTLRNLDTSR<br>SLATIFGFYTAPDYIFRNDSLQALASRMGERDQALFP<br>VDARRIDWSLYL<br>RKIHLAGLNQYALKERKLYSLRSAKARKQAA<br>(SEQ ID NO: 9) |

In some embodiments, the polypeptide having amino acid transporter activity has LysE amino acid transporter activity.

In some embodiments, the organism utilizes a polypeptide having amino acid transporter activity to reduce the amount of at least one product formed from a reverse reaction of the polypeptide having a ω-transaminase activity and an aminated aliphatic compound having a carbon chain length of C5-C19. In some embodiments, the amount of pimelate semialdehyde formed from the reverse reaction of ω-transaminase with 7-AHA is reduced when the organism utilizes a polypeptide having amino acid transporter activity.

In some embodiments, the step of altering the reaction conditions comprises using an amino donor which forms a volatile product and drives the transamination reaction towards product formation. In an embodiment, the volatile product may be isopropylamine.

As described above, any of the methods provided herein can comprise the step of altering the reaction conditions of the transamination reaction catalyzed by any of the polypeptides having a ω-TAM activity described herein, including wild-type ω-TAMs and modified ω-TAMs.

In some embodiments, altering the reaction conditions comprises increasing the amount of an intracellular amino group donor, cyclizing the product, using isopropylamine or an equivalent compound to drive the transamination reaction towards product formation, and/or removing the product from the cell.

In some embodiments, altering the reaction conditions comprises increasing the amount of an intracellular amino group donor and cyclizing the product.

In some embodiments, altering the reaction conditions comprises increasing the amount of an intracellular amino group donor and removing the product from the cell.

In some embodiments, altering the reaction conditions comprises increasing the amount of an intracellular amino donor, cyclizing the product, using isopropylamine or an equivalent compound to drive the transamination reaction towards product formation, and removing the product from the cell.

In some embodiments, the method further comprises purifying the product.

In some embodiments, the organism is a prokaryote. For example, the prokaryote can be from the bacterial genus *Escherichia* such as *Escherichia coli*; from the bacterial genus *Clostridia*, such as *Clostridium ljungdahlii*, *Clostridium autoethanogenum* or *Clostridium kluyveri*; from the bacterial genus *Corynebacteria*, such as *Corynebacterium glutamicum*; from the bacterial genus *Cupriavidus*, such as *Cupriavidus necator* or *Cupriavidus metallidurans*; from the bacterial genus *Pseudomonas*, such as *Pseudomonas fluorescens*, *Pseudomonas putida* or *Pseudomonas oleavorans*; from the bacterial genus *Delftia* such as *Delftia acidovorans*; from the bacterial genus *Bacillus* such as *Bacillus subtillis*; from the bacterial genus *Lactobacillus*, such as *Lactobacillus delbrueckii*; or from the bacterial genus *Lactococcus*, such as *Lactococcus lactis*.

In some embodiments, the organism is a eukaryote (e.g., a fungus such as a yeast). For example, the eukaryote can be from the fungus genus *Aspergillus* such as *Aspergillus niger*; from the yeast genus *Saccharomyces*, such as *Saccharomyces cerevisiae*; from the yeast genus *Pichia* such as *Pichia pastoris*; from the yeast genus *Yarrowia* such as *Yarrowia hpolytica*; from the yeast genus *Issatchenkia*, such as *Issathenkia orientalis*; from the yeast genus *Debaryomyces* such as *Debaryomyces hansenii*; from the yeast genus *Arxula* such as *Arxula adenoinivorans*; or from the yeast genus *Kluyveromyces* such as *Kluyveromyces lactis*.

Exemplary species of yeast or fungi species include any species selected from the order Saccharomycetales, family Saccaromycetaceae, including the genera *Saccharomyces*, *Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae*, *Schizosaccharomyces pombe*, *Kluyveromyces lactis*, *Kluyveromyces marxianus*, *Aspergillus terreus*, *Aspergillus niger*, *Pichia pastoris*, *Rhizopus arrhizus*, *Rhizopus oryzae*, *Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

In some embodiments, the organism is a recombinant organism. In some embodiments, the recombinant organism comprises at least one exogenous nucleic acid encoding at least one polypeptide having the activity of at least one enzyme depicted in FIG. 2. In some embodiments, the polypeptide having the activity of at least one enzyme depicted in FIG. 2 has the activity of a a ω-transaminase, a thioesterase or carboxylate reductase.

For example, a polypeptide having thioesterase (TE) activity described herein can have at least 70% sequence identity (e.g., at least 75%, 80%, 85%, 90%, 95%, 97%, 98%, 99%, or 100%) to the amino acid sequence of an *Escherichia coli* thioesterase encoded by tesB (see GenBank Accession No. AAA24665.1) or the gene products encoded by tesA or fatB (see GenBank Accession No. ABJ63754.1 and GenBank Accession No. CCC78182.1, respectively). In some embodiments, the polypeptide having thioesterase activity is classified under EC 3.1.2.- at least 70% sequence identity (e.g., at least 75%, 80%, 85%, 90%, 95%, 97%, 98%, 99%, or 100%) to an enzyme classified under EC 3.1.2.-. In some embodiments, the polypeptide having thioesterase activity is classified under 3.1.2.14, EC 3.1.1.1, EC 3.1.1.2, or EC 3.1.1.5.

In some embodiments, a polypeptide having carboxylate reductase activity described herein can have at least 70% sequence identity (e.g., at least 75%, 80%, 85%, 90%, 95%, 97%, 98%, 99%, or 100%) to the amino acid sequence of a *Mycobacterium marinum* (see Genbank Accession No. ACC40567.1), a *Mycobacterium smegmatis* (see Genbank Accession No. ABK71854.1), a *Segniliparus rugosus* (see Genbank Accession No. EFV11917.1), a *Mycobacterium smegmatis* (see Genbank Accession No. ABK75684.1), a *Mycobacterium massiliense* (see Genbank Accession No. EIV11143.1) or a *Segniliparus rotundus* (see Genbank Accession No. ADG98140.1) carboxylate reductase. In some embodiments, a polypeptide having carboxylate described herein is classified, for example, under EC 1.2.99.6. In other embodiments, a polypeptide having carboxylate described herein can have at least 70% sequence identity (e.g., at least 75%, 80%, 85%, 90%, 95%, 97%, 98%, 99%, or 100%) to the amino acid sequence of a carboxylate reductase classified under EC 1.2.99.66.

In some embodiments, a polypeptide having the activity of a carboxylate reductase may be the gene product of car (e.g., a *Mycobacterium marinum* carboxylate reductase (see UniProtKB Accession No. B2HN69) or a *Nocardia iowensis* carboxylate reductase (see UniProtKB Accession No. Q6RKB1). In some embodiments, a polypeptide having the activity of carboxylate reductase is the gene product of fadD9 (e.g., *Mycobacterium smegmatis* fatty-acid-CoA ligase (see UniProtKB Accession No. A0QWI7) or *Mycobacterium smegmatis* fatty-acid-CoA ligase (see UniProtKB Accession No. A0A0D6J1A6).

In some embodiments, a carboxylate reductase may be selected from: a *Mycobacterium smegmatis* carboxylate reductase (see UniProtKB Accession No. A0R484); a *Mycobacterium avium* carboxylate reductase (see GenBank Accession No. WP_019730046.1); a *Segnihparus rugosus* carboxylate reductase (see UniProtKB Accession No. E5XUS9); a *Mycobacterium* sp. JS623 carboxylate reductase (see UniProtKB Accession No. LOIYJ8); a *Mycobacterium heckeshornense* carboxylate reductase (see UniProtKB Accession No. A0A0J8X8T4); a *Mycobacterium goodii I* carboxylate reductase (see UniProtKB Accession No. A0A0K0XCM7); a *Mycobacterium goodii* carboxylate reductase (see UniProtKB Accession No. A0A0K0X557); a *Mycobacterium intracellulare* carboxylate reductase (see UniProtKB Accession No. H8ITF4; a *Mycobacterium massiliense* carboxylate reductase (see Genbank Accession No. EIV11143.1); a *Segniliparus rotundus* (see Genbank Accession No. D6Z860); and a *Segniliparus rotundus* (see UniProtKB Accession No. D6ZDT1).

In some embodiments, a carboxylate reductase may be selected from: a *Mycobacterium smegmatis* carboxylate reductase (see UniProtKB Accession No. A0R484); a *Mycobacterium avium* carboxylate reductase (see GenBank Accession No. WP_019730046.1); and a *Segniliparus rugosus* carboxylate reductase (see UniProtKB Accession No. E5XUS9).

In some embodiments, a carboxylate reductase may be selected from: a *Mycobacterium* sp. JS623 carboxylate reductase (see UniProtKB Accession No. LOIYJ8); a *Mycobacterium heckeshornense* carboxylate reductase (see UniProtKB Accession No. A0A0J8X8T); a *Mycobacterium goodii I* (see UniProtKB Accession No. A0A0K0XCM7); a *Mycobacterium goodii* carboxylate reductase (see UniProtKB Accession No. A0A0K0X557); a *Mycobacterium intracellulare I* (see UniProtKB Accession No. H8ITF4); and a *Mycobacterium* smegmatis fatty-acid-CoA ligase (see UniProtKB Accession No. A0A0D6J1A6).

In some embodiments, a polypeptide having a ω-transaminase activity can have at least 70% sequence identity (e.g., at least 750%, 80%, 85%, 90%, 95%, 97%, 98%, 99%, or 100%) to the amino acid sequence of a *Chromobacterium violaceum* ω-transaminase (see Genbank Accession No. AAQ59697.1; Uniprot ID No. Q7NWG4 (SEQ ID NO: 1)).

In some embodiments, the recombinant organism comprises an exogenous nucleic acid encoding an L-amino acid dehydrogenase, for example, a L-alanine dehydrogenase.

In some embodiments, the recombinant organism overexpresses one or more genes encoding: an acetyl-CoA synthetase, a β-alanine CoA transferase, a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter, a dicarboxylate transporter, an amino acid transporter, and/or a multidrug transporter. In some embodiments, the recombinant organism overexpresses a gene encoding an amino acid transporter, for example, any of the amino acid transporters set forth in Table 2. In some embodiments, the amino acid transporter is a LysE transporter.

In some embodiments, the recombinant organism produces an increased level of 7-AHA converted from pimelic acid or pimelic acid derivatives, as compared to a wild-type organism. In some embodiments, the pimelic acid derivatives comprise pimelyl-ACP and pimelate semialdehyde. In some embodiments, the pimelate semialdehyde is transaminated to produce 7-AHA. In some embodiments, the recombinant organism comprises a nucleic acid encoding a polypeptide having *Clostridium propionicum* β-alanine CoA transferase activity, wherein the polypeptide cyclizes the product. In some embodiments, the polypeptide having β-alanine CoA converts 7-AHA to heptanolactam, thereby decreasing the amount of pimelate semialdehyde formed from the reverse reaction of ω-transaminase with 7-AHA.

In some embodiments, the organism can be subjected to a cultivation strategy under aerobic, anaerobic, micro-aerobic or mixed oxygen/denitrification cultivation conditions. The organism can be cultured under conditions of nutrient limitation. The organism can be retained using a ceramic hollow fiber membrane to maintain a high cell density during fermentation.

The principal carbon source fed to the fermentation can derive from biological or non-biological feedstocks. In some embodiments, the biological feedstock is, includes, or derives from, at least one chosen from monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the non-biological feedstock is, or derives from, at least one chosen from natural gas, syngas, $CO_2/H_2$, methanol, ethanol, benzoate, non-volatile residue (NVR) or a caustic wash waste stream from cyclohexane oxidation processes, or a terephthalic acid/isophthalic acid mixture waste stream.

In any of the methods, the organism's tolerance to high concentrations of at least one product, for example, an aminated aliphatic compound having a carbon chain length of C5-C19 can be improved through continuous cultivation in a selective environment.

In any of the methods provided herein, one or more products can be produced by providing an organism, for example, any recombinant organism described herein, and culturing the provided organism with a culture medium containing a suitable carbon source as described above. In general, the culture media and/or culture conditions can be such that the microorganisms grow to an adequate density and produce at least one aminated aliphatic compound having a carbon chain length of C5-C19 efficiently. For large-scale production processes, any method can be used such as those described elsewhere (Manual of Industrial Microbiology and Biotechnology, 2nd Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular organism. After inoculation, the organism is incubated to allow biomass to be produced. Once a desired biomass is reached, the broth containing the organisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the organisms can be incubated to allow for the production of an aminated aliphatic compound having a carbon chain length of C5-C19. Once produced, any method can be used to isolate aminated aliphatic compounds having a carbon chain length of C5-C19. For example, aminated aliphatic compounds having a carbon chain length of C5-C19 can be recovered selectively from the fermentation broth via adsorption processes. In the case of 7-AHA, the resulting eluate can be further concentrated via evaporation, crystallized via evaporative and/or cooling crystallization, and the crystals recovered via centrifugation.

Recombinant Organisms

In another embodiment, provided herein is a recombinant organism comprising an exogenous nucleic acid encoding a polypeptide having w transaminase activity, wherein the polypeptide or a functional fragment thereof has at least 70% identity to SEQ ID NO: 1, and wherein the recombinant organism produces an increased level of an aminated aliphatic compound having a carbon chain length of C5-C19 as compared to a wild-type organism. In some embodiments, the recombinant organism is prokaryotic. In some embodiments, the recombinant organism is eukaryotic.

In some embodiments, the aminated aliphatic compound produced by the recombinant organism has a carbon chain length of C6-C7. In some embodiments, the aminated aliphatic compound produced by the recombinant organism is 7-AHA. In some embodiments, the exogenous nucleic acid encodes a polypeptide having ω-transaminase activity comprising one or more amino acid substitution(s) relative to a wild-type ω-transaminase, wherein the one or more amino acid substitution(s) are at amino acid(s) that occupy position(s) corresponding to position(s) 2, 13, 15, 16, 20, 87, 134, 288 or 345 of SEQ ID NO: 1, or a functional fragment thereof.

Figure 2:
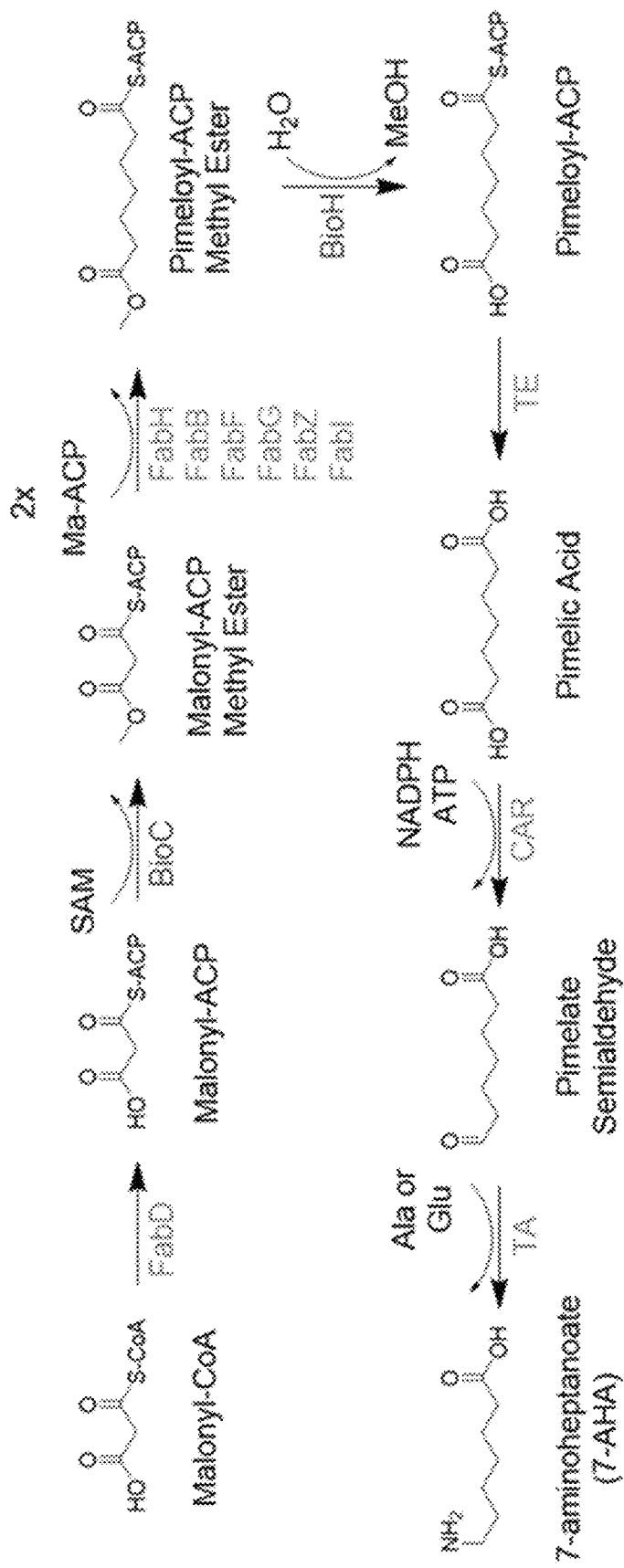
FIG. 2 is a schematic of an exemplary biochemical pathway for producing 7-AHA from malonyl-CoA.

In some embodiments, the recombinant organism comprises at least one exogenous nucleic acid encoding at least one polypeptide having the activity of at least one enzyme depicted in FIG. 2. In some embodiments, the recombinant organism comprises at least one exogenous nucleic acid encoding at least one polypeptide having ω-transaminase, thioesterase activity or carboxylate reductase activity. In some embodiments, the recombinant organism further comprises an exogenous nucleic acid encoding an L-amino acid dehydrogenase. In some embodiments, the L-amino acid dehydrogenase is L-alanine dehydrogenase. In some embodiments, the recombinant organism overexpresses one or more genes encoding: an acetyl-CoA synthetase; a β-alanine CoA transferase; a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; an amino acid transporter; and/or a multidrug transporter. In some embodiments, the recombinant organism overexpresses a gene encoding an amino acid transporter. In certain embodiments, the recombinant organism overexpresses a gene encoding a LysE transporter.

Any of the nucleic acids described herein can be introduced into the organism, for example, by transforming the organism or cell with an expression cassette comprising the nucleic acid or a vector comprising the expression cassette, which may be stably incorporated or not stably incorporated into the genome of the transformed organism using established techniques, described above.

Any of the recombinant organisms provided herein can be cultured using the methods described above to produce an aminated aliphatic compound having a carbon chain length of C5-C19.

Methods of Biosynthesizing Caprolactam

In another embodiment, provided herein is a method of increasing production of caprolactam comprising: culturing a host organism comprising (i) a nucleic acid encoding a polypeptide having ω-transaminase activity or a functional fragment thereof, wherein the polypeptide has at least 70% identity to SEQ ID NO: 1; and (ii) a nucleic acid encoding a polypeptide having the activity of a β-alanine CoA transferase in the presence of a suitable substrate or metabolic intermediate and under conditions suitable for the conversion of adipic acid or adipic acid derivatives to caprolactam; and purifying the caprolactam.

In some embodiments, the polypeptide having ω-transaminase activity or a functional fragment thereof has one or more amino acid substitution(s) relative to a wild-type ω-transaminase, wherein the one or more amino acid substitution(s) are at amino acid(s) that occupy position(s) corresponding to position(s) 2, 13, 15, 16, 20, 87, 134, 288 or 345 of SEQ ID NO: 1 of SEQ ID NO: 1, or a functional fragment thereof. In some embodiments, the polypeptide having the activity of a β-alanine CoA transferase converts 6-AHA to caprolactam, wherein the amount of adipic acid semialdehyde formed from the reverse reaction of ω-transaminase with 6-AHA is thereby reduced.

In some embodiments, the polypeptide having a ω-transaminase activity or a functional fragment thereof has the activity of a ω-transaminase classified under EC 2.6.1.18, EC 2.6.1.19, EC 2.6.1.29, EC 2.6.1.48 or EC 2.6.1.82.

In some embodiments, the adipic acid derivatives comprise adipoyl-ACP and adipic acid semialdehyde. In some embodiments, the adipic acid semialdehyde is transaminated to produce 6-AHA. In some embodiments, the host organism is recombinant. In some embodiments, the host organism comprises at least one exogenous nucleic acid encoding at least one polypeptide having the activity of at least one enzyme depicted in FIG. 9.

In some embodiments, the host organism is engineered to increase intracellular levels of adipic acid and/or acetyl CoA.

Any of the culturing methods described above can be used in the methods for producing caprolactam.

Products

Figure 3:
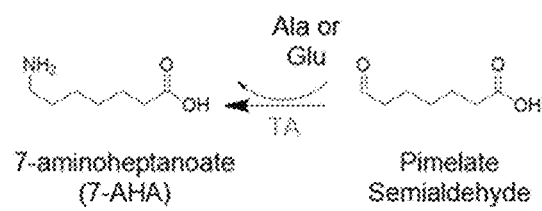
FIG. 3 is a schematic of an exemplary transamination reaction.

Other embodiments relate to bioderived or fermentation derived products produced by the methods disclosed herein, for example, a bioderived aminated aliphatic compound having a carbon chain length of C5-C19, such as, for example, 7-AHA. Other biodervied or fermentation derived products produced by the methods disclosed herein include, but are not limited to, products of the pathway depicted in FIG. 3, products of the pathway depicted in FIG. 9, heptanolactam or caprolactam. In related embodiments, products comprising a chemical produced from any of the bioderived products produced using the methods disclosed herein are also provided. In some embodiments, the product comprises a nylon intermediate, a polyester, a pharmaceutical, a biofuel, a fragrance or a food additive.

Other embodiments include a bio-based or fermentation-derived product, wherein said product comprises: i. a composition comprising at least one bio-derived, bio-based or fermentation-derived compound, or salts thereof, produced or biosynthesized according to any one of the methods provided herein; ii. a bio-derived, bio-based or fermentation-derived polymer comprising the bio-derived, bio-based or fermentation-derived composition or compound of i., or any combination thereof; iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof; iv. a substance obtained by molding the bio-derived, bio-based or fermentation-derived polymer of ii. or the bio-derived, bio-based or fermentation-derived resin of iii., or any combination thereof; v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, bio-based or fermentation-derived substance of iv, or any combination thereof; or vi. a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

Compositions

Some embodiments relate to compositions comprising one or more disclosed polypeptides or nucleic acids encoding the polypeptides described herein. In some embodiments, the composition comprises one or more disclosed polypeptides with improved enzymatic activity and/or substrate specificity. In some embodiments, the composition comprises one or more polypeptides with improved specific activity for the conversion of pimelate semialdehyde to 7-AHA.

In some embodiments the composition is composed of one or more disclosed polypeptides, from (1) commercial suppliers; (2) cloned genes expressing said polypeptides; (3) complex broth (such as that resulting from growth of a microbial strain or any other host cell in media, wherein the strains/host cells secrete the disclosed polypeptides into the media; (4) cell lysates of strains/host cells grown as in (3); and/or (5) any other host cell material expressing the disclosed polypeptide. Different disclosed polypeptides in a composition may be obtained from different sources.

Embodiments

The following embodiments are contemplated. All combinations of features and embodiment are contemplated.

Embodiment 1: A method for improved biosynthesis of an aminated aliphatic compound, the method comprising: a) providing a recombinant organism capable of biosynthesizing an aminated aliphatic compound; wherein the recombinant organism has been engineered to comprise one or more exogenous, modified, or overexpressed polypeptides; wherein each of the one or more polypeptides independently encodes at least one enzyme of an aminated aliphatic compound biosynthesis or export pathway; and wherein at least one of the one or more polypeptides encodes an ω-transaminase having at least 70% identity to SEQ ID NO: 1, or a functional fragment thereof; and b) culturing the recombinant organism under conditions suitable for the recombinant organism to produce the aminated aliphatic compound or a salt thereof.

Embodiment 2: An embodiment of embodiment 1, wherein the recombinant organism has been engineered to comprise two or more exogenous, modified, or overexpressed polypeptides; and wherein the two or more polypeptides each independently encode at least one enzyme selected from the group consisting of an ω-transaminase, a thioesterase, a carboxylate reductase, an acetyl-CoA synthetase, a β-alanine CoA transferase, a 6-phosphogluconate dehydrogenase, a transketolase, a puridine nucleotide tranyshydrogenase, a glyceraldehyde-3P-dehydrogenase, a malic enzyme, a glucose-6-phosphate dehydrogenase, a glucose dehydrogenase, a fructose 1,6 diphosphatase, an L-alanine dehydrogenase, a L-glutamate dehydrogenase, a formate dehydrogenase, an L-glutamine synthetase, a diamine transporter, a dicarboxylate transporter, an amino acid transporter, and a multidrug transporter.

Embodiment 3: An embodiment of embodiment 1 or 2, wherein the aminated aliphatic compound has a carbon chain length of C5-C19.

Embodiment 4: An embodiment of embodiment 3, wherein the aminated aliphatic compound has a carbon chain length of C6-C7.

Embodiment 5: An embodiment of embodiment 4, wherein the aminated aliphatic compound is 7-aminoheptanoic acid (7-AHA).

Embodiment 6: An embodiment of embodiment 5, wherein the recombinant organism produces 7-AHA is from pimelic acid or one or more derivatives thereof.

Embodiment 7: An embodiment of embodiment 6, wherein the one or more pimelic acid derivatives comprise pimelate semialdehyde, 1,7-heptanediol, 7-hydroxyheptanoic acid, or 7-hydroxyheptanal.

Embodiment 8: An embodiment of embodiment 7, wherein the production of 7-AHA comprises transamination of pimelate semialdehyde.

Embodiment 9: An embodiment of embodiment 4, wherein the aminated aliphatic compound is 6-aminohexanoic acid (6-AHA).

Embodiment 10: An embodiment of embodiment 4, wherein the aminated aliphatic compound is an aliphatic amino alcohol.

Embodiment 11: An embodiment of embodiment 10, wherein the aliphatic amino alcohol is 7-aminoheptanol.

Embodiment 12: An embodiment of embodiment 10, wherein the aliphatic amino alcohol is 6-aminoheptanol.

Embodiment 13: An embodiment of embodiment 4, wherein the aminated aliphatic compound is a diamine.

Embodiment 14: An embodiment of embodiment 13, wherein the diamine is heptamethylenediamine.

Embodiment 15: An embodiment of embodiment 13, wherein the diamine is hexamethylenediamine.

Embodiment 16: An embodiment of any of the embodiments of embodiment 1-15, wherein the ω-transaminase is classified under EC 2.6.1.18, EC 2.6.1.19, EC 2.6.1.29, EC 2.6.1.48, or EC 2.6.1.82.

Embodiment 17: An embodiment of any of the embodiments of embodiment 1-16, wherein the recombinant organism has increased ω-transaminase activity as compared to that of a corresponding organism not engineered to comprise the one or more exogenous, modified, or overexpressed polypeptides.

Embodiment 18: An embodiment of any of the embodiments of embodiment 1-17, wherein the recombinant organism produces the aminated aliphatic compound or a salt thereof at a higher yield as compared to that of a corresponding organism not engineered to comprise the one or more exogenous, modified, or overexpressed polypeptides.

Embodiment 19: An embodiment of any of the embodiments of embodiment 1-18, wherein at least one of the one or more polypeptides encodes a modified ω-transaminase having one or more amino acid substitutions relative to a wild-type ω-transaminase, and wherein the substitutions are at positions 2, 13, 15, 16, 20, 87, 134, 288, or 345 of SEQ ID NO: 1.

Embodiment 20: An embodiment of embodiment 19, wherein the one or more amino acid substitutions are in the small binding pocket (O-pocket) and/or in the large binding pocket (P-pocket) of the at least one polypeptide encoding the modified ω-transaminase.

Embodiment 21: An embodiment of embodiment 19 or 20, wherein the modified ω-transaminase has enhanced amination rate towards a target aliphatic aldehyde and/or improved substrate specificity towards the target aliphatic aldehyde relative to the wild-type ω-transaminase.

Embodiment 22: An embodiment of any of the embodiments of embodiment 19-21, wherein the wild-type ω-transaminase has at least 70% sequence identity with a *Chromobacterium violaceum* ω-transaminase.

Embodiment 23: An embodiment of any of the embodiments of embodiment 19-22, wherein the modified ω-transaminase has at least 10% greater activity relative to the wild-type ω-transaminase.

Embodiment 24: An embodiment of any of the embodiments of embodiment 19-23, wherein the modified ω-transaminase has a reduced $K_m$ for an amino donor relative to that of the wild-type ω-transaminase.

Embodiment 25: An embodiment of embodiment 24, wherein the amino donor is L-alanine.

Embodiment 26: An embodiment of embodiment 24 or 25, wherein the modified ω-transaminase has a $K_m$ of less than 4 mmol·$L^{-1}$ for the amino donor.

Embodiment 27: An embodiment of embodiment 19-26, wherein the modified ω-transaminase has an increased $K_m$ for the aminated aliphatic compound relative to that of the wild-type ω-transaminase.

Embodiment 28: An embodiment of any of the embodiments of embodiment 1-27, wherein at least one of the one or more peptides encodes a cyclizing enzyme capable of catalyzing a conversion of the aminated aliphatic compound to a lactam.

Embodiment 29: An embodiment of embodiment 28, wherein the cyclizing enzyme has at least 70% sequence identity with a *Clostridium propionicum* β-alanine CoA transferase.

Embodiment 30: An embodiment of embodiment 28 or 29, wherein the cyclizing enzyme is capable of catalyzing a conversion of 7-AHA to heptanolactam.

Embodiment 31: An embodiment of any of the embodiments of embodiment 1-30, wherein the culturing comprises introducing to the recombinant organism an amino group donor that is a precursor of the aminated aliphatic compound.

Embodiment 32: An embodiment of embodiment 31, wherein the aminated aliphatic compound is volatile under microbial fermentation conditions at atmospheric pressure and at a temperature from 20° C. to 65° C.

Embodiment 33: An embodiment of embodiment 32, wherein the amino group donor comprises isopropylamine.

Embodiment 34: An embodiment of any of the embodiments of embodiment 1-30, wherein at least one of the one or more polypeptides encodes an amino donor synthesis enzyme capable of catalyzing a synthesis of an amino group donor that is a precursor of the animated aliphatic compound.

Embodiment 35: An embodiment of embodiment 32, wherein the amino donor synthesis enzyme is an L-amino acid dehydrogenase.

Embodiment 36: An embodiment of embodiment 35, wherein the amino donor synthesis enzyme is L-alanine dehydrogenase.

Embodiment 37: An embodiment of any of the embodiments of embodiment 1-36, wherein at least one of the one or more polypeptides encodes an amino acid transporter capable of catalyzing an export of the aminated aliphatic compound from the organism.

Embodiment 38: An embodiment of embodiment 37, wherein the transporter is a lysine exporter.

Embodiment 39: An embodiment of any of the embodiments of embodiment 1-38, wherein the amount of at least one product formed from the aminated aliphatic compound in a reverse reaction catalyzed by the ω-transaminase is reduced as compared to that of a corresponding organism not engineered to comprise the one or more exogenous, modified, or overexpressed polypeptides.

Embodiment 40: An embodiment of embodiment 39, wherein the at least one product comprises pimelate semialdehyde, and wherein the aminated aliphatic compound is 7-AHA.

Embodiment 41: An embodiment of any of the embodiments of embodiment 1-40, further comprising: purifying the aminated aliphatic compound.

Embodiment 42: An embodiment of any of the embodiments of embodiment 1-41, wherein the recombinant organism is prokaryotic.

Embodiment 43: An embodiment of any of the embodiments of embodiment 1-41, wherein the recombinant organism is eukaryotic.

Embodiment 44: An embodiment of any of the embodiments of embodiment 1-43, wherein the culturing is in aerobic conditions.

Embodiment 45: An embodiment of any of the embodiments of embodiment 1-43, wherein the culturing is in anaerobic conditions.

Embodiment 46: An embodiment of any of the embodiments of embodiment 1-43, wherein the culturing is in micro-aerobic conditions.

Embodiment 47: An embodiment of any of the embodiments of embodiment 1-46, wherein the culturing is in conditions of nitrogen, phosphate, carbon, or oxygen nutrient limitation.

Embodiment 48: An embodiment of any of the embodiments of embodiment 1-47, wherein the culturing comprises introducing to the recombinant organism a carbon source derived from a biological feedstock.

Embodiment 49: An embodiment of any of the embodiments of embodiment 1-47, wherein the culturing comprises introducing to the recombinant organism a carbon source derived from a non-biological feedstock.

Embodiment 50: An embodiment of any of the embodiments of embodiment 1-49, further comprising: improving the tolerance of the recombinant organism through a process of directed evolution and continuous cultivation in a selective environment having increasing concentrations of the aminated aliphatic compound.

Embodiment 51: A method for improved biosynthesis of an aminated aliphatic compound, the method comprising: a) providing an organism capable of biosynthesizing an aminated aliphatic compound, wherein the organism comprises at least one polypeptide encoding an ω-transaminase having at least 70% identity to SEQ ID NO: 1, or a functional fragment thereof; and b) culturing the recombinant organism under conditions suitable for the recombinant organism to produce the aminated aliphatic compound or a salt thereof, wherein the culturing comprises introducing to the recombinant organism an amino group donor that is a precursor of the aminated aliphatic compound.

Embodiment 52: An embodiment of embodiment 51, wherein the aminated aliphatic compound is volatile under microbial fermentation conditions at atmospheric pressure and at a temperature from 20° C. to 65° C.

Embodiment 53: An embodiment of embodiment 52, wherein the amino group donor comprises isopropylamine.

Embodiment 54: An embodiment of any of the embodiments of embodiment 51-53, wherein the aminated aliphatic compound has a carbon chain length of C5-C19.

Embodiment 55: An embodiment of embodiment 54, wherein the aminated aliphatic compound has a carbon chain length of C6-C7.

Embodiment 56: An embodiment of embodiment 55, wherein the aminated aliphatic compound is 7-aminoheptanoic acid (7-AHA).

Embodiment 57: An embodiment of embodiment 56, wherein the recombinant organism produces 7-AHA is from pimelic acid or one or more derivatives thereof.

Embodiment 58: An embodiment of embodiment 57, wherein the one or more pimelic acid derivatives comprise pimelate semialdehyde, 1,7-heptanediol, 7-hydroxyheptanoic acid, or 7-hydroxyheptanal.

Embodiment 59: An embodiment of embodiment 58, wherein the production of 7-AHA comprises transamination of pimelate semialdehyde Embodiment 60: An embodiment of any of the embodiments of embodiment 55, wherein the aminated aliphatic compound is 6-aminohexanoic acid.

Embodiment 61: An embodiment of embodiment 55, wherein the aminated aliphatic compound is an aliphatic amino alcohol.

Embodiment 62: An embodiment of embodiment 61, wherein the aliphatic amino alcohol is 7-aminoheptanol.

Embodiment 63: An embodiment of embodiment 61, wherein the aliphatic amino alcohol is 6-aminoheptanol.

Embodiment 64: An embodiment of embodiment 55, wherein the aminated aliphatic compound is a diamine.

Embodiment 65: An embodiment of embodiment 64, wherein the diamine is heptamethylenediamine.

Embodiment 66: An embodiment of embodiment 64, wherein the diamine is hexamethylenediamine.

Embodiment 67: An embodiment of any of the embodiments of embodiment 51-66, wherein the ω-transaminase is classified under EC 2.6.1.18, EC 2.6.1.19, EC 2.6.1.29, EC 2.6.1.48, or EC 2.6.1.82.

Embodiment 68: An embodiment of any of the embodiments of embodiment 51-67, wherein the ω-transaminase has at least 70% sequence identity with a *Chromobacterium violaceum* ω-transaminase.

Embodiment 69: An embodiment of any of the embodiments of embodiment 51-68, further comprising: purifying the aminated aliphatic compound.

Embodiment 70: An embodiment of any of the embodiments of embodiment 51-69, wherein the recombinant organism is prokaryotic Embodiment 71: An embodiment of any of the embodiments of embodiment 51-69, wherein the recombinant organism is eukaryotic.

Embodiment 72: An embodiment of any of the embodiments of embodiment 51-71, wherein the culturing is in aerobic conditions.

Embodiment 73: An embodiment of any of the embodiments of embodiment 51-71, wherein the culturing is in anaerobic conditions.

Embodiment 74: An embodiment of any of the embodiments of embodiment 51-71, wherein the culturing is in micro-aerobic conditions.

Embodiment 75: An embodiment of any of the embodiments of embodiment 51-74, wherein the culturing is in conditions of nutrient limitation.

Embodiment 76: An embodiment of any of the embodiments of embodiment 51-75, wherein the culturing comprises introducing to the recombinant organism a carbon source derived from a biological feedstock.

Embodiment 77: An embodiment of any of the embodiments of embodiment 51-75, wherein the culturing comprises introducing to the recombinant organism a carbon source derived from a non-biological feedstock.

Embodiment 78: An embodiment of any of the embodiments of embodiment 51-77, further comprising: improving the tolerance of the recombinant organism to increasing concentrations of the aminated aliphatic compound by continuous cultivation in a selective environment.

Embodiment 79: A recombinant organism engineered to comprise one or more exogenous, modified, or overexpressed polypeptides; wherein each of the one or more polypeptides independently encodes at least one enzyme of an aminated aliphatic compound biosynthesis or export pathway; and wherein at least one of the one or more polypeptides encodes an ω-transaminase having at least 70% identity to SEQ ID NO: 1, or a functional fragment thereof.

Embodiment 80: An embodiment of embodiment 79, comprising two or more exogenous, modified, or overexpressed polypeptides; and wherein the two or more polypeptides each independently encode at least one enzyme selected from the group consisting of an ω-transaminase, a thioesterase, a carboxylate reductase, an acetyl-CoA synthetase, a β-alanine CoA transferase, a 6-phosphogluconate dehydrogenase, a transketolase, a puridine nucleotide transhydrogenase, a glyceraldehyde-3P-dehydrogenase, a malic enzyme, a glucose-6-phosphate dehydrogenase, a glucose dehydrogenase, a fructose 1,6 diphosphatase, an L-alanine dehydrogenase, a L-glutamate dehydrogenase, a formate dehydrogenase, an L-glutamine synthetase, a diamine transporter, a dicarboxylate transporter, an amino acid transporter, and a multidrug transporter Embodiment 81: An embodiment of embodiment 79 or 80, wherein the ω-transaminase is classified under EC 2.6.1.18, EC 2.6.1.19, EC 2.6.1.29, EC 2.6.1.48, or EC 2.6.1.82.

Embodiment 82: An embodiment of any of the embodiments of embodiment 79-81, wherein the recombinant organism has increased ω-transaminase activity as compared to that of a corresponding organism not engineered to comprise the one or more exogenous, modified, or overexpressed polypeptides.

Embodiment 83: The recombinant organism of an embodiment of any of the embodiments of embodiment 79-82, wherein the recombinant organism produces the aminated aliphatic compound or a salt thereof at a higher yield as compared to that of a corresponding organism not engineered to comprise the one or more exogenous, modified, or overexpressed polypeptides.

Embodiment 84: An embodiment of any of the embodiments of embodiment 79-83, wherein at least one of the one or more polypeptides encodes a modified ω-transaminase having one or more amino acid substitutions relative to a wild-type ω-transaminase, and wherein the substitutions are at positions 2, 13, 15, 16, 20, 87, 134, 288, or 345 of SEQ ID NO: 1.

Embodiment 85: An embodiment of any of the embodiments of embodiment 84, wherein the one or more amino acid substitutions are in the small binding pocket (O-pocket) and/or in the large binding pocket (P-pocket) of the at least one polypeptide encoding the modified ω-transaminase.

Embodiment 86: An embodiment of embodiment 84 or 85, wherein the modified ω-transaminase has increased activity and/or improved substrate specificity relative to the wild-type ω-transaminase.

Embodiment 87: An embodiment of any of the embodiments of embodiment 84-86, wherein the wild-type ω-transaminase has at least 70% sequence identity with a *Chromobacterium violaceum* ω-transaminase.

Embodiment 88: An embodiment of any of the embodiments of embodiment 84-87, wherein the modified ω-transaminase has at least 10% greater activity relative to the wild-type ω-transaminase.

Embodiment 89: An embodiment of any of the embodiments of embodiment 84-88, wherein the modified ω-transaminase has a reduced $K_m$ for an amino donor relative to that of the wild-type ω-transaminase.

Embodiment 90: An embodiment of embodiment 89, wherein the amino donor is L-alanine.

Embodiment 91: An embodiment of embodiment 89 or 90, wherein the modified ω-transaminase has a $K_m$ of less than 4 mmol·$L^{-1}$ for the amino donor.

Embodiment 92: An embodiment of any of the embodiments of embodiment 84-91, wherein the modified ω-transaminase has an increased $K_m$ for the aminated aliphatic compound relative to that of the wild-type ω-transaminase.

Embodiment 93: An embodiment of any of the embodiments of embodiment 79-92, wherein at least one of the one or more peptides encodes a cyclizing enzyme capable of catalyzing a conversion of the aminated aliphatic compound to a lactam.

Embodiment 94: An embodiment of embodiment 93, wherein the cyclizing enzyme has at least 70% sequence identity with a *Clostridium propionicum* β-alanine CoA transferase.

Embodiment 95: An embodiment of any of the embodiments of embodiment 93 or 94, wherein the cyclizing enzyme is capable of catalyzing a conversion of 7-AHA to heptanolactam.

Embodiment 96: An embodiment of any of the embodiments of embodiment 79-95, wherein at least one of the one or more polypeptides encodes an amino donor synthesis enzyme capable of catalyzing a synthesis of an amino group donor that is a precursor of the animated aliphatic compound.

Embodiment 97: An embodiment of embodiment 96, wherein the amino donor synthesis enzyme is an L-amino acid dehydrogenase.

Embodiment 98: An embodiment of embodiment 97, wherein the amino donor synthesis enzyme is L-alanine dehydrogenase.

Embodiment 99: An embodiment of any of the embodiments of embodiment 79-98, wherein at least one of the one or more polypeptides encodes an amino acid transporter capable of catalyzing an export of the aminated aliphatic compound from the organism.

Embodiment 100: An embodiment of embodiment 99, wherein the transporter is a lysine exporter.

Embodiment 101: An embodiment of any of the embodiments of embodiment 79-100, wherein the amount of at least one product formed from the aminated aliphatic compound in a reverse reaction catalyzed by the ω-transaminase is reduced as compared to that of a corresponding organism not engineered to comprise the one or more exogenous, modified, or overexpressed polypeptides.

Embodiment 102: An embodiment of embodiment 101, wherein the at least one product comprises pimelate semialdehyde, and wherein the aminated aliphatic compound is 7-AHA.

Embodiment 103: An embodiment of any of the embodiments of embodiment 79-102, wherein the recombinant organism is prokaryotic.

Embodiment 104: An embodiment of any of the embodiments of embodiment 79-102, wherein the recombinant organism is eukaryotic.

Embodiment 105: A method for improved biosynthesis of caprolactam, the method comprising: a) providing a recombinant organism capable of biosynthesizing caprolactam; wherein the recombinant organism has been engineered to comprise two or more exogenous, modified, or overexpressed polypeptides; wherein each of the one or more polypeptides independently encodes at least one enzyme of an caprolactam biosynthesis or export pathway; wherein at least one of the two or more polypeptides encodes an ω-transaminase having at least 70% identity to SEQ ID NO: 1, or a functional fragment thereof; and wherein at least one of the two or more polypeptides encodes a (3-alanine CoA transferase; b) culturing the recombinant organism under conditions suitable for the recombinant organism to convert adipic acid or adipic acid derivatives to caprolactam; and c) purifying the caprolactam.

Embodiment 106: An embodiment of embodiment 105, wherein at least one of the two or more polypeptides encodes a modified ω-transaminase having one or more amino acid substitutions relative to a wild-type ω-transaminase, and wherein the substitutions are at positions 2, 13, 15, 16, 20, 87, 134, 288, or 345 of SEQ ID NO: 1.

Embodiment 107: An embodiment of embodiment 105 or 106, wherein at least one of the two or more polypeptides encoding a β-alanine CoA transferase converts 6-AHA to caprolactam.

Embodiment 108: An embodiment of any of the embodiments of embodiment 105-107, wherein the ω-transaminase is classified under EC 2.6.1.18, EC 2.6.1.19, EC 2.6.1.29, EC 2.6.1.48, or EC 2.6.1.82.

Embodiment 109: An embodiment of any of the embodiments of embodiment 105-108, wherein the adipic acid derivatives comprise adipoyl-ACP and adipic acid semialdehyde.

Embodiment 110: An embodiment of embodiment 109, wherein the conversion of adipic acid or adipic acid derivatives to caprolactam comprises transamination of adipic acid semialdehyde to produce 6-AHA.

Embodiment 111: A bioderived aminated aliphatic compound having a carbon chain length of C5-C19, heptanolactam, caprolactam or salt thereof that is produced by an embodiment of any of the embodiments of embodiment 1-78 and 105-110.

Embodiment 112: A product comprising a chemical produced from an embodiment of embodiment 111, wherein the product comprises a nylon intermediate, a polyester, a pharmaceutical, a biofuel, a fragrance or a food additive.

Embodiment 112: An embodiment of any of the embodiments of embodiment A bio-derived, bio-based or fermentation-derived product, wherein said product comprises: i. a composition comprising at least one bio-derived, bio-based or fermentation-derived compound, or salts thereof, produced or biosynthesized according to any one of claims 1-78 and 105-110; ii. a bio-derived, bio-based or fermentation-derived polymer comprising the bio-derived, bio-based or fermentation-derived composition or compound of i., or any combination thereof; iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof; iv. a substance obtained by molding the bio-derived, bio-based or fermentation-derived polymer of ii. or the bio-derived, bio-based or fermentation-derived resin of iii., or any combination thereof; v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, bio-based or fermentation-derived substance of iv, or any combination thereof; or vi. a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

EXAMPLES

The following examples are provided by way of illustration only and not by way of limitation. Those of skill in the art will readily recognize a variety of non-critical parameters that could be changed or modified to yield essentially the same or similar results.

Studies were performed to determine whether the low performance of the TA reaction is substrate dependent (i.e. the given amino donor is not efficiently used up by the specific TA) or equilibrium dependent (i.e. the transamination of pimelate semialdehyde to 7-AHA itself is inherently inefficient, regardless of the amino donor or transaminase used, for example, because of unfavourable reaction thermodynamics) to develop strategies for the optimization of this metabolic step. Therefore, an extensive screening of ω-TAM variants from different organisms was performed to identify TAs that facilitate a higher reaction rate resulting in increased 7-AHA production levels.

In this extensive screen, only 14% of the screened TA candidates (172 out of 1229) were active. This list was narrowed down to 17 TAs from different organisms, which required high concentrations of L-alanine ($Km \approx 4\text{-}10$ $mmol \cdot L^{-1}$) in the forward reaction (pimelate semialdehyde+ L-alanine-->7-AHA+pyruvate) and exhibited very slow kinetics.

Based on this data, it was hypothesized that either the given amino donor is not efficiently used up by the specific TA or that the transamination of pimelate semialdehyde to 7-AHA itself is inherently inefficient, regardless of the amino donor or TA used.

Bioinformatics Analysis

To test whether a better amino donor could be identified, and before conducting in vitro assays, bioinformatics analysis and literature research aimed at reducing the number of transaminases to be tested, while maintaining the same diversity in enzyme features, such as predicted amino donors, Pfam domains and amino acid sequence in proximity of the PLP binding site, were performed. Pfam conserved domain research suggested that all TA candidates belong to the Aminotransferase Class III group. Although 14 out of the 17 TAs identified in the initial screen harboured the BioA conserved domain (E-value=0), which would suggest S-adenosyl methionine (SAM) to be the preferred amino donor, all of them also showed over 60% sequence identity to aspartate and/or 4-aminobutyrate transaminases. Clear-cut data on the activities of the TAs towards specific amino donors and amino acceptors could not be found in the literature.

In order to maintain the same level of diversity in nine TAs identified from the original list of TAs, additional selection criteria based on the amino acid sequence observed in proximity of the PLP binding site were added. After analysis for presence of pyridoxal phosphate (PLP) binding sequences (identified through multi-alignment based on TA-Cv crystal structure), and discarding the candidates with highest $K_m$ towards pimelate semialdehyde (data provided by Invista) (except controls TA-Vf and TA-Cv) and greater than 60% identity with any other TA in the list (based on ClustalW multi-alignment), the list of candidate TA enzymes was narrowed down to 9, including TA-Cv and TA-Vf (Table 3). These nine TAs were further characterized in vitro using either cell free extract (CFE) or purified enzyme.

TABLE 3

List of selected TAs after bioinformatics analysis and literature research. TAs were selected based on predicted amino donor, amino acidic sequence in proximity of the pyridoxal phosphate (PLP) binding site, Km value towards pimelate semialdehyde and % identity with the other TAs provided by Invista.

| Uniprot # | Designation | pINV # | INV# | Expected MW |
|---|---|---|---|---|
| A0A0H1A7R9 | TA_011 | pINV0361 | INV 0734 | 51.6 |
| B9L0N2 | TA_012 | pINV0366 | INV 0741 | 53.1 |
| D7A1Z2 | TA_013 | pINV0367 | INV 0742 | 51.4 |
| D7CVJ6 | TA_002 | pINV0368 | INV 0743 | 48.6 |
| Empty vector | Empty vector | pINV0369 | INV 0744 | — |
| F2XBU9 | TA-Vf | pINV0370 | INV 0745 | 51.5 |
| H0I025 | TA_015 | pINV0372 | INV 0747 | 52.1 |
| J2TM48 | TA_016 | pINV0373 | INV 0748 | 51.1 |
| K2KXB1 | TA_017 | pINV0374 | INV 0749 | 51.4 |
| Q7NWG4 | TA-Cv | pINV0375 | INV 0750 | 52.6 |

Initial In Vitro Amino Donor Screening with TA CFE (110517-N7SD-WP2/3-26)

Figure 4:
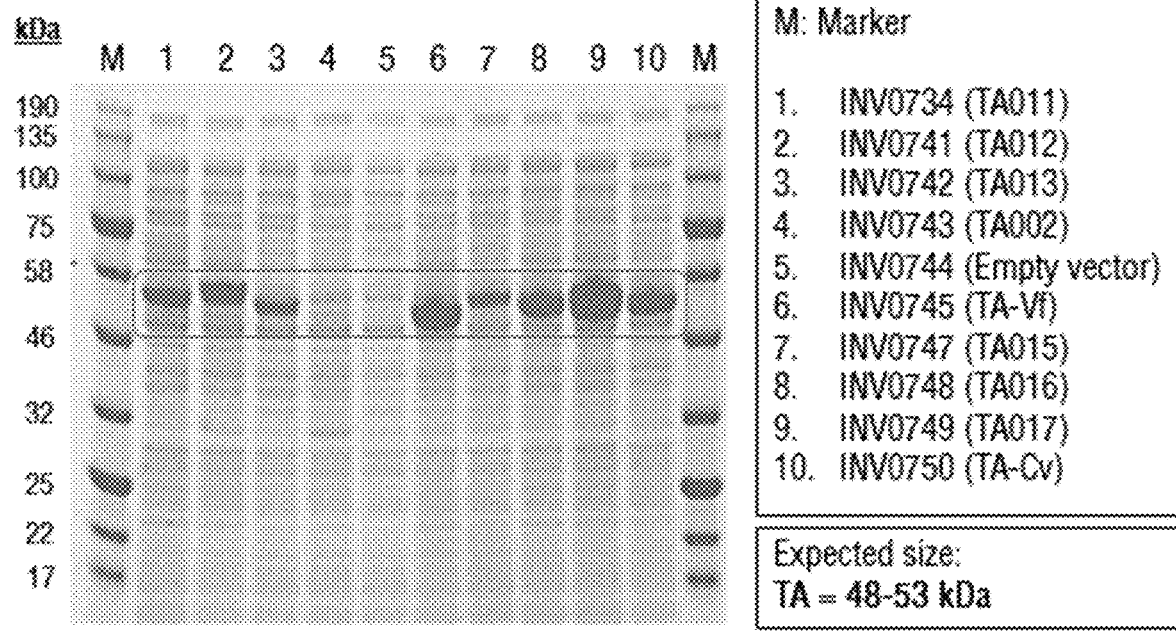
FIG. 4 shows SDS-PAGE analysis of generated cell free extracts (CFE) upon IPTG induction of the corresponding transaminases (TAs).

In this initial test, activity of the 9 selected TAs (Table 3) towards different amino donors was assayed in cell-free extract derived from IPTG-induced cultures harbouring the corresponding TA plasmids. As an internal control for recombinant protein expression across cell-free extracts, SDS-PAGE analysis was carried out (FIG. 4). Besides TA_002 (INV0743), all selected TAs showed clear visible expression on SDS-PAGE matching the predicted molecular weights.

Figure 5:
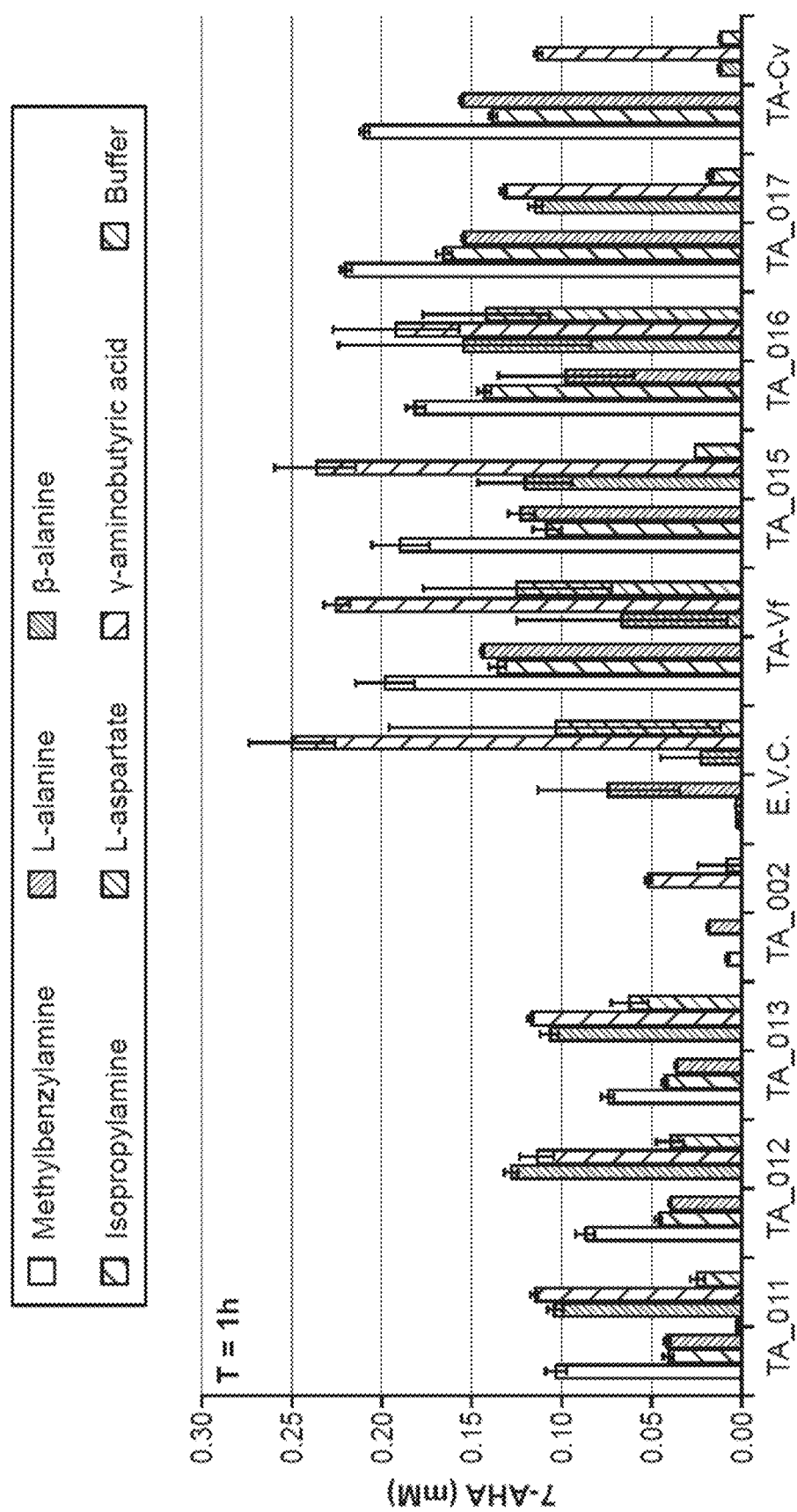
FIG. 5 shows 7-AHA levels determined by LC-MS after 1 h incubation of CFE expressing 9 selected TAs with methylbenzylamine, isopropylamine, L-alanine, L-glutamate, β-alanine and γ-aminobutyric acid as amino donors. 300 μL CFE were incubated with 10 mmol·L$^{-1}$ pimelate semialdehyde, 50 mmol·L$^{-1}$ amino donor (5 fold excess amino donor to amino acceptor) and 0.2 mmol·L$^{-1}$ PLP for 1 h. A negative control sample for each TA was included by replacing the amino donor volume with assay buffer. An empty vector control (E.V.C.) CFE was included in the assay for determination of native TA activity. Values are presented as mean±Std dev (n=3).

Based on bioinformatics analysis and literature research, the 17 TAs identified in the screening assay were clustered into 5 major groups and 9 TAs were identified, each having biochemical properties assumed to be representative of the whole list. For practical and economic reasons, these TAs were screened for activity towards methylbenzylamine, isopropylamine, L-alanine, L-glutamate, β-alanine and γ-aminobutyric acid; SAM was not included in this preliminary test. CFE obtained from IPTG-induced cultures expressing one of each of the selected TAs were incubated with 10 mmol·L$^{-1}$ pimelate semialdehyde, 0.2 mmol·L$^{-1}$ PLP and 50 mmol·L$^{-1}$ amino donor (or buffer). 7-AHA production was assessed after 1 h of incubation (FIG. 5); CFE obtained from a control strain was also included in the assay as a comparison.

The empty vector control strain exhibited significant production of 7-AHA when γ-aminobutyric acid and L-alanine where used as amino donors, suggesting that endogenous TA(s) could convert pimelate semialdehyde into the expected product. Interestingly, this control showed 7-AHA production even when no amino donor was added to the CFE, albeit with a big standard deviation. Assessed CFE could also be generally grouped into high (TA-Vf, TA_015, TA_016, TA_017 and TA-Cv) and low (TA_011, TA_012, TA_013 and TA_002) activity towards the amino donors tested. CFE for TA_002 exhibited the lowest levels of 7-AHA with all the amino donors used (FIG. 5), which is consistent with its lack of visible expression on SDS-PAGE (FIG. 1). In line with the bioinformatics analysis performed on the selected TAs, showing more than 60% sequence similarity to 4-Aminobutyrate transaminases, γ-aminobutyric acid and methylbenzylamine exhibited the highest 7-AHA production across all tested CFEs, with the exception of TA_017 and TA-Cv whose CFE showed higher 7-AHA yields in presence of L-alanine.

In Vitro Amino Donor Screening with CFE and Purified TAs (II0517-N7SD-WP2/3-66)

Based on previous CFE results showing significant 7-AHA production in the empty vector control sample, an additional in vitro test was performed on purified TAs to discriminate between background response and TA activity. The CFE test was also repeated alongside in order to show reproducibility. To this aim, 2 TAs from the high activity group (TA_15 and TA_017) and one from the low activity group (TA_11), in addition to TA-Cv, which served as a positive control, were screened with L-alanine (which exhibited particularly high activity with TA_017 and TA-Cv in previous tests), γ-aminobutyric acid (which exhibited high activity across all TAs) and SAM (which was predicted as an amino donor for all TAs based on the bioinformatics analysis).

Figure 6:
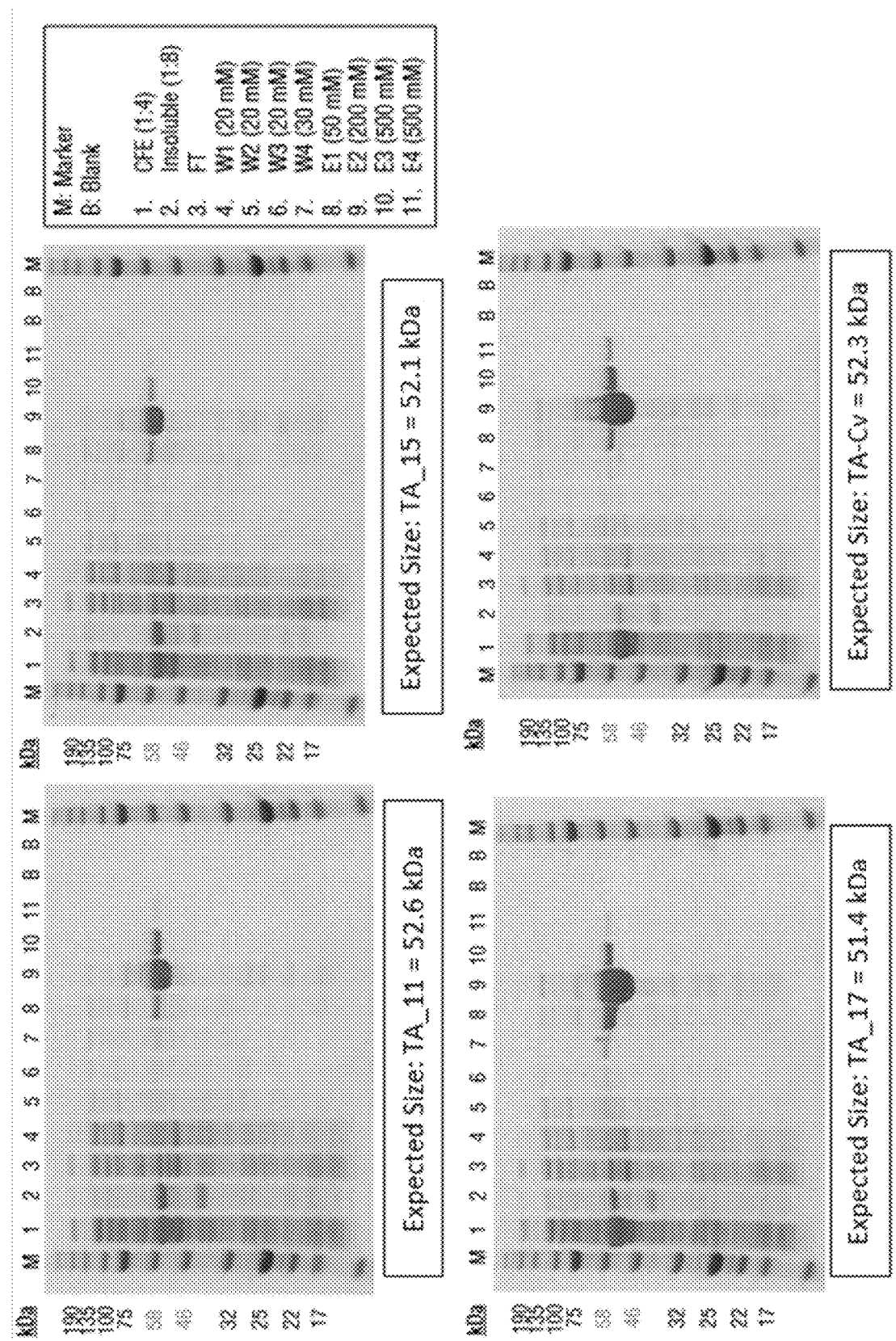
FIG. 6 shows SDS-page analysis of TA samples obtained from Ni-NTA agarose resin purification. Purified TA_11 (top left), TA_15 (top right), TA_17 (bottom left) and TA-Cv (bottom right) were assessed for amino donor specificity. Fractions were run on Bolt™ 4-12% Bis Tris Plug Gel (15 Well) for 20 min at 200 V and stained with Coomassie instant Blue.
Figure 7:
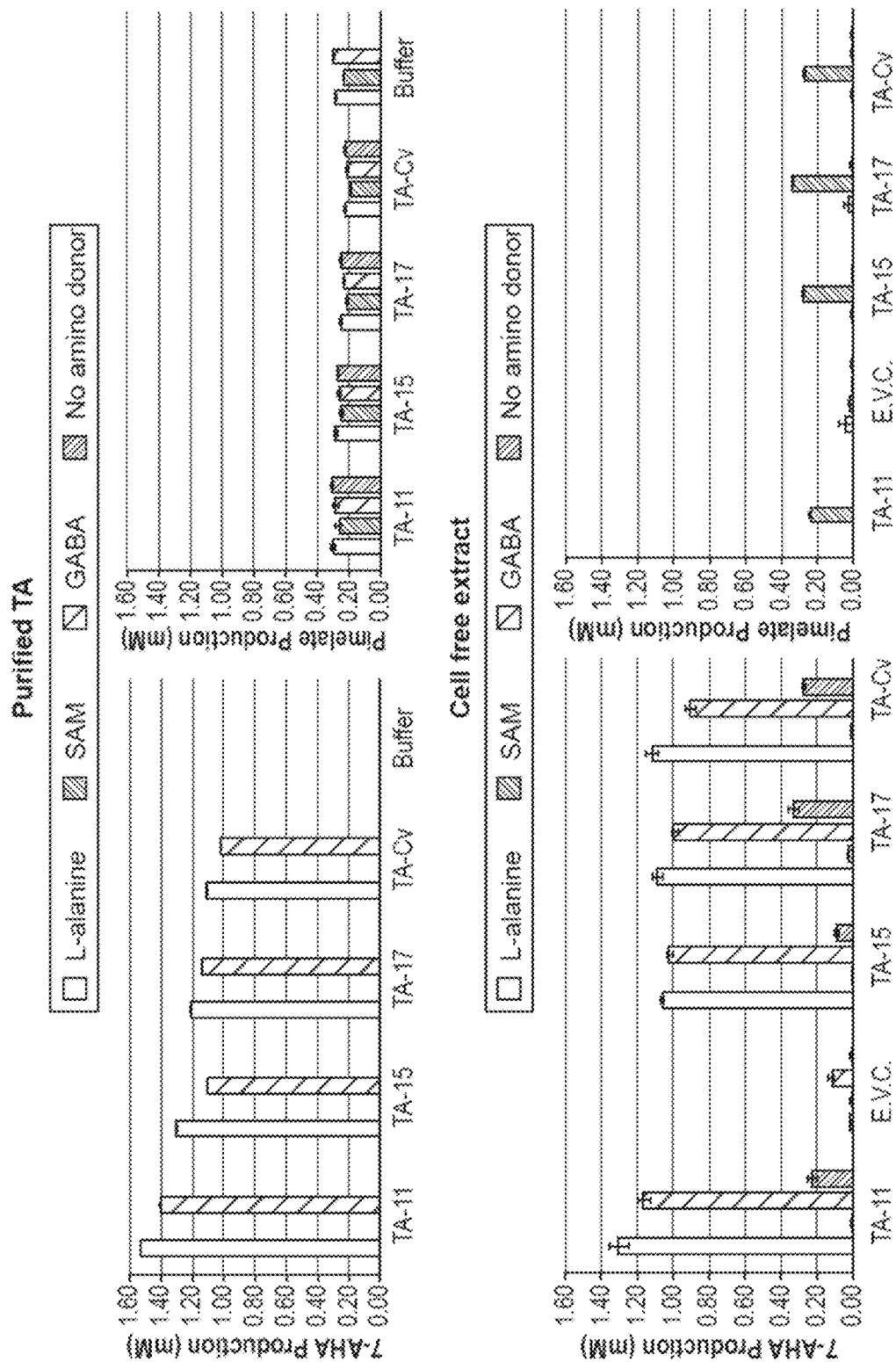
FIG. 7 shows 7-AHA and pimelate levels measured after 1 h incubation of purified TAs (top) and induced CFE (bottom) with L-alanine, SAM and GABA as determined by LC-MS analysis. 300 μL CFE or 1.5 μmol·L$^{-1}$ purified TA were incubated with 5 mmol·L$^{-1}$ pimelate semialdehyde, 25 mmol·L$^{-1}$ amino donor (5 fold excess amino donor to amino acceptor) and 0.1 mmol·L$^{-1}$ PLP for 1 h. Negative control samples (Buffer and E.VC.) were included in both assays. Values are presented as mean±Std dev (n=3).

Purified recombinant protein fractions for each TA were generated by incubating CFE with Ni-NTA agarose resin followed by wash and elution with increasing concentrations of imidazole. Relatively pure and concentrated TA fractions were obtained after elution with 200 mmol·L$^{-1}$ imidazole (elution 2, lane 9; FIG. 6). These elution fractions were dialyzed overnight and used in subsequent in vitro assay. 300 µL CFE or 1.5 µmol·L$^{-1}$ of each respective purified TA were incubated with 5 mmol·L$^{-1}$ pimelate semialdehyde, 0.1 mmol·L$^{-1}$ PLP and 25 mmol·L$^{-1}$ of amino donor (L-alanine, SAM, GABA or no amino donor). Negative controls were included both in the purified TA assay (no enzyme control) and CFE-based assay (empty vector control CFE). Production of both 7-AHA and pimelate was assessed 1 h from the beginning of the reaction (FIG. 7).

Low levels of pimelate (4% conversion) were detected in the assays using purified TAs, suggesting that pimelate semialdehyde is relatively stable during the 1 h assay. Interestingly, all tested TAs showed activity towards L-alanine and GABA as amino donors. A mmol·L$^{-1}$ of 7-AHA (20% conversion) was observed across all of the tested TAs. However, no 7-AHA was produced upon enzyme incubation with SAM. These results show a good match between the two experiments using CFE or purified TAs. Given the comparable yields in 7-AHA across different TAs and amino donors tested, the overall low performance of the TA step in the 7-AHA pathway seems to be due to an unfavourable reaction equilibrium, rather than being linked to a specific enzyme.

Based on this, it was hypothesized that the low conversion efficiency observed in the previous experiment could be due to a product loop, whereby the ω-TAM recycles 7-AHA back into pimelate semialdehyde. In line with this, similar levels of 7-AHA were detected when L-alanine or 6-ACA were used as amino donors for TA-Cv.

Assessment of ω-TAM Reaction Product Loop

The reaction catalysed by ω-TAM is reversible, as the produced 7-AHA can, in turn, be used as an amino donor in the reverse reaction, thereby regenerating pimelate semialdehyde. Previous results have confirmed the activity of a purified *Chromobacterium violaceum* TA (TA-Cv) on both L-alanine and GABA as amino donors in the forward reaction. To assess the occurrence of a product loop, whereby 7-AHA is used as amino donor to regenerate pimelate semialdehyde in the reverse reaction, 7-AHA levels were measured upon incubation of TA-Cv with pimelate semialdehyde (amino acceptor) together with L-alanine (amino donor), 6-ACA (used was as proxy for 7-AHA in the reverse reaction) or both for 1 h. Similar levels of 7-AHA (1-1.5 mmol·L$^{-1}$) were detected when L-alanine or 6-ACA were used as independent amino donors for pimelate semialdehyde, indicating the occurrence of a product loop where 6-ACA is transaminated to pimelate semialdehyde with comparable efficiencies. Moreover, simultaneous incubation of L-alanine and 6-ACA with pimelate semialdehyde did not increase further 7-AHA product formation, confirming that TA-Cv can use both substrates as amino donors for the transamination reaction, causing the occurrence of the product loop.

Assessment of ω-TAM Reaction Product Loop (II0517-N7SD-WP2/3-70)

The reaction catalysed by ω-TAM is reversible, as the produced 7-AHA can in turn be used as amino donor in the reverse reaction, thereby regenerating pimelate semialdehyde. Previous results have confirmed the activity of purified TA-Cv on both L-alanine and GABA as amino donors in the forward reaction. In order to assess the occurrence of a product loop, whereby 7-AHA is used as amino donor to re-generate pimelate semialdehyde in the reverse reaction, 7-AHA levels were measured upon incubation of TA-Cv with pimelate semialdehyde (amino acceptor) together with L-alanine (amino donor), 6-ACA (used as proxy for 7-AHA in the reverse reaction) or both for 1 h.

Figure 8:
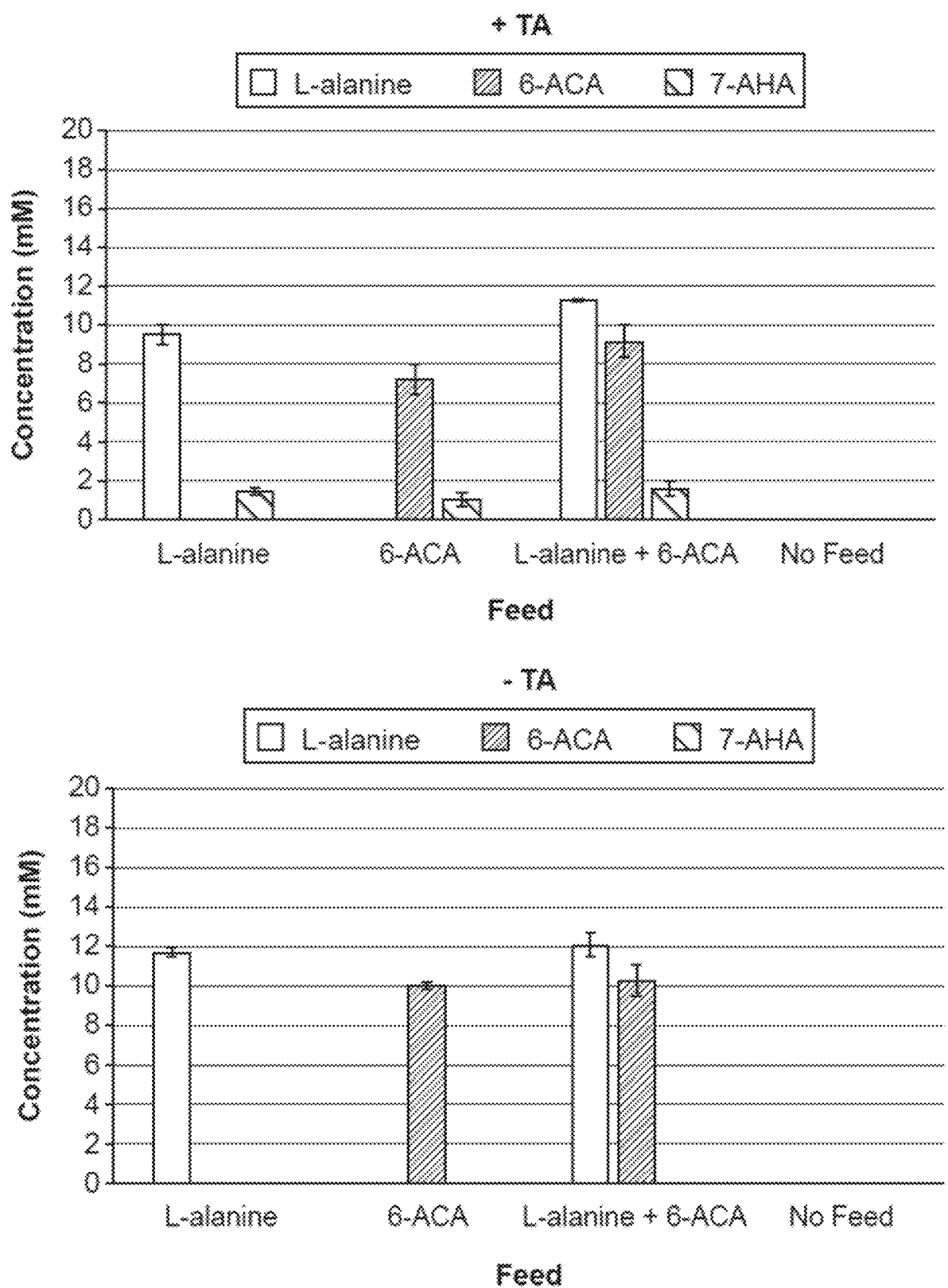
FIG. 8 shows L-alanine, 6-ACA and 7-AHA levels measured after 1 h incubation of pimelate semialdehyde with L-alanine, 6-ACA or both, with (top) or without (bottom) purified TA-Cv as determined by HPLC analysis. 1.5 μmol·L$^{-1}$ of purified TA-Cv was incubated with 5 mmol·L$^{-1}$ pimelate semialdehyde, 10 mmol·L$^{-1}$ amino donor and 0.1 mmol·L$^{-1}$ PLP for 1 h (top panel). A negative control sample was included by replacing the amino donor with assay buffer (no feed). Values are presented as mean±Std dev (n=3).

As seen in FIG. 8, similar levels of 7-AHA (1-1.5 mmol·L$^{-1}$) were detected when L-alanine or 6-ACA were used as independent amino donors for pimelate semialdehyde, indicating the occurrence of a product loop where 6-ACA is transaminated to pimelate semialdehyde with comparable efficiencies. Moreover, simultaneous incubation of L-alanine and 6-ACA with pimelate semialdehyde did not increase further 7-AHA product formation, confirming that TA-Cv can use both substrates as amino donors for the transamination reaction, causing the occurrence of the product loop.

Cyclization

Removal of the produced 7-AHA is a potential strategy to shift the ω-TAM reaction equilibrium and prevent the observed product loop accounting for a reduced conversion efficiency of pimelate semialdehyde to 7-AHA. In a recent paper, Chae et al. ("Metabolic engineering of *Escherichia coli* for the production of four-, five- and six-carbon lactams," *Metabolic Engineering* 41: 82-91 (2017)) reported construction of a new and efficient metabolic pathway for the production of six-carbon lactams (caprolactam) from the respective ω-amino acid. This system did not yield any heptanolactam (seven-carbon lactam) when 7-AHA was used as a substrate, likely because the chance of cyclization through joining amine and CoA functional groups is lower for a C7 ω-amino acyl-CoA.

The aim of this work was to determine whether cyclization of 6-ACA, the 6-carbon equivalent of 7-AHA, to caprolactam, could be used to shift the ω-TAM reaction towards formation of the products in vitro. Chae et al. has shown that the conversion of 6-ACA to caprolactam is a two step-reaction: *Clostridium propionicum* β-alanine CoA transferase (CpACT) catalyzes the transfer of CoA to 6-ACA, thus generating 6-ACA-CoA; subsequently, activated 6-ACA undergoes spontaneous cyclization, resulting in caprolactam formation. Therefore, studies were performed to determine whether cyclization of 6-ACA, the 6-carbon equivalent of 7-AHA, to caprolactam could be used to shift the ω-TAM reaction towards formation of the products.

For the in vitro assay, purified CpACT activity and the ability to shift the ω-TAM reaction was evaluated by measuring caprolactam formation upon incubation with adipate semi-aldehyde and purified ω-TAM. The in vitro test was performed to determine whether recombinant CpACT was active and to what extent this enzyme was able to shift the equilibrium of the ω-TAM reaction. In these studies, CpACT was active and able to partially shift the equilibrium of the ω-TAM reaction in vitro.

For in vivo assays, caprolactam production can be assessed in strains carrying the bottom part of the 6-ACA pathway (CAR, TAM, lysE, sfp) together with CpACT, both under the control of constitutive promoters of increasing strength (either ProC or ProD). Constructed plasmids can be tested in both the control ΔbioF and ΔbioF Δ12ADH (ΔybbO ΔyahK ΔahR ΔahdP ΔyqhD ΔyiaY ΔfucO ΔeutG ΔdkgA ΔyghZ ΔdkgB ΔydfG) genetic backgrounds to assess the impact of endogenous Alcohol dehydrogenase genes on product formation. These strains can be assessed for growth, CpACT expression levels and caprolactam formation relative to empty vector controls.

What is claimed is:

1. A method for biosynthesis of an aminated aliphatic compound, the method comprising:
   a) providing a recombinant microorganism capable of biosynthesizing an aminated aliphatic compound; wherein the recombinant microorganism has been engineered to comprise one or more polypeptides, wherein each of the one or more polypeptides independently encodes at least one enzyme of an aminated aliphatic compound biosynthesis or export pathway; and wherein at least one of the one or more polypeptides encodes an ω-transaminase having at least 70% identity to SEQ ID NO: 1, and comprising substitutions at positions 2, 13, 15, 16, 20, 87, 134, 288, or 345 of SEQ ID NO: 1 and wherein an amino acid corresponding to position 345 of SEQ ID NO: 1 is substituted with arginine; and
   b) culturing the recombinant microorganism under conditions suitable for the recombinant microorganism to produce the aminated aliphatic compound or a salt thereof.

2. The method of claim 1, wherein the recombinant microorganism has been engineered such that the one or more polypeptides comprises two or more polypeptides that each independently encode at least one enzyme selected from the group consisting of an ω-transaminase, a thioesterase, a carboxylate reductase, an acetyl-CoA synthetase, a β-alanine CoA transferase, a 6-phosphogluconate dehydrogenase, a transketolase, a puridine nucleotide transhydrogenase, a glyceraldehyde-3P-dehydrogenase, a malic enzyme, a glucose-6-phosphate dehydrogenase, a glucose dehydrogenase, a fructose 1,6 diphosphatase, an L-alanine dehydrogenase, a L-glutamate dehydrogenase, a formate dehydrogenase, an L-glutamine synthetase, a diamine transporter, a dicarboxylate transporter, an amino acid transporter, and a multidrug transporter.

3. The method of claim 1, wherein the ω-transaminase is classified under EC 2.6.1.18, EC 2.6.1.19, EC 2.6.1.29, EC 2.6.1.48, or EC 2.6.1.82.

4. The method of claim 1, wherein at least one of the one or more polypeptides encodes a cyclizing enzyme capable of catalyzing a conversion of the aminated aliphatic compound to a lactam, and wherein the cyclizing enzyme is a *Clostridium propionicum* β-alanine CoA transferase.

5. The method of claim 1, wherein the culturing comprises introducing to the recombinant microorganism an amino group donor that is a precursor of the aminated aliphatic compound, wherein the aminated aliphatic compound is volatile under microbial fermentation conditions at atmospheric pressure and at a temperature from 20° C. to 65° C., and wherein the amino group donor comprises isopropylamine.

6. The method of claim 1, wherein at least one of the one or more polypeptides encodes an amino donor synthesis enzyme capable of catalyzing a synthesis of an amino group donor that is a precursor of the animated aliphatic compound, and wherein the amino donor synthesis enzyme is an L-amino acid dehydrogenase.

7. The method of claim 1, wherein at least one of the one or more polypeptides encodes an amino acid transporter capable of catalyzing an export of the aminated aliphatic compound from the microorganism, and wherein the transporter is a lysine exporter.

8. The method of claim 1, wherein the amount of at least one product formed from the aminated aliphatic compound in a reverse reaction catalyzed by the ω-transaminase is reduced as compared to that of a corresponding microorganism not engineered to comprise the polypeptides.

9. The method of claim 1, further comprising:
purifying the aminated aliphatic compound.

10. A recombinant microorganism engineered to comprise one or more polypeptides; wherein each of the one or more polypeptides independently encodes at least one enzyme of an aminated aliphatic compound biosynthesis or export pathway; and wherein at least one of the one or more polypeptides encodes an ω-transaminase having at least 70% identity to SEQ ID NO: 1, and comprising substitutions at positions 2, 13, 15, 16, 20, 87, 134, 288, or 345 of SEQ ID NO: 1 and wherein an amino acid corresponding to position 345 of SEQ ID NO: 1 is substituted with arginine.

11. The recombinant microorganism of claim 10; wherein the one or more polypeptides comprises two or more polypeptides; and wherein the two or more polypeptides each independently encode at least one enzyme selected from the group consisting of an ω-transaminase, a thioesterase, a carboxylase reductase, an acetyl-CoA synthetase, a β-alanine CoA transferase, a 6-phosphogluconate dehydrogenase, a transketolase, a puridine nucleotide transhydrogenase, a glyceraldehyde-3P-dehydrogenase, a malic enzyme; a glucose-6-phosphate dehydrogenase, a glucose dehydrogenase, a fructose 1,6 diphosphatase, an L-alanine dehydrogenase, a L-glutamate dehydrogenase, a formate dehydrogenase, an L-glutamine synthetase, a diamine transporter, a dicarboxylate transporter, an amino acid transporter, and a multidrug transporter.

12. The recombinant microorganism of claim 10, wherein at least one of the one or more polypeptides encodes a cyclizing enzyme capable of catalyzing a conversion of the aminated aliphatic compound to a lactam, wherein the cyclizing enzyme is a *Clostridium propionicum* β-alanine CoA transferase.

13. The recombinant microorganism of claim 10, wherein at least one of the one or more polypeptides encodes an amino donor synthesis enzyme capable of catalyzing a synthesis of an amino group donor that is a precursor of the animated aliphatic compound, wherein the amino donor synthesis enzyme is an L-amino acid dehydrogenase.

14. The recombinant microorganism of claim 10, wherein at least one of the one or more polypeptides encodes an amino acid transporter capable of catalyzing an export of the aminated aliphatic compound from the microorganism, wherein the transporter is a lysine exporter.

15. The recombinant microorganism of claim 10, wherein the amount of at least one product formed from the aminated aliphatic compound in a reverse reaction catalyzed by the ω-transaminase is reduced as compared to that of a corresponding microorganism not engineered to comprise the one or more polypeptides.

16. The method of claim 1, wherein at least one of:
an amino acid corresponding to position 2 of SEQ ID NO: 1 is substituted with valine;
an amino acid corresponding to position 13 of SEQ ID NO: 1 is substituted with seine;
an amino acid corresponding to position 15 of SEQ ID NO: 1 is substituted with serine;
an amino acid corresponding to position 16 of SEQ ID NO: 1 is substituted with serine;
an amino acid corresponding to position 134 of SEQ ID NO: 1 is substituted with asparagine; and
an amino acid corresponding to position 288 of SEQ ID NO: 1 is substituted with glutamine.

17. The recombinant microorganism of claim 10, wherein at least one of:
an amino acid corresponding to position 2 of SEQ ID NO: 1 is substituted with valine;
an amino acid corresponding to position 13 of SEQ ID NO: 1 is substituted with seine;
an amino acid corresponding to position 15 of SEQ ID NO: 1 is substituted with serine;
an amino acid corresponding to position 16 of SEQ ID NO: 1 is substituted with serine;
an amino acid corresponding to position 134 of SEQ ID NO: 1 is substituted with asparagine; and
an amino acid corresponding to position 288 of SEQ ID NO: 1 is substituted with glutamine.

* * * * *